US010342649B2

(12) United States Patent
Crunick et al.

(10) Patent No.: US 10,342,649 B2
(45) Date of Patent: *Jul. 9, 2019

(54) SYSTEM AND METHOD FOR TREATING ANIMALS

(75) Inventors: John Crunick, Cranberry Township, PA (US); Tamas Becse, Wexford, PA (US); Louis L. Laskey, Jr., Prospect, PA (US)

(73) Assignee: Sigma Instruments Holdings, LLC, Cranberry Twp., PA (US)

( * ) Notice: Subject to any disclaimer, the term of this patent is extended or adjusted under 35 U.S.C. 154(b) by 1424 days.

This patent is subject to a terminal disclaimer.

(21) Appl. No.: 14/344,313

(22) PCT Filed: Sep. 14, 2012

(86) PCT No.: PCT/US2012/055564
§ 371 (c)(1),
(2), (4) Date: Sep. 24, 2014

(87) PCT Pub. No.: WO2013/040451
PCT Pub. Date: Mar. 21, 2013

(65) Prior Publication Data
US 2015/0080990 A1    Mar. 19, 2015

Related U.S. Application Data

(60) Provisional application No. 61/535,225, filed on Sep. 15, 2011, provisional application No. 61/616,989, filed on Mar. 28, 2012.

(51) Int. Cl.
*A61H 23/02* (2006.01)
*A61N 1/32* (2006.01)
(Continued)

(52) U.S. Cl.
CPC ............. *A61D 1/00* (2013.01); *A61H 23/006* (2013.01); *A61H 23/0245* (2013.01); *A61N 1/32* (2013.01);
(Continued)

(58) Field of Classification Search
CPC ... A61D 1/00; A61N 1/32; A61N 7/00; A61N 1/322; A61H 23/006; A61H 23/0245;
(Continued)

(56) References Cited

U.S. PATENT DOCUMENTS 3,499,437 A    3/1970 Balamuth
4,530,360 A    7/1985 Durate
(Continued)

FOREIGN PATENT DOCUMENTS

DE    10306795 A1    9/2004
KR    10-0400870 B    10/2003
(Continued)

OTHER PUBLICATIONS

International Search Report and Written Opinion, PCT/US2012/055538, dated Jan. 30, 2013, 11 pages.
(Continued)

*Primary Examiner* — Quang D Thanh
(74) *Attorney, Agent, or Firm* — Polsinelli PC

(57) ABSTRACT

A system for treating a tissue of an animal patient. The system may include a display and input device, and at least one instrument chosen from an impulse stimulator instrument and an acoustic oscillator. The impulse stimulator is configured to apply a percussive massage including one or more force impulses. The impulse stimulator is further configured to measure a response of the tissue to one of the applied force impulses to assess a condition of the tissue.
(Continued)

The acoustic oscillator is configured to apply an acoustic stimulation including one or more acoustic pulses to the tissue of the animal patient.

10 Claims, 35 Drawing Sheets

(51) Int. Cl.
    *A61D 1/00*     (2006.01)
    *A61N 7/00*     (2006.01)
    *A61H 23/00*     (2006.01)

(52) U.S. Cl.
    CPC ........ *A61N 7/00* (2013.01); *A61H 2201/1685* (2013.01); *A61H 2201/5005* (2013.01); *A61H 2201/5007* (2013.01); *A61H 2201/5071* (2013.01); *A61H 2203/03* (2013.01); *A61N 1/322* (2013.01)

(58) Field of Classification Search
    CPC ........ A61H 2203/03; A61H 2201/5071; A61H 2201/5005; A61H 2201/1685; A61H 2201/5007
See application file for complete search history.

(56) References Cited

U.S. PATENT DOCUMENTS

| | | |
|---|---|---|
| 4,946,692 A | 8/1990 | Bernhardt et al. |
| 4,984,127 A | 1/1991 | Evans |
| 5,209,221 A | 8/1993 | Riedlinger |
| 5,300,095 A | 4/1994 | Salazar |
| 5,413,550 A | 8/1995 | Castel |
| 5,586,067 A | 12/1996 | Gross |
| 5,601,526 A | 2/1997 | Chapelon et al. |
| 6,321,119 B1 | 11/2001 | Kronberg |
| 6,413,230 B1 | 7/2002 | Haupt et al. |
| 6,419,648 B1 | 7/2002 | Vitek et al. |
| 6,514,220 B2 | 2/2003 | Melton, Sr. et al. |
| 6,539,328 B1 | 3/2003 | Cremonese et al. |
| 6,540,700 B1 | 4/2003 | Fujimoto et al. |
| 6,565,520 B1 | 5/2003 | Young |
| 6,645,162 B2 | 11/2003 | Friedman et al. |
| 7,123,967 B2 | 10/2006 | Weinberg |
| 7,144,417 B2 | 12/2006 | Colloca et al. |
| 7,435,232 B2 | 10/2008 | Liebschner |
| 7,519,427 B2 | 4/2009 | Sakagami et al. |
| 7,894,907 B2 | 2/2011 | Cowan et al. |
| 7,899,542 B2 | 3/2011 | Cowan et al. |
| 8,048,006 B2 | 11/2011 | Harris |
| D711,900 S | 8/2014 | Crunick et al. |
| 9,314,190 B1 | 4/2016 | Giuffrida |
| 9,782,324 B2 * | 10/2017 | Crunick ............. A61H 23/0245 |
| 2002/0099409 A1 | 7/2002 | Hui |
| 2003/0125649 A1 | 7/2003 | McIntosh et al. |
| 2004/0015106 A1 | 1/2004 | Coleman |
| 2004/0171970 A1 | 9/2004 | Schleuniger et al. |
| 2005/0043659 A1 | 2/2005 | Challis et al. |
| 2005/0222524 A1 | 10/2005 | Fielding et al. |
| 2006/0009810 A1 | 1/2006 | Mann et al. |
| 2006/0122579 A1 | 6/2006 | Pisciottano |
| 2006/0160158 A1 | 7/2006 | Ebright |
| 2006/0184075 A1 | 8/2006 | Restle et al. |
| 2007/0073361 A1 | 3/2007 | Goren et al. |
| 2007/0091091 A1 | 4/2007 | Gardiner et al. |
| 2007/0173903 A1 | 7/2007 | Goren et al. |
| 2007/0203533 A1 | 8/2007 | Goren et al. |
| 2007/0239082 A1 | 10/2007 | Schultheiss |
| 2008/0021353 A1 | 1/2008 | Menzi et al. |
| 2008/0077434 A1 | 3/2008 | Man et al. |
| 2008/0183164 A1 | 7/2008 | Elkins |
| 2009/0018404 A1 | 1/2009 | Fendelander et al. |
| 2009/0043293 A1 | 2/2009 | Pankratov |
| 2009/0149782 A1 | 6/2009 | Cohen |
| 2009/0178626 A1 | 7/2009 | Greeson |
| 2009/0326607 A1 | 12/2009 | Castel et al. |
| 2010/0094187 A1 | 4/2010 | Murinson |
| 2010/0105933 A1 | 4/2010 | Chen et al. |
| 2010/0131025 A1 | 5/2010 | Henry |
| 2010/0152624 A1 * | 6/2010 | Tanis ................ A61N 7/00 601/2 |
| 2011/0112405 A1 * | 5/2011 | Barthe ................ A45D 44/005 600/459 |
| 2011/0118810 A1 | 5/2011 | Cowan et al. |
| 2011/0166621 A1 | 7/2011 | Cowan et al. |
| 2011/0171325 A1 | 7/2011 | Lozano |
| 2011/0196438 A1 * | 8/2011 | Mnozil ................ A61B 18/14 607/3 |
| 2011/0213253 A1 | 9/2011 | Kruglick |
| 2012/0271206 A1 * | 10/2012 | Shalev ................ A61H 9/0057 601/15 |
| 2014/0031866 A1 | 1/2014 | Fuhr |
| 2014/0194790 A1 | 7/2014 | Crunick et al. |
| 2016/0113840 A1 | 4/2016 | Crunick et al. |
| 2016/0151238 A1 | 6/2016 | Crunick et al. |
| 2017/0151125 A1 | 6/2017 | Becse et al. |

FOREIGN PATENT DOCUMENTS

| | | |
|---|---|---|
| KR | 10-2010-0082140 A | 7/2010 |
| WO | WO 99-34724 A2 | 7/1999 |
| WO | WO 02-98318 A2 | 12/2002 |
| WO | WO 2010/009141 A1 | 1/2010 |
| WO | WO 2011-080191 A1 | 7/2011 |
| WO | WO 2013/040443 A2 | 3/2013 |
| WO | WO 2013/040451 A2 | 3/2013 |

OTHER PUBLICATIONS

International Search Report and Written Opinion, PCT/US2012/055564, dated Feb. 28, 2013, 10 pages.
International Search Report and Written Opinion, PCT/US2013/021973, dated May 15, 2013, 15 pages.
U.S. Appl. No. 14/344,311, filed Mar. 11, 2014, Crunick et al.
U.S. Appl. No. 14/372,989, filed Jul. 17, 2014, Becse et al.
European Search Report, EP12832599.0, dated Apr. 2, 2015.
International Search Report and Written Opinion, PCT/US2014/040953, dated Oct. 6, 2014.
Chinese Office Action (English), 201480039884.X, dated Aug. 10, 2016.
Extended European Search Report, EP14807934.6, dated Feb. 1, 2017.
Final Office Action, U.S. Appl. No. 14/372,989, dated May 2, 2016.
Final Office Action, U.S. Appl. No. 14/895,843, dated Oct. 17, 2016.
Final Rejection, U.S. Appl. No. 15/373,637, dated Oct. 11, 2017.
Non-Final Office Action, U.S. Appl. No. 14/895,843, dated Apr. 22, 2016.
Non-Final Office Action, U.S. Appl. No. 15/373,637, dated Mar. 15, 2018.
Non-Final Office Action, U.S. Appl. No. 15/373,637, dated Apr. 26, 2017.
Notice of Allowance, U.S. Appl. No. 14/205,105, dated Jun. 1, 2017.
Notice of Allowance, U.S. Appl. No. 14/344,311, dated Aug. 30, 2017.
Notice of Allowance, U.S. Appl. No. 14/372,989, dated Aug. 10, 2016.
Response to Final Office Action and Advisory Action, U.S. Appl. No. 15/373,637, dated Feb. 12, 2018.
Response to Final Office Action, U.S. Appl. No. 14/372,989, dated Jul. 29, 2016.
Response to Final Office Action, U.S. Appl. No. 15/373,637, dated Jan. 10, 2018.
Response to Non-Final Office Action, U.S. Appl. No. 14/895,843, dated Sep. 22, 2016.
Response to Non-Final Office Action, U.S. Appl. No. 15/373,637, dated Jul. 26, 2017.

(56) References Cited

OTHER PUBLICATIONS

Response to Non-Final Office Action, U.S. Appl. No. 15/373,637, dated Aug. 14, 2018.
Response to Restriction Requirement, U.S. Appl. No. 14/205,105, dated Mar. 1, 2017.
Response to Restriction Requirement, U.S. Appl. No. 14/344,311, dated May 26, 2017.
Restriction Requirement, U.S. Appl. No. 14/205,105, dated Dec. 1, 2016.
Restriction Requirement, U.S. Appl. No. 14/344,311, dated Mar. 29, 2017.
International Search Report and Written Opinion, PCT/US2012/055551, dated Feb. 26, 2013, 12 pages.

\* cited by examiner

SYSTEM AND METHOD FOR TREATING ANIMALS

CROSS-REFERENCE TO RELATED APPLICATIONS

The present application claims priority to U.S. Provisional Patent Application No. 61/535,225, which is entitled Systems and Methods for Preventing and/or Treating Peripheral Neuropathy and Peripheral Vascular Disease, and was filed Sep. 15, 2011.

This application also claims priority to U.S. Provisional Patent Application No. 61/616,989, filed Mar. 28, 2012, and entitled System and Method for Treating Animals. The contents of all of the above-mentioned patent applications are hereby incorporated by reference in their entireties.

FIELD OF THE INVENTION

Aspects of the present invention relate to systems and methods related to veterinarian medicine. More specifically, the present invention relates to medical systems and methods for treating soft tissues of an animal patient to promote tissue health, healing and increased performance.

BACKGROUND OF THE INVENTION

Animals are subject to many of the same musculoskeletal, circulatory and neurological problems that affect humans. For example, animals can suffer from problems associated with aging or competitive based injuries. Examples of health issues faced by animals include Osteoarthritis, urethral urolithiasis in the horse, tendon injuries, bicipital tenosynovitis, intestinal anastomosis, ischemic tissue survival (pre surgical), increasing osteoblastic development, increasing ROM, enhanced healing of chronic bone infections, regeneration of periodontal tissues following periodontal disease, increasing stimulation of osteogenesis in the bone-ligament interface, increase in collagen production, acceleration of tendon rupture healing, aiding peripheral nerve regeneration and pain reduction.

Animals often have unique physiological characteristics as compared to other animals and, of course, humans. Accordingly, it would be advantageous to be able to tailor the medical treatment of an animal to its specific physiological characteristics to facilitate the best possible outcome from the medical treatment. This is especially important in treating animals as an animal is often not able to understand that it is ill or injured and take appropriate steps on its own (e.g., unlike a human who might understand the benefit of, and be able to, undergo bed rest or stay off of an injured limb). Accordingly, anything that can be done to speed the recovery of an illness or injury is especially useful in the context of veterinarian medicine.

A need exists for a system and method of non-invasively treating tissues of an animal, where the treating of the tissue may be tailored for the unique physiological needs of the animal and administered in a standardized manner using standardized diagnostic criteria. In addition, a need exists for a system and method of assessing the efficacy of a tissue treatment in a standardized and non-biased manner.

BRIEF SUMMARY OF THE INVENTION

The disclosed multi-application device or system provides a method of applying both measured percussive mechanical and RF forces into animal tissues. These forces are designed to aid the healing process from either aging or competitive based injuries such as Osteoarthritis, urethral urolithiasis in the horse, tendon injuries, bicipital tenosynovitis, intestinal anastomosis, ischemic tissue survival (pre surgical), increasing osteoblastic development, increasing ROM, enhanced healing of chronic bone infections, regeneration of periodontal tissues following periodontal disease, increasing stimulation of osteogenesis in the bone-ligament interface, increase in collagen production, acceleration of tendon rupture healing, aiding peripheral nerve regeneration and pain reduction.

A system is provided for treating a tissue of an animal patient. In one embodiment, the system includes a display and input device, and at least one instrument chosen from an impulse stimulator instrument and an acoustic oscillator. The impulse stimulator is configured to apply a percussive massage comprising one or more force impulses. The impulse stimulator is further configured to measure a response of the tissue to one of the applied force impulses to assess a condition of the tissue. The acoustic oscillator is configured to apply an acoustic stimulation comprising one or more acoustic pulses to the tissue of the animal patient.

In this embodiment, the system also includes at least one processor and a database. The database may include at least one stored treatment protocol, stored patient data, and at least one measurement-correlated instrument control setting. The stored patient data may include at least one patient-specific treatment protocol.

The treatment application may implement one or more treatments to the tissue according to one or more selected treatment protocols by operating one of the instruments using a graphical display to guide an operator of the system through the treatment of the one or more anatomical landmarks. The one or more treatments are chosen from a neural treatment, a muscular treatment, and a circulatory treatment. The neural treatment includes applying one or more percussive massages to one or more anatomical landmarks associated with nerves. The muscular treatment includes applying one or more percussive massages to one or more anatomical landmarks associated with muscles, ligaments and/or tendons. The circulatory treatment includes applying one or more acoustic stimulations to one or more anatomical landmarks associated with circulatory vessels.

Also a method is provided for treating a tissue of an animal patient. In one embodiment, the method includes selecting a treatment protocol that includes one or more instrument control settings as well as one or more anatomical landmarks to be treated.

The method in this embodiment further includes implementing one or more treatments to the tissue according to one or more selected treatment protocols by operating at least one instrument by using a graphical display to guide an operator through the treatment of the one or more landmarks. The at least one instrument may be chosen from an impulse stimulator instrument and an acoustic oscillator.

The one or more treatments implemented by the method in this embodiment include a neural treatment, a muscular treatment, and a circulatory treatment. The neural treatment includes administering one or more percussive massages to one or more anatomical landmarks associated with nerves. The muscular treatment includes administering one or more percussive massages to one or more anatomical landmarks associated with muscles, ligaments and/or tendons. The circulatory treatment includes administering one or more acoustic stimulations to one or more anatomical landmarks associated with circulatory vessels.

Further a second embodiment of a system is provided for treating a tissue of an animal patient, including memory, at least one instrument, and a plurality of modules executing on at least one processor. The memory includes at least one stored treatment protocol, stored patient data, and at least one measurement-correlated instrument control setting. The stored patient data includes at least one patient-specific treatment protocol.

The at least one instrument may include an impulse stimulator instrument to apply a percussive massage comprising one or more force impulses to the tissue. The impulse stimulator instrument also measures a response of the tissue to one of the applied force impulses to assess a condition of the tissue. The at least one instrument may also include an acoustic oscillator to apply an acoustic stimulation comprising one or more acoustic pulses to the tissue.

The plurality of modules includes a treatment protocol selection module, a neural treatment module, a muscular treatment module, and a circulatory treatment module. The treatment protocol selection module selects one or more treatment protocols based on at least one of: the stored patient data, an analysis of the condition of the tissues, one or more of the stored treatment protocols, one or more of the stored patient-specific treatment protocols, and a treatment protocol specified by the operator. The neural treatment module implements a neural treatment comprising one or more percussive massages to one or more anatomical landmarks associated with nerves. The muscular treatment module implements a muscular treatment comprising one or more percussive massages to one or more anatomical landmarks associated with muscles, ligaments and/or tendons. The circulatory treatment module implements a circulatory treatment comprising one or more acoustic stimulations to one or more anatomical landmarks associated with circulatory vessels.

A system is provided for treating tissue of an animal patient for at least one of improving tissue health, facilitating healing, or improving animal performance. In one embodiment the system includes a display, an input, a CPU, a memory, a first RF head, a RF receiver antenna, a plurality of second RF heads, and an EMG sensor. The display includes a LCD or other type of screen and is configured to display information associated with the treatment of the tissue. The input is in electrical communication with the display and includes a key board, touch screen, or other type of input mechanism. The input is configured to receive information associated with the treatment of the tissue. The CPU is in electrical communication with the input. The memory is in electrical communication with the CPU and includes treatment parameters associated with the treatment of the tissue. The first RF head is capable of being placed in electrical communication with the CPU and includes an array of piezoelectric transducers. The array is configured to generate RF over a range of frequencies not possible via a single piezoelectric transducer. The RF receiver antenna is capable of being placed in electrical communication with the CPU and is configured to detect RF energy transmitted through the tissue from the first RF head. For the plurality of second RF heads, each second RF head has a piezoelectric transducer tuned to a unique frequency and is capable of being placed in electrical communication with the CPU. The EMG sensor is capable of being placed in electrical communication with the CPU and is configured to detect electromyogram in the tissue. When the first RF head and RF receiver antenna are applied to the tissue, the system is configured to: a) cause the first RF head to administer RF energy to the tissue over a range of RF frequencies; b) cause the RF receiver antenna to sense the administered RF energy transmitted through the tissue; c) identify which RF frequency of the range of RF frequencies administered to the tissue has the most transmissitivity through the tissue; and d) recommend a second RF head of the plurality of RF heads that is capable of providing the identified RF frequency. When the recommended second RF head and EMG sensor are applied to the tissue, the system is configured to: a) cause the recommended second RF head to administer RF energy at the identified RF frequency to the tissue over a range of pulse frequencies; b) cause the EMG sensor to detect electromyogram in the tissue arising due to the RF energy administered to the tissue over the range of pulse frequencies; c) identify which pulse frequency of the range of pulse frequencies administered to the tissue causes the highest electromyogram readings in the tissue; and d) treat the tissue with the recommended second RF head at the identified RF frequency at the identified pulse frequency.

Depending on the version of the embodiment of the system, the array is configured to generate RF over a range of between approximately 500 KHz and approximately 1.5 MHz at, for example, steps of between approximately 50 KHz and approximately 200 KHz.

In one version of the embodiment of the system, the piezoelectric transducers of the array include a first piezoelectric transducer, a second piezoelectric transducer, and a third piezoelectric transducer, where each of the first, second and third piezoelectric transducers generate RF at distinct frequencies from each other. In one version of the embodiment of the system, the plurality of second RF heads includes individual second RF heads each tuned to a unique frequency from each other and each unique frequency is between approximately 500 KHz and approximately 1.5 MHz.

In one version of the embodiment of the system, when the recommended second RF head is caused to administer RF energy at the identified RF frequency to the patient over a range of pulse frequencies, the range of pulse frequencies is between approximately 1 Hz and approximately 300 Hz. In one version of the embodiment of the system, the recommended second RF head is caused to administer RF energy at the identified RF frequency to the patient over the pulse frequency range of between approximately 500 KHz and approximately 1.5 MHz at steps programmatically controlled and optimized for tissue type via stored protocols.

In one version of the embodiment of the system, the system further includes an impulse head capable of being placed in electrical communication with the CPU and including a solenoid driven anvil configured to deliver mechanical impulse energy to the tissue. The impulse head further includes a transducer sensor for detecting a wave generated in the tissue via the administration of the mechanical impulse energy to the tissue.

Also a method is provided for treating tissue of an animal patient for at least one of improving tissue health, facilitating healing, or improving animal performance. In one embodiment, the method includes: administering RF energy to the tissue over a range of RF frequencies; detecting the administered RF energy; identifying which RF frequency of the range of RF frequencies has the greatest transmissibility through the tissue; recommending the identified RF frequency for use in further RF energy treatment to the tissue; administering the RF energy at the identified RF frequency to the tissue over a range of pulse frequencies; identifying which pulse frequency of the range of pulse frequencies results in the highest electromyogram readings in the tissue; recommending the identified pulse frequency for use in further RF energy treatment to the tissue; and administering the RF energy at the identified RF frequency and identified pulse frequency to the tissue.

In one version of the embodiment of the method, the administration of the RF energy to the tissue over the range of frequencies is accomplished via a RF head having an array of piezoelectric transducers each tuned to an individual unique frequency, the array being configured to generate RF over a range of between approximately 500 KHz and approximately 1.5 MHz.

In one version of the embodiment of the method, the administration of the RF energy to the tissue over the range of frequencies is over a range of between approximately 500 KHz and approximately 1.5 MHz at steps of between approximately 50 KHz and approximately 200 KHz.

In one version of the embodiment of the method, the recommending the identified RF frequency for use in further RF energy treatment to the tissue includes identifying a specific RF head from a plurality of RF heads that is configured to provide the recommended RF frequency.

In one version of the embodiment of the method, the administering the RF energy at the identified RF frequency to the tissue over a range of pulse frequencies occurs over pulse frequencies ranging between approximately 1 Hz and approximately 300 Hz programmatically controlled and optimized for tissue type via stored protocols.

In one version of the embodiment of the method, the administering the RF energy at the identified RF frequency to the tissue over a range of pulse frequencies occurs over pulse frequencies ranging between approximately 1 Hz and approximately 30 Hz.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

A veterinarian system and method are provided for assessing and treating the tissues of an animal patient including, but not limited to: nerves, muscles, connective tissues, and circulatory vessels. In an aspect, the system is configured to provide one or more treatments to the tissues of the animal patient in the form of: percussive massage, acoustic stimulation, and any combination thereof. In other aspects, the system may be further configured to obtain one or more assessments of the condition of the tissues before and/or after one or more treatments, and to store these assessments in a database. These stored assessments may be used in an aspect to assess the efficacy of one of one or more treatments, to monitor changes in the tissues over time, and to inform the selection of subsequent treatments. In various embodiments of the system, a treatment may be selected using one or more methods including, but not limited to: selecting a treatment from a predefined menu of treatment protocols, determining a treatment based on an analysis of the condition of the tissues of the animal patient, selecting a treatment from a predefined menu of patient-specific treatment protocols, or specifying a user-defined protocol for a treatment.

In one aspect, the veterinarian treatment system may be used to maintain and/or enhance tissue health, facilitate tissue healing, or improve performance of an animal patient. The veterinarian system and method may be utilized for a variety of animal patients including, but not limited to, livestock such as horses, cattle, etc., exotic animals such as lions, elephants, etc., aquatic animals such as whales, dolphins, etc., and pets including dogs, cats, etc. In some embodiments, the veterinarian system and method may be specifically configured for use with a specific type of animal. For example, the system may have diagnostic and treatment protocols and hardware specifically adapted for use with horses, dogs or other specific animals.

Aspects of the veterinarian treatment system described provide standardized and repeatable treatment protocols for the tissues of an animal patient, and further provide the ability to obtain and store information related to the condition of the tissues before, during, and after a treatment. This information allows the operator to monitor the efficacy of the treatment both immediately after the treatment, as well as after the passage of time between treatments; this information may further inform the selection of a treatment protocol and/or dynamically adjust the protocol during the administration of a treatment.

Detailed descriptions of embodiments of the veterinarian treatment system, devices included in the treatment system, and methods of using the treatment system are provided below.

I. Veterinarian Treatment System

Figure 1:
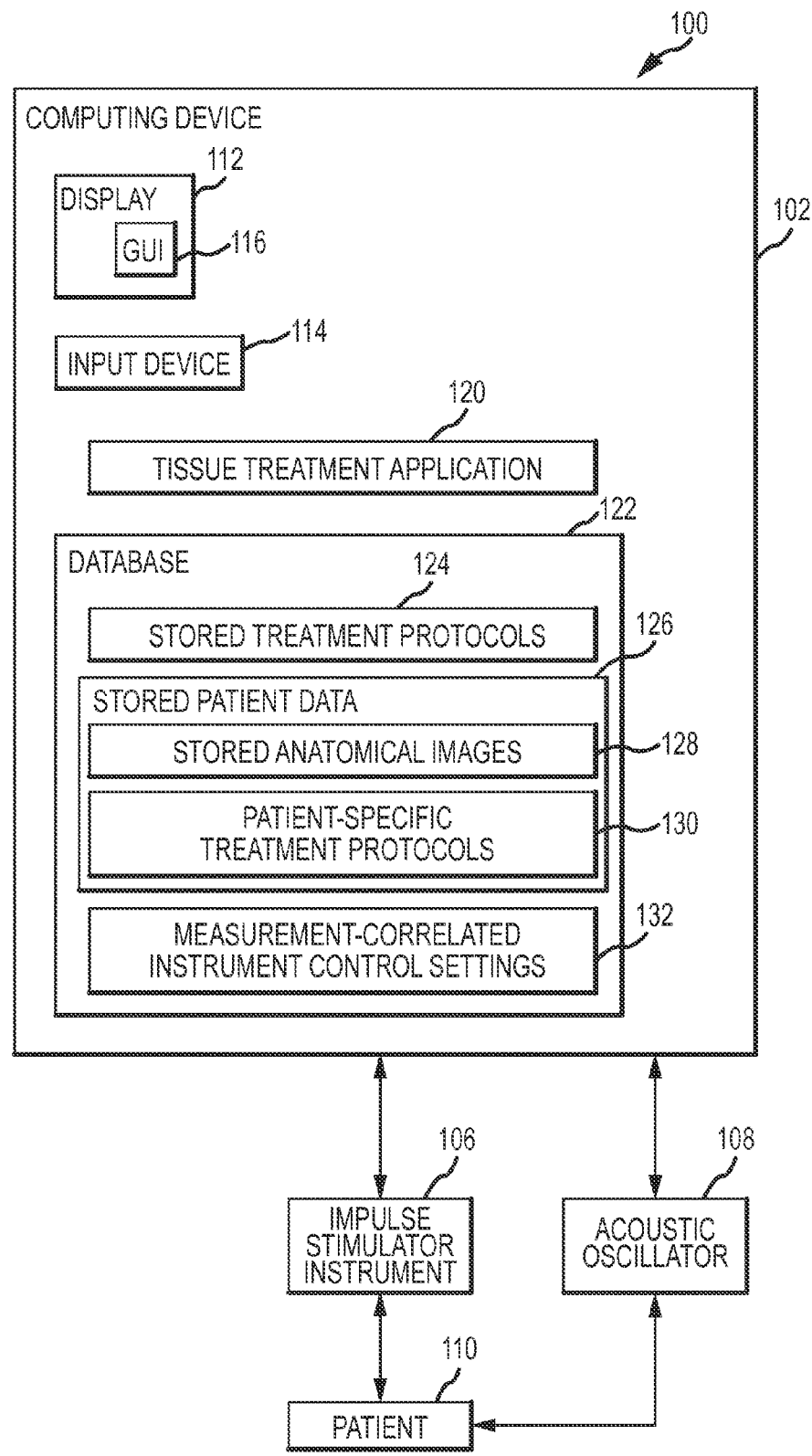
FIG. 1 is a block diagram of a veterinarian treatment system for treating the tissue of an animal patient.

The elements of a veterinarian treatment system 100 are depicted in FIG. 1. The system 100 includes a computing device 102, an impulse stimulator instrument 106, and an acoustic (RF) oscillator 108. Non-limiting examples of a suitable computing device include a laptop computer, a personal digital assistant, a tablet computer, a standard personal computer, or any other known processing device. The computing device 102 includes one or more processors and memory configured to send, receive, and process data and/or communications from an operator of the system 100, the impulse stimulator instrument 106, and the acoustic oscillator 108 in order to assess the condition of the tissues of an animal patient 110, select a treatment protocol, and implement a treatment of the tissues of the patient 110.

The impulse stimulator instrument 106 is configured to deliver a plurality of percussive shock waves to the tissues of the patient 110 during the course of a treatment. The impulse stimulator instrument 106 is further configured to measure characteristics of the tissue of the patient 110, such as tissue reactive force during the application of a percussive shock wave. The acoustic oscillator 108 is configured to deliver acoustic pulses to the tissues of a patient during the course of a treatment. The impulse stimulator instrument 106 and the acoustic oscillator 108 are further configured to receive data and/or communications from the computing device 102 in order to operate the devices in a coordinated manner during the implementation of a treatment by the system 100.

The computing device 102 includes a display 112 configured to display data and/or graphical user interfaces (GUIs) 116 to the operator. Non-limiting examples of devices suitable for use as a display 112 include a computer monitor and a touch screen. The computing device 102 may further include an input device 114 including, but not limited to, a keyboard and/or a pointing device such as a mouse, a trackball, a pen, or a touch screen. The input device 114 is configured to enter data into or interact with the GUIs 116 used to implement the operation of the system 100. In an embodiment, the display 112 and input device 114 may be a single integrated device, such as a touch screen. The GUI 116 enables the operator of the system 100 to interact with menus and other data entry forms used to control the operation of the system 100.

The computing device 102 further includes a tissue treatment application 120 configured to receive and process data and/or communications, as well as produce and send data and/or communications used to perform the functions of the system 100 described above, and in detail below. The data and/or communications produced by the tissue treatment application 120 may be sent to the display 112 in order to guide the operator of the system 100 through the functions of the system 100. In addition, the data and/or communications may be sent to the impulse stimulator instrument 106, and/or acoustic oscillator 108 in order to operate these devices in a coordinated manner during the operation of the system 100.

The computing device 102 further includes a database 122 configured to store a plurality of stored treatment protocols 124, stored patient data 126, and measurement-correlated instrument control settings 132. The stored treatment protocols 124 may include data utilized during the implementation of one or more treatments to the patient 110 using the system 100. For example, one of the stored treatment protocols 124 may include parameters used for the implementation of a treatment such as the location of the treatment on the tissues of the patient 110 and instrument operating parameters such as a power setting or duration of instrument operation. The stored patient data 126 may include patient-specific information used to monitor the condition of the tissue of the patient 110 over time, to maintain a record of previous treatments performed by the system 100, to provide a schedule of future treatments, and to perform a customized treatment on a particular patient 110 using the system 100. The stored patient data 126 may include patient-specific treatment protocols 130 that may include parameters used for the implementation of a treatment that are customized for the treatment of a particular patient 110 based on a previous assessment of the condition of the tissues of the patient 110 and/or previous treatments performed on a particular patient 110 using the system 100.

II. Tissue Treatment Application

Figure 2:
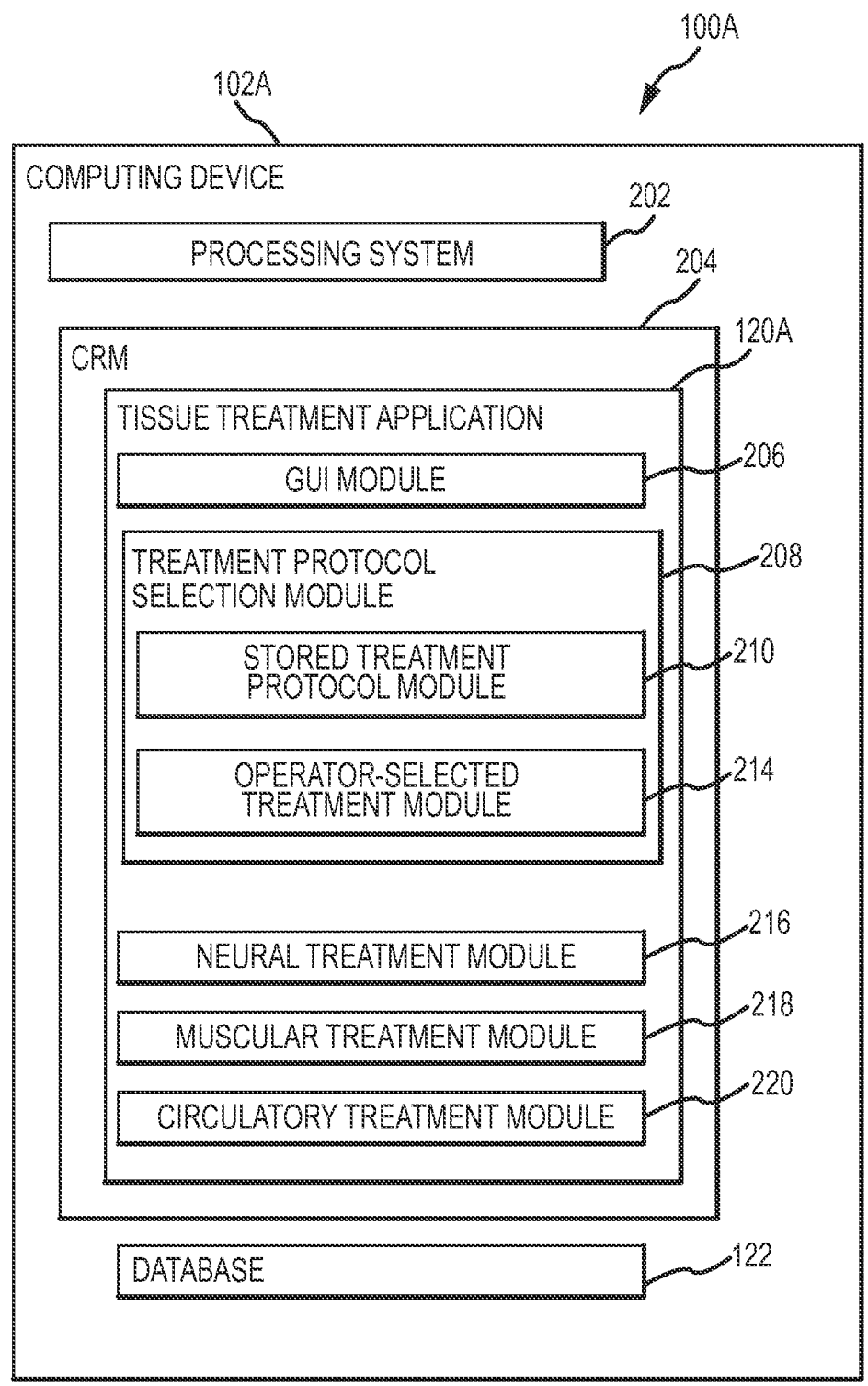
FIG. 2 is a block diagram of an animal treatment application configured to operate on a computing device.

FIG. 2 is a block diagram depicting a tissue treatment application 120A executing on a computing device 102A. According to one aspect, the computing device 102A includes a processing system 202 that includes one or more processors or other processing devices. The processing system 202 executes the tissue treatment application 120A to select and provide a treatment of the tissues of a patient 110 (not shown) using the impulse stimulator instrument 106 (not shown) and/or acoustic oscillator 108 (not shown). A database 122 may be accessed by the tissue treatment application 120A during execution to provide information including, but not limited to: stored patient information, stored treatment protocols, and stored instrument control settings.

In an aspect, the computing device 102A includes a computer readable medium ("CRM") 204 configured with the tissue treatment application 120A. The tissue treatment application 120A includes instructions or modules that are executable by the processing system 202 to enable a user to implement a treatment to the tissues of a patient 110.

The CRM 204 may include volatile media, nonvolatile media, removable media, non-removable media, and/or another available medium that can be accessed by the computing device 102A. By way of example and not limitation, computer readable medium 204 comprises computer storage media and communication media. Computer storage media includes nontransient memory, volatile media, nonvolatile media, removable media, and/or non-removable media implemented in a method or technology for storage of information, such as computer readable instructions, data structures, program modules, or other data. Communication media may embody computer readable instructions, data structures, program modules, or other data and include an information delivery media or system.

A GUI module 206 transmits one or more GUIs 116 (not shown) to the display 112 (not shown). As described above, the operator of the system 100 interacts with one or more GUIs received from the computing device 102A to review treatment protocols, enter data and make menu selections used to implement a treatment using the system 100. Examples of screen shots of the one or more GUIs 116 in various aspects are provided below.

In an aspect, the tissue treatment application 120A includes a treatment protocol selection module 208 for selecting an appropriate treatment protocol based on stored patient data, analysis of the patient's tissues, selection from a stored menu of treatment protocols, and/or specification of a treatment protocol by the operator of the system 100. The tissue treatment application 120A may further include modules to implement a particular treatment on the tissues of a patient, including a neural treatment module 216, a muscular treatment module 218, and a circulatory treatment module 220. Detailed descriptions of each of the modules of the tissue treatment application 120A are provided below.

III. Treatment Protocol Selection Module

The treatment protocol selection module 208 selects one or more treatment protocols to be performed on the tissues of a patient 110. The one or more treatment protocols may be selected from a stored menu of treatment protocols, a treatment protocol may be determined based on an assessment of the condition of the patient's tissues, or a treatment protocol may be specified by the operator of the system 100A. The treatment protocol selection module 208 in an embodiment may include a stored treatment protocol module 210, and an operator-selected treatment module 214.

a. Stored Treatment Protocol Module

Figure 3:
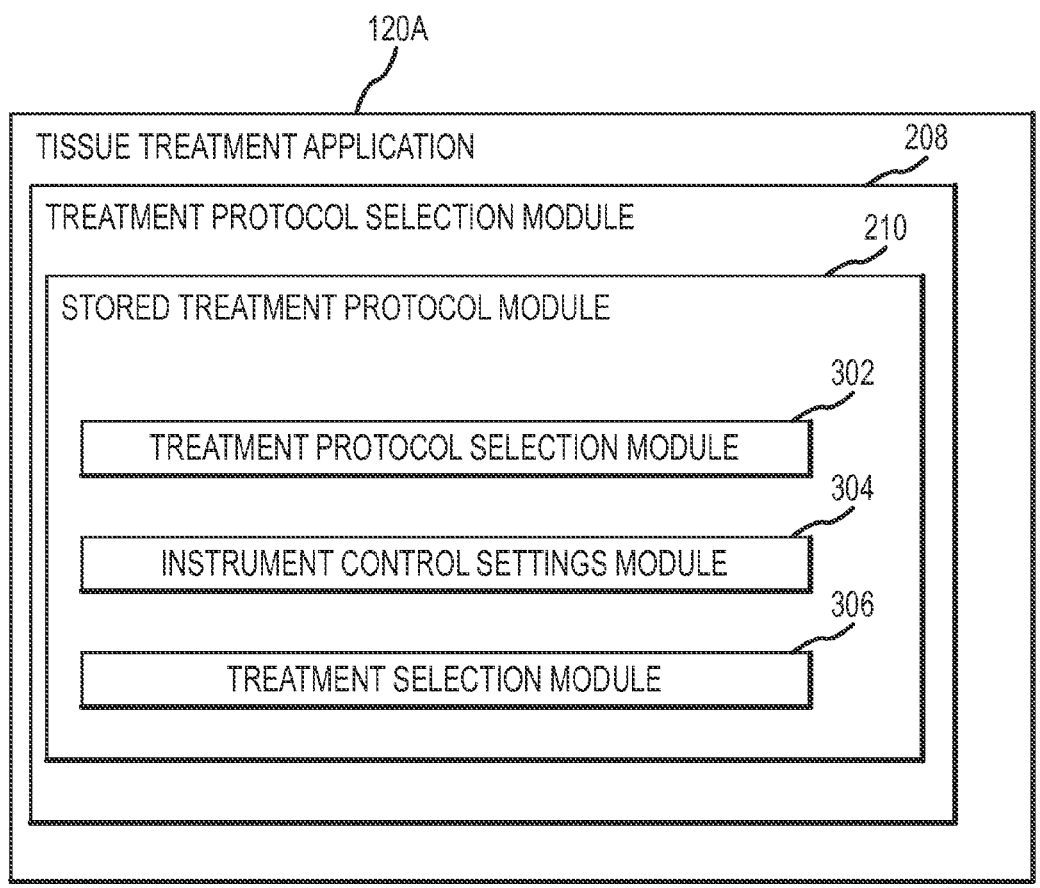
FIG. 3 is a block diagram of a stored treatment protocol selection module of an animal treatment application.

The stored treatment protocol module 210 is configured to generate a menu of treatment protocols from which the operator may select a treatment for the tissues of the patient, as well as to implement the treatment protocol selected from the menu by the operator. In an embodiment, illustrated in FIG. 3, the stored treatment protocol module 210 may include a treatment protocol selection module 302, an instrument control settings module 304, and a treatment selection module 306. The treatment protocol selection module 302 generates a menu of treatment protocols and displays this menu to the operator via the GUI 116 (not shown). The menu of treatment protocols may be a list of standard treatments arranged into one or more organizational schemes including, but not limited to: region of patient body, type of patient tissue, type of tissue disorder, treatments previously performed on the patient, desired results of a tissue treatment, and a schedule of planned treatments for a patient. In an embodiment, the stored treatment protocol module 210 may access stored patient information from the database 122 (not shown) in order to generate the menu of patient-specific treatment protocols. For example, the stored treatment protocol module 210 may retrieve one or more patient-specific treatment protocols 130 from the database 122, shown on FIG. 1, for use in the menu of treatment protocols.

Referring back to FIG. 3, the stored treatment protocol module 208 may further include an instrument control settings module 304 configured to determine the appropriate settings for one or more instruments used to implement a treatment protocol selected by the operator from the menu of treatment protocols using the treatment protocol selection module 302. As illustrated in FIG. 1, the system 100 may administer treatments with one or more instruments including, but not limited to, an impulse stimulator instrument 106 and an acoustic oscillator 108. In an embodiment, the instrument control settings module 304 may determine one or control settings for the impulse stimulator instrument 106 including, but not limited to, preload tissue compression force, magnitude and frequency of a percussive impact to be applied to the tissue. In another embodiment, the instrument control settings module 304 may determine one or control settings for the acoustic oscillator 108 including, but not limited to: magnitude and frequency of an acoustic pulse to be applied to the tissue. A more detailed description of additional instrument control settings that may be determined by the instrument control settings module 304 are provided below.

The stored treatment protocol module 208 may further include a treatment selection module 306. Once the treatment protocol has been determined by the treatment protocol selection module 302 and the instrument control settings have been initialized by the instrument control settings module 304, the treatment selection module 306 may initiate the execution of one or more of the treatment modules used to implement a treatment on a muscular tissue, a nerve, and/or a circulatory vessel.

Figure 4:
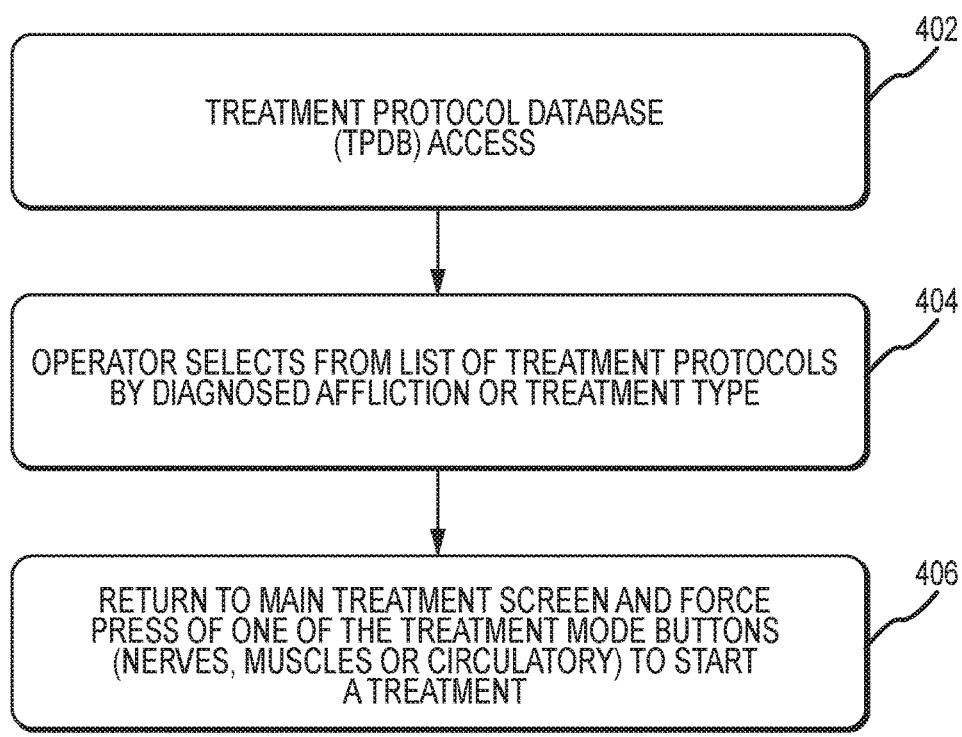
FIG. 4 is a flow chart illustrating an embodiment of a stored treatment protocol selection module.

FIG. 4 is a flow chart illustrating a series of actions taken by the operator of the system in an embodiment of the stored treatment protocol module 208. In this embodiment, the operator of the system makes a selection to access the stored treatment protocol database at step 402. The operator then selects a desired treatment protocol from the displayed list of stored treatment protocols at step 404. Once a treatment protocol has been selected, the operator then selects one of the treatment modules for execution at step 406. At step 406, the treatment modules available for execution are limited by the stored treatment protocol module 208 to include only those treatment modules that are appropriate for the selected treatment protocol.

b. Tissue Assessment Module

Referring back to FIG. 2, the tissue treatment application 120 further includes a tissue assessment module 212 configured to assess the condition of the tissues of the patient and determine a recommended treatment protocol based on the assessed condition of the tissues. The tissue assessment module 212 may analyze one or more types of information regarding the tissue in order to assess the need for treatment and determine the appropriate type of treatment.

Figure 5:
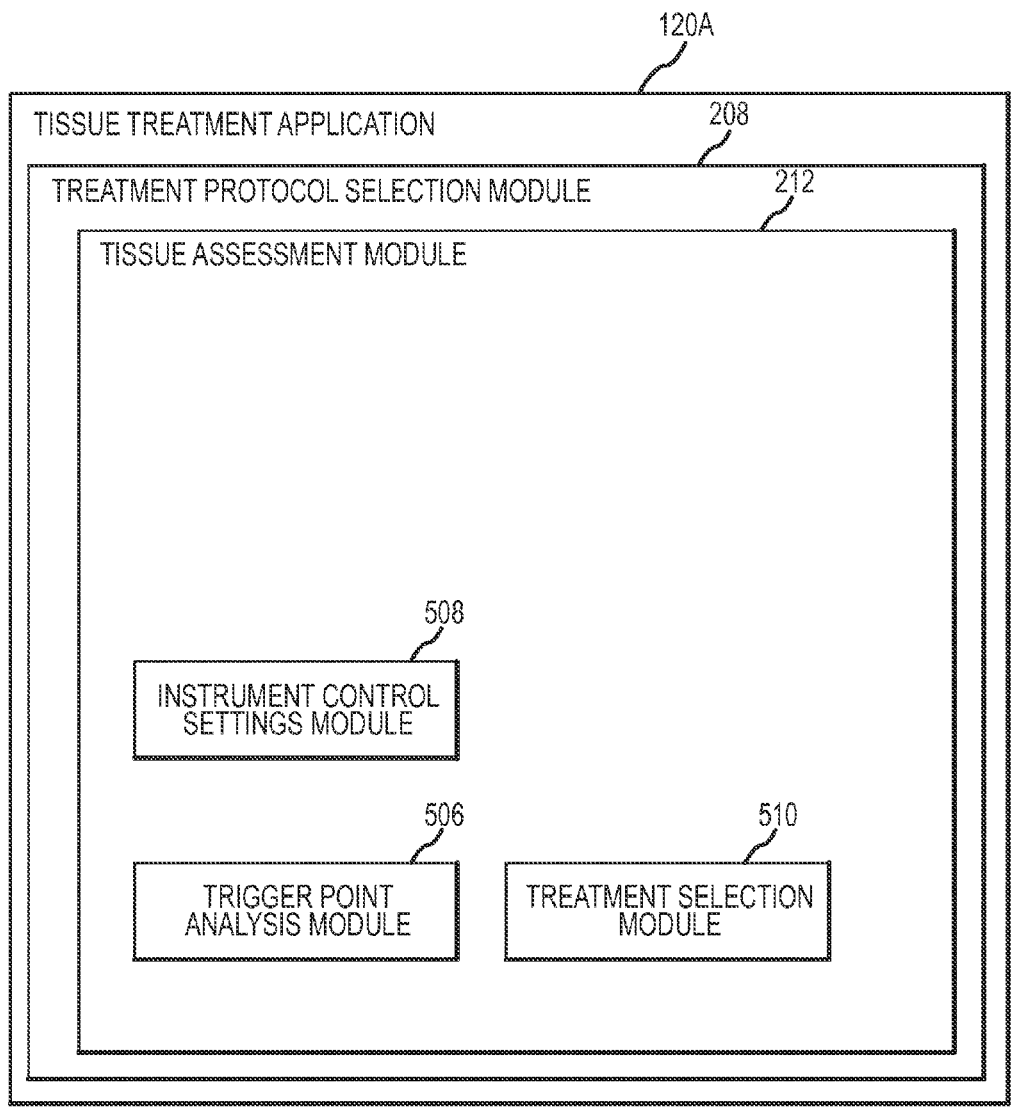
FIG. 5 is a block diagram of a tissue assessment module of a tissue treatment application.

FIG. 5 is a block diagram illustrating an embodiment of the tissue assessment module 212. In this embodiment, the tissue assessment module 212 may include a trigger point analysis module 506, which may implement assessment of selected tissues identified via visual or tactile inspection or via use of the impulse stimulator instrument 106 and/or the acoustic oscillator 108. Once a recommended treatment protocol has been identified, the instrument control settings module 508 provides the appropriate instrument control settings and the treatment selection module 510 directs the initiation of one or more treatment protocols. Any associated patient data and/or treatment protocol information may be stored in the database 206 (not shown) by the trigger point analysis module 506.

The trigger point analysis module 506 may assess the condition of the tissues of the patient by measuring tissue characteristics including, but not limited to, the response of the tissue to an applied force impulse, or any other aspect of the tissue related to, or correlated with, the health and condition of the tissue. The trigger point analysis module 506 may use any known instrument to perform an additional assessment of the condition of the tissues including, but not limited to, an impulse stimulator instrument as described below, an electromyographic electrode, or any other known measurement device appropriate for measurement of a tissue characteristic.

Figure 6:
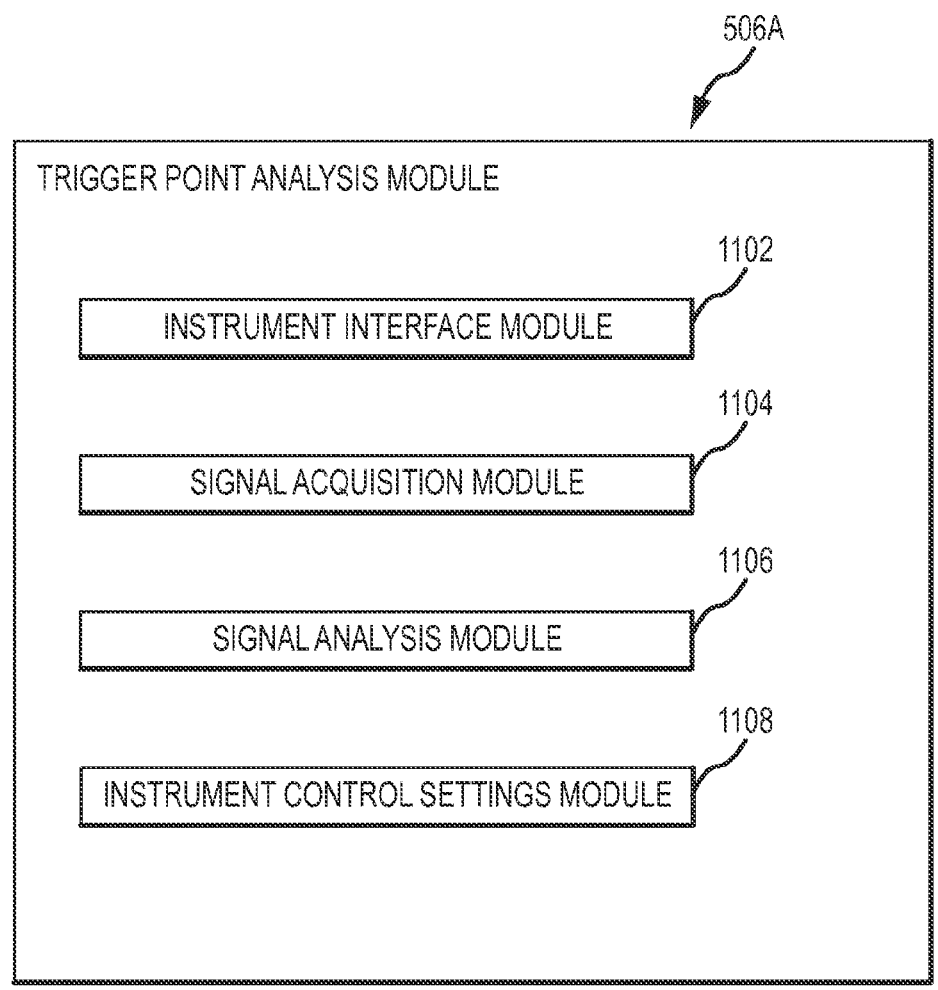
FIG. 6 is a block diagram of a trigger point analysis module.

FIG. 6 is a block diagram illustrating an embodiment of a trigger point analysis module 506A. The trigger point analysis module 506A includes an instrument interface module 1102 to provide a GUI or other interface used by the operator to conduct measurements using one or more devices, a signal acquisition module 1104 to record a measurement signal obtained by the one or more devices, a signal analysis module 1106 to process the signal from the device to determine the condition of the tissue, and an instrument control settings module 1108 to provide instrument control settings such as power settings, frequency of percussive impacts, frequency of applied acoustic pulses, and any other parameter associated with a selected treatment protocol.

The trigger point analysis module 506A may be configured to guide the operator through the steps of locating a landmark, initializing an instrument for measuring a characteristic of a tissue in the vicinity of the landmark, and obtaining one or more measurements using the instrument. The operator may be guided through measurements for one or more landmarks using the trigger point analysis module 506A. The trigger point analysis module 506A may process the measurements of the characteristics of each landmark in combination with that landmark's degree of asymmetry to determine a recommended treatment protocol.

Figure 7:
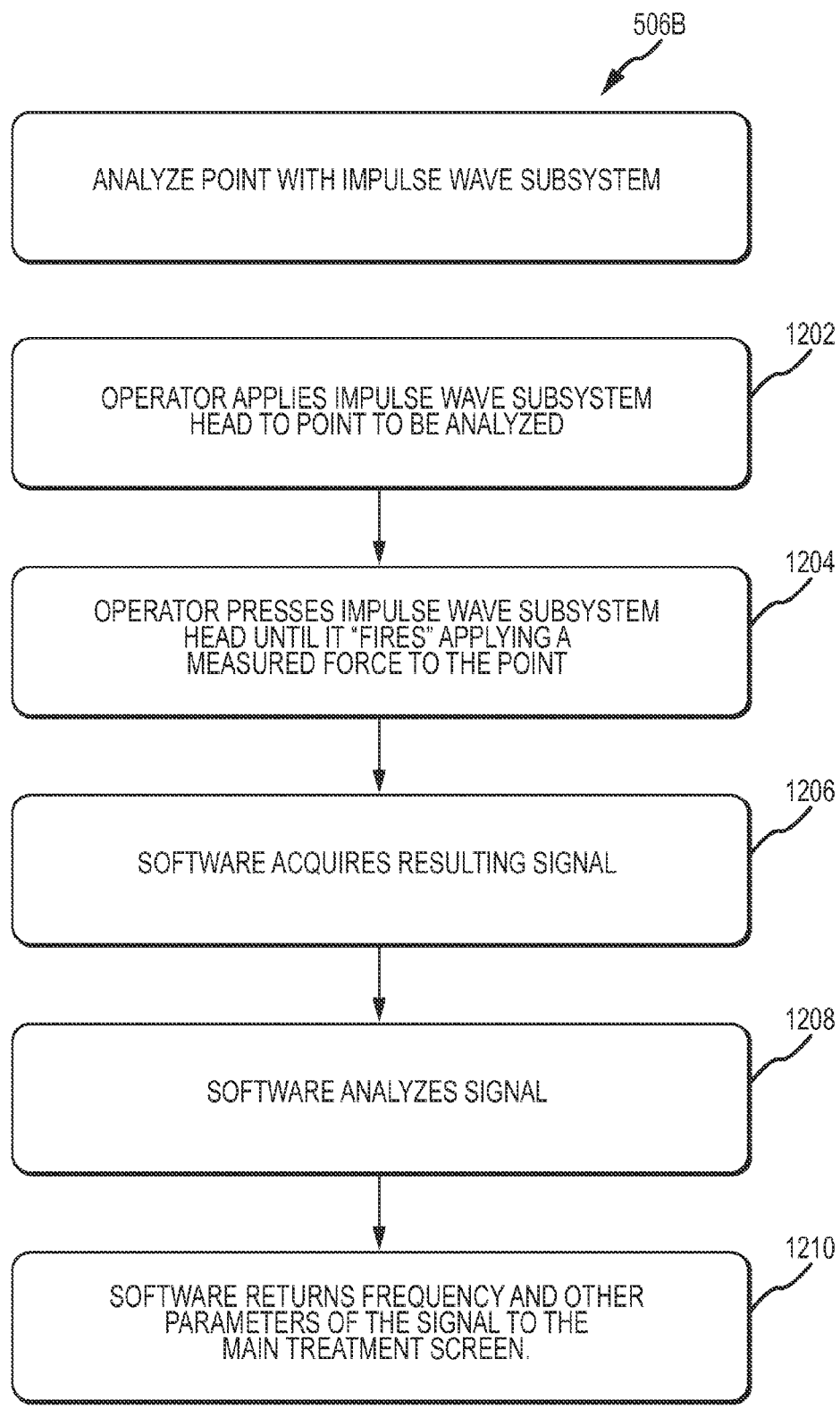
FIG. 7 is a flow chart illustrating an embodiment of a trigger point analysis module.

FIG. 7 is a flow chart illustrating an embodiment of a trigger point analysis module 506B. In this embodiment, an impulse stimulator instrument 106, referred to as an Impulse Wave subsystem in FIG. 7, is used to measure the reaction of a tissue to an applied force impulse. The impulse stimulator instrument 106 is situated at a specified anatomical landmark at step 1202. In an aspect, the specified anatomical landmark may be identified as a landmark associated with a nervous, muscular, and/or circulatory structure that may be the target of the treatment. The anatomical landmark to be subjected to trigger point analysis may be displayed to the operator of the system 100 via the display 112. A force impulse is applied to the tissue at step 1204 and a signal encoding the reaction of the tissue to the applied force impulse is acquired by the signal acquisition module 1104 at step 1206. The signal analysis module 1106 analyzes the signal at step 1208, and the instrument control settings are determined by the instrument control settings module 1108 at step 1210. The instrument control settings are used by one or more treatment modules 216-220 to provide a treatment to a tissue of the patient.

In an aspect, the signal analysis module 1106 may analyze any one or more characteristics of the tissue in response to the force impulse applied by the impulse treatment instrument 106 including, but not limited to, the waveform of the tissue response. Non-limiting aspects of the waveform of the tissue response that may be analyzed by the signal analysis module 1106 include the peak or maximum amplitude of the waveform, the peak time, the rise time, the fall time, the frequency, and the area under the wave. Peak time, as defined, refers to the time from the initiation of the waveform to the peak amplitude of the waveform. Rise time, as defined, refers to the time elapsed between a waveform amplitude of 10% and 90% of the peak amplitude as the amplitude is rising to the peak amplitude. Fall time, as defined, refers to the time elapsed between a waveform amplitude of 90% and 10% of the peak amplitude as the amplitude is falling from the peak amplitude.

Without being limited to any particular theory, there is complexity in the differing shapes of the waveforms associated with the response of the tissues to the force impulses. In an aspect, the signal analysis module 1106 may generate a mathematical representation of the waveform of a tissue response and may further manipulate and interpret the mathematical representation so as to define the amount of resistance, mobility, condition, and/or other characteristics of the tissue.

The signal analysis module 1106 is configured to analyze the relationship of all of the response factors associated with tissue treatment and measurement, namely the analysis of the waveforms as they relate to tissues in general. The relation to the stiffness characteristic (waveform peak), the hysteresis function (wave shape), and the frequency response provide valuable information regarding the state of the measured tissue.

In an aspect, the measured waveform may be sinusoidal and may be influenced by tissue properties including, but not limited, to tissue mobility or resistance to mobility, fascia tension, muscle tonicity, connective tissue resiliency or inertia, local edema and any combination thereof. Each such waveform may be characterized mathematically by determining the peak amplitude, peak time, rise time, fall time, and slew rate; these quantities may facilitate the calculation of frequency response and certain ratios used to mathematically define the waveform characteristics. By analyzing the mathematics of the waveform characteristics, the condition of the tissues may be assessed using previously determined relationships of waveform characteristics and tissue condition.

Figure 20:
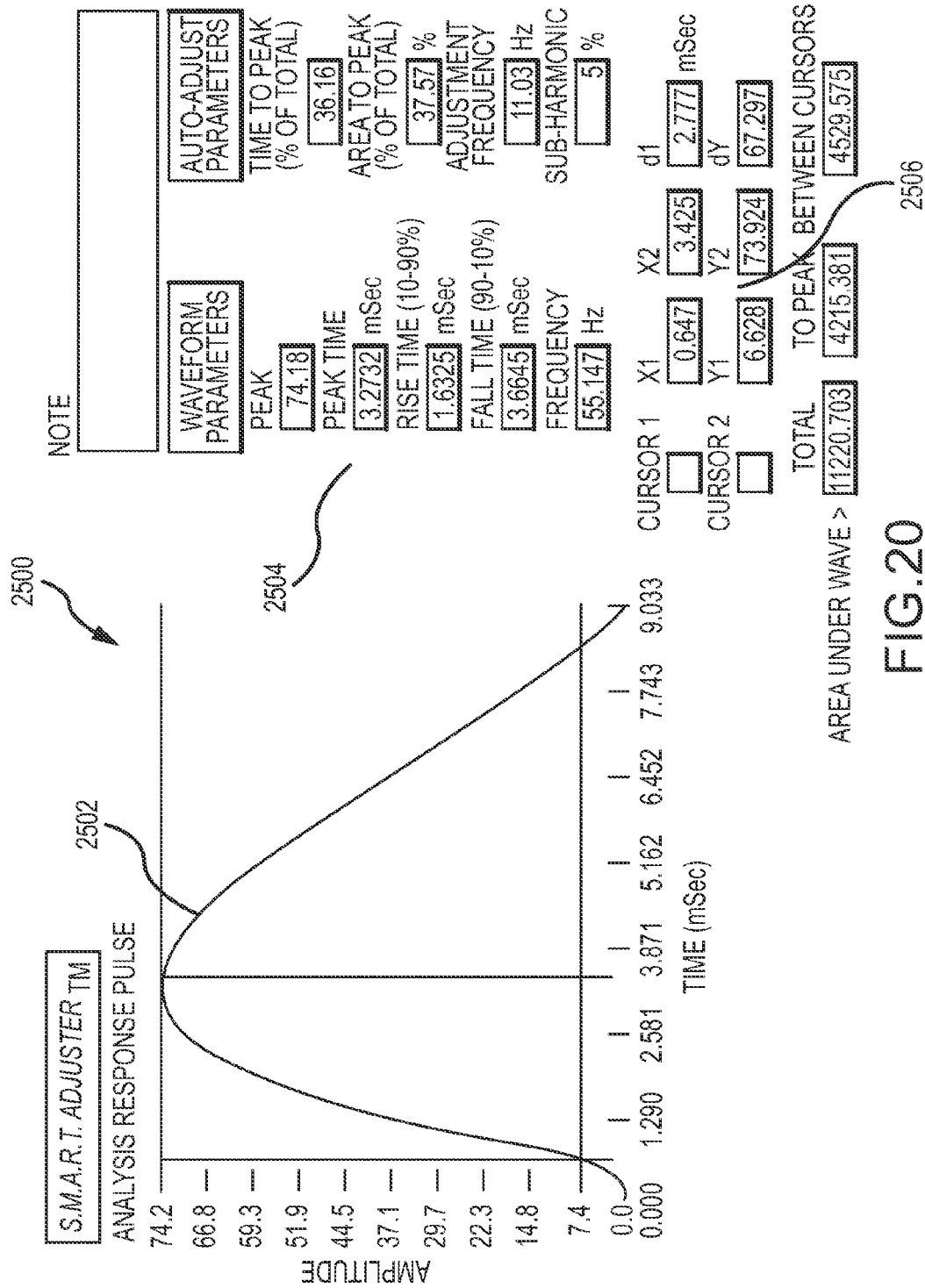
FIG. 20 shows a computer screen depicting a waveform and derived waveform data.

As the data are collected and logged and after all of the pertinent mathematic calculations are made, a summary display 2500 of the waveform and analysis may be presented on the display 112 as illustrated in FIG. 20. The summary display 2500 may include a graphic display of the waveform 2502, and the pertinent data 2504 and derived ratios 2506 may be displayed for assessment by the operator during a trigger point analysis. The data associated with the summary display 2500 may be stored in the database 122 for use by the tissue treatment application 120 in determining the appropriate treatment protocol and associated instrument control settings. In addition, the stored data associated with a trigger point analysis may be incorporated into a more comprehensive database used to develop and refine predictive diagnoses using methods of analysis including, but not limited to, clinical assumptions and statistical models. Normal values associated with the waveform analysis of healthy tissues may be compiled, stored, and used to compare normal versus aberrant tissues. Stored data may also be used to compare pre-treatment and post-treatment tissues.

i. Instrument Control Settings Module

Referring to FIG. 5, the tissue assessment module 212 may further include an instrument control settings module 508 configured to determine the control settings for the instruments to be used to administer a treatment to the tissues of the patient. The control settings may be determined based on tissue readings taken via the system and via physical inspection guided by veterinarian experience, as well as any additional characteristics of the tissues determined by the trigger point analysis module 506. In an embodiment, the instrument control settings module 508 may determine one or more control settings for the impulse stimulator instrument 106 including, but not limited to preload tissue compression force, magnitude and frequency of a force impulse to be applied to the tissue. In another embodiment, the instrument control settings module 508 may determine one or control settings for the acoustic oscillator 108 including, but not limited to: magnitude and frequency of an acoustic pulse to be applied to the tissue.

ii. Treatment Selection Module

Referring to FIG. 5, the tissue assessment module 212 may further include a treatment selection module 510 configured to select one or more treatment protocols based on the analysis of the tissues determined by the 2D tissue assessment module 502, as well as other tissue characteristics determined by the trigger point analysis module 506. The recommended treatment protocols may be displayed to the operator as a list of treatment protocol options in an aspect. One or more treatment protocols may be selected from the displayed list by the operator in order to initiate one or more treatments to the tissues of the patient.

c. Operator-Selected Treatment Module

Referring back to FIG. 2, the treatment protocol selection module 208 includes an operator-selected treatment module 214 configured to develop and implement a treatment protocol specified by an operator via the input device 114. In an aspect, the operator-selected treatment module 214 may offer guidance to the operator in the form of menus or suggested ranges for applied stimulation frequencies, force impulse magnitudes, frequencies of impulse production, and any other parameter associated with the treatment protocol selected by the operator.

In an aspect, the operator may specify a particular treatment mode and anatomical landmarks to be treated. An image may be displayed within a GUI display in this aspect to show the selected anatomical landmarks to be treated. Upon selection of a particular anatomical landmark, the GUI may display the control settings of the instrument used to provide the treatment to the tissues of the patient to the operator. The operator may then specify the control settings of the instrument via the GUI. Alternatively, the GUI may guide the operator through a measurement of another characteristic of the tissue, and control settings of the instrument may be recommended to the operator based on the measured condition of the tissue. The instrument control settings are used to configure the instrument used to administer the treatment to the tissues of the patient.

IV. Treatment Modules

Referring back to FIG. 2, the treatment protocol selection module 120A selects a treatment protocol for a treatment of a tissue of a patient as discussed above. To implement the selected treatment protocol, the system 100A may make use of one or more treatment modules: a neural treatment module 216, a muscular treatment module 218, and a circulatory treatment module 220. In general, each of the treatment modules provides an interface with which the operator may configure the instrument to be used to treat the tissue of the patient according to the selected treatment protocol. In addition, each of the treatment modules may provide step-by-step guidance to the operator for placing the instrument on one or more selected anatomical landmarks of the patient and operating the instrument used to provide the treatment specified by the selected treatment protocol.

In an aspect, measurements of the condition of the tissues including, but not limited to, the response of the tissue in reaction to applied force impulses may be obtained. The post-treatment measurements may be stored in the database 122 in an embodiment.

Detailed descriptions of the neural treatment module 216, the muscular treatment module 218, and the circulatory treatment module 220 are provided herein below.

a. Neural Treatment Module

In an aspect, the neural treatment module 216 guides the operator through a treatment of a nerve tissue in accordance with a selected treatment protocol. In this aspect, the neural treatment module 216 may apply percussive impacts to nerves using the impulse stimulator instrument 106. Other treatment protocols including, but not limited to, acoustic oscillations applied to nerve tissues may be implemented in other embodiments.

Without being limited to any particular theory, the treatment protocols implemented by the neural treatment module 216 may target Golgi tendon organs within the tissues of the patient. The Golgi tendon organs are encapsulated mechanoreceptors located at the myo-tendinous and myo-aponeurosis junctions. As muscle fibers shorten during a muscle contraction, the Golgi capsule containing the Golgi tendon organ becomes distorted and the contraction of the fibers forming the Golgi capsule exerts a strain on the encapsulated collagen bundle within the Golgi capsule causing a deformation of sensory terminals. The Golgi tendon organ has a very low activation threshold, and even a single muscle fiber twitch may elicit a discharge from this receptor. The discharge frequency of the Golgi tendon organ controls the proprioceptive response. Under prolonged muscle fiber contractions, such as may occur under static and prolonged muscle loading, the discharge frequency of the Golgi tendon organ diminishes, causing the proprioceptive response to be minimized or extinguished altogether. As a result of an attenuated proprioceptive response, agonist/antagonist muscle activity becomes spastic and static. In addition, a prolonged static loading condition may result in hyperactivity of the nociceptor response resulting in pain and additional muscle spasms.

Golgi tendon organs are known to fire harmonically with stimulating impulses up to 80 Hz and in a subharmonic manner (½ to ⅓) above 80 Hz. The Golgi tendon organ ($I_b$) afferents are also known to display an inverse pattern of activity relative to the firing of ($I_a$) afferents. As a result, the motor response may be inversely proportional to Golgi tendon organ firing; as the discharge frequency from Golgi tendon organs is depressed, the motor response becomes more active. Therefore the reduction in the frequency of Golgi tendon organ firing under prolonged static muscle contraction may induce a motor response hyperactivity akin to muscle hypertonia.

If a Golgi tendon organ is stimulated by applying low magnitude force oscillations within the known frequency response window of the Golgi capsule, the resulting Golgi tendon organ discharge frequency may respond harmonically to the induced oscillation frequency, inducing an appropriate proprioceptive response. In particular, the applied force oscillations may elicit a harmonic response of the Ib afferents of the Golgi tendon organ, resulting in diminished nociceptor signaling and the alleviation of pain, absent other factors such as chemical irritants, infection or inflammation within the afflicted tissue.

Figure 8:
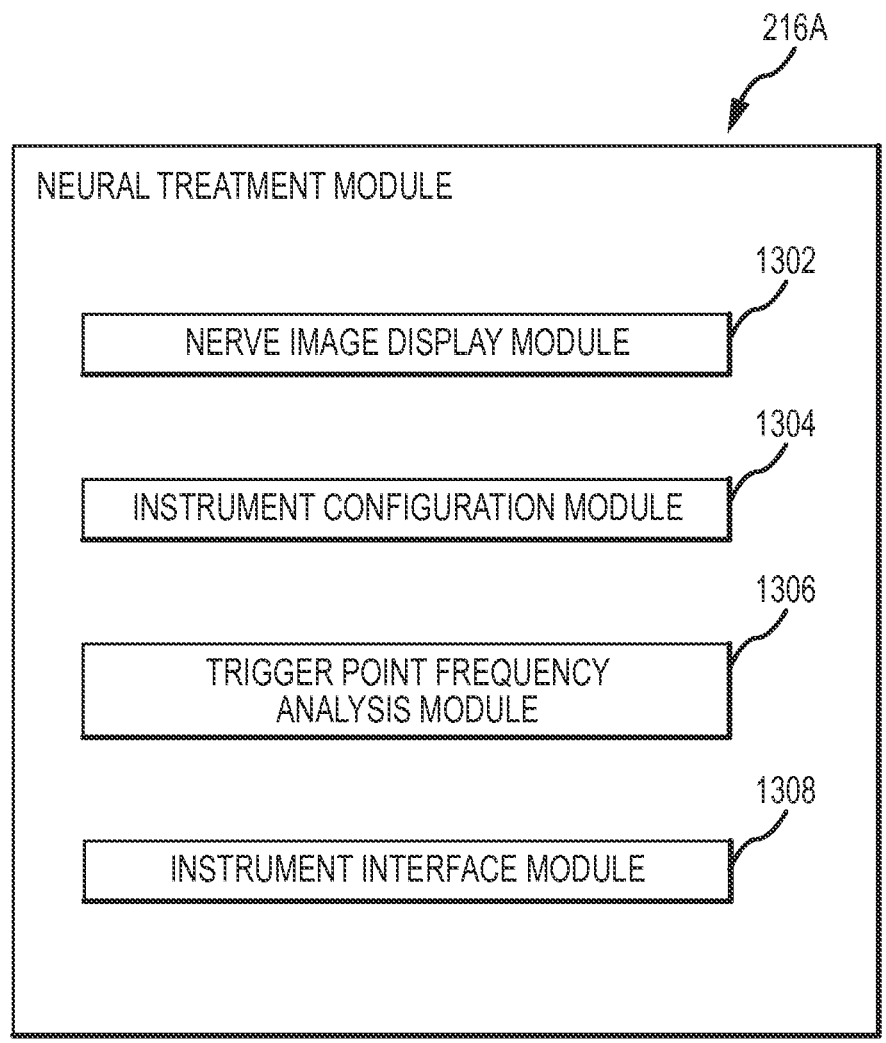
FIG. 8 is a block diagram of a neural treatment module.

FIG. 8 is a block diagram illustrating an embodiment of a neural treatment module 216A. The neural treatment module 216A may include a nerve image display module 1302 to produce a GUI used to guide the operator through a treatment of a nerve tissue. An instrument configuration module 1304 may be used to specify the control settings of the impulse stimulator instrument used to implement a treatment of the nerve tissue including, but not limited to the magnitude and frequency of the applied percussive force, and the duration of the treatment. A trigger point frequency analysis module 1306 may guide the operator through an analysis in which the impulse stimulator instrument is used to measure the response of the tissue through a range of frequencies of the applied percussive force and determine one or more instrument control settings based on an analysis of the measured tissue response. The instrument interface module 1308 provides a GUI or other interface used by the operator to operate the impulse stimulator instrument while implementing a selected treatment protocol.

Figure 9:
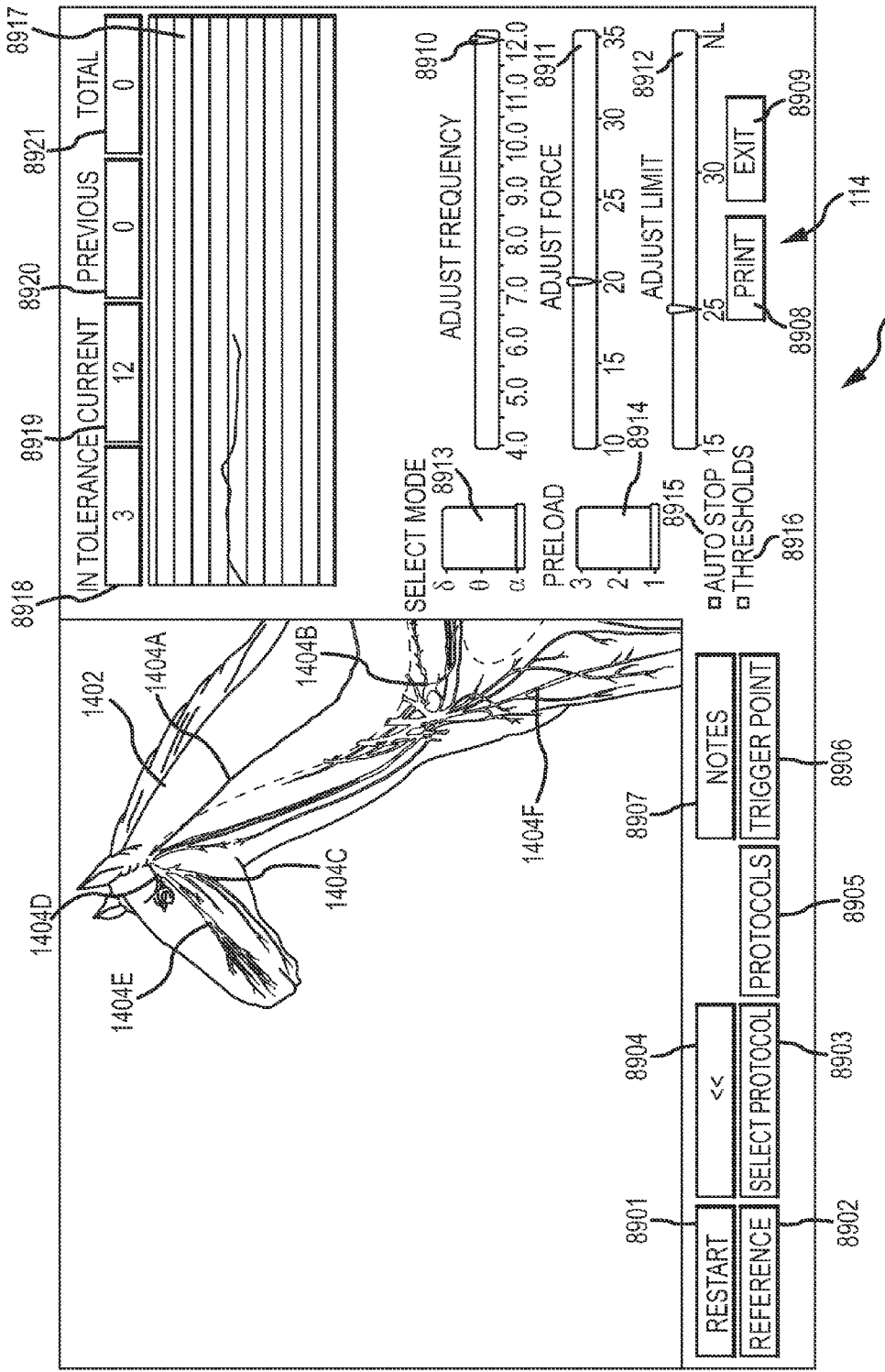
FIG. 9 is an embodiment of a neural treatment guidance display.

An example of a nerve display 1400 is illustrated in FIG. 9. The nerve display 1400 may include a nerve image 1402 illustrating the location of nerves to aid the operator in locating the appropriate region for treatment. In an aspect, the location of anatomical landmarks 1404A-1404F identified by the treatment protocol selection module 208 may be superimposed on the nerve image 1402. The frequency at which the force impulses are applied to the nerve tissues may be displayed and/or specified using a GUI control element such as the slider control 8910 illustrated in FIG. 9. In this example, a portion of a horse is illustrated in the nerve image 1402, and the nerve routes and anatomical landmarks 1404A-1404F pertain to a horse. Of course, depending on what animal is being treated and how the treatment system 100 is configured, the nerve image 1402, nerve routes and anatomical landmarks can pertain to any animal being treated, such as, for example, a dog, cat, cattle, lion, elephant, whale, dolphin, etc.

The nerve display 1400 may further include controls (e.g., buttons, sliders, etc.) and readouts (e.g., gages, graphs, etc.) 8901-8921 used to control and understand various aspects of the treatment of the nerve tissue. In one embodiment, the GUI 1400 depicted in FIG. 9 is displayed on the display 112 of FIG. 1 (or FIG. 31) once the setup of the system 100 has been achieved as described below with respect to the GUI 8860 of FIG. 33 or as described above. As indicated in FIG. 9, the GUI 1400 includes the anterior horse image 1402 with its trigger points 1404A-1404F. The GUI 1400 also includes an input device 114 with touch sensitive screen buttons "Restart", "Reference", "Select Protocol", "<<", "Protocols", "Trigger Point", "Notes", "Print", and "Exit" 8901-8909. The input device 114 of the GUI 1400 also includes touch sensitive screen sliders "Adjust Frequency", "Adjust Force", "Adjust Limit", "Select Mode", and "Preload" 8910-8914. Finally, the GUI 1400 also includes "Auto Stop" and "Thresholds" indicates 8915 and 8916 and a graphical display 8917 to illustrate the treatment and "In Tolerance", "Current", "Previous" and "Total" indicators 8918-8921.

In one embodiment, the user interface contains various controls that aid the user by providing control and treatment feedback information. If the user makes an error they can easily restart the protocol by simply pressing the "Restart" button 8901. Additionally the user may wish to just go back to the previous point and can do so by selecting the "<<" selection 8904. The "Reference Button" 8902 is used to store information regarding the anatomical area of treatment, treatment overview and rationale, treatment goals and or expected responses. The user may also go back to the list of protocols by choosing the "select protocol" button 8903.

Functionality can be quickly switched from a protocol to a trigger point by choosing either "protocol" 8905 or trigger point 8906 to select the type of therapy desired. The notes button 8907 brings up a window to allow the user to enter information in a text format via the keyboard. General treatment controls include frequency, force and limits 8910-8912. While the computer calculates the frequency, the user can override it by touching the screen and moving the digital slider. However, the force and limit have defaults that are parameters selected by the user to determine how much power will be used and the maximum number of impulses that can be delivered. The selection mode 8913 is used to chose what harmonic frequency is chosen within the range of frequencies of 0.1 to 12 Hz.

There are different input frequencies depending on whether one is attempting to stimulate a nerve, voluntary muscle fiber or involuntary muscle fiber. The ranges are Alpha 7-12, Theta 4-7, and Delta 0.1 to 4 Hz. The selection mode slider 8913 allows the user to dynamically choose the proper harmonic frequency dynamically.

The preload function 8914 changes the amount of pressure that is used to compress the tissue before the treatment applicator begins to produce impulse. Because animals vary widely in their physiological characteristics and tolerances, varying amounts of pressure can be used. Preload 8914 provides a way to control this pressure without having to change treatment heads.

As treatment is progressing, information about the tissue response is shown on a strip chart 8917. Information includes real time output from the sensor showing changes in tissue tone, changes in tissue frequency response and changes in wave shape characteristics. If auto-stop is chosen 8915, these signals will be interpreted and the device will automatically stop treatment based upon a definable tolerance. For instance, if a tolerance of 3% is used for tissue stiffness, the device will stop treatment based upon receiving a predefined number of impulses that are all within 3% of each other.

Thresholds 8916 may be turned on or off to give the user a visual scale of how the treatment parameters are progressing in real time with regard to the auto-stop parameters. As the treatment progresses the real time measurements are tabulated in 8918 through 8921. "In Tolerance" 8918 displays the impulses that fall within the pre-defined tolerance indications. "Current" 8919 displays the number of impulses that have been delivered during the activation of the treatment head during the active treatment while "Previous" 8920 shows the previous number of impulses during the last treatment application and "Total" 8921 displays the total number of impacts delivered during the entire treatment. After the treatment is concluded the users may print the screen by selecting the "Print" button 8908 or the user may simply exit the protocol screen by touching the "Exit" button 8909.

Figure 10:
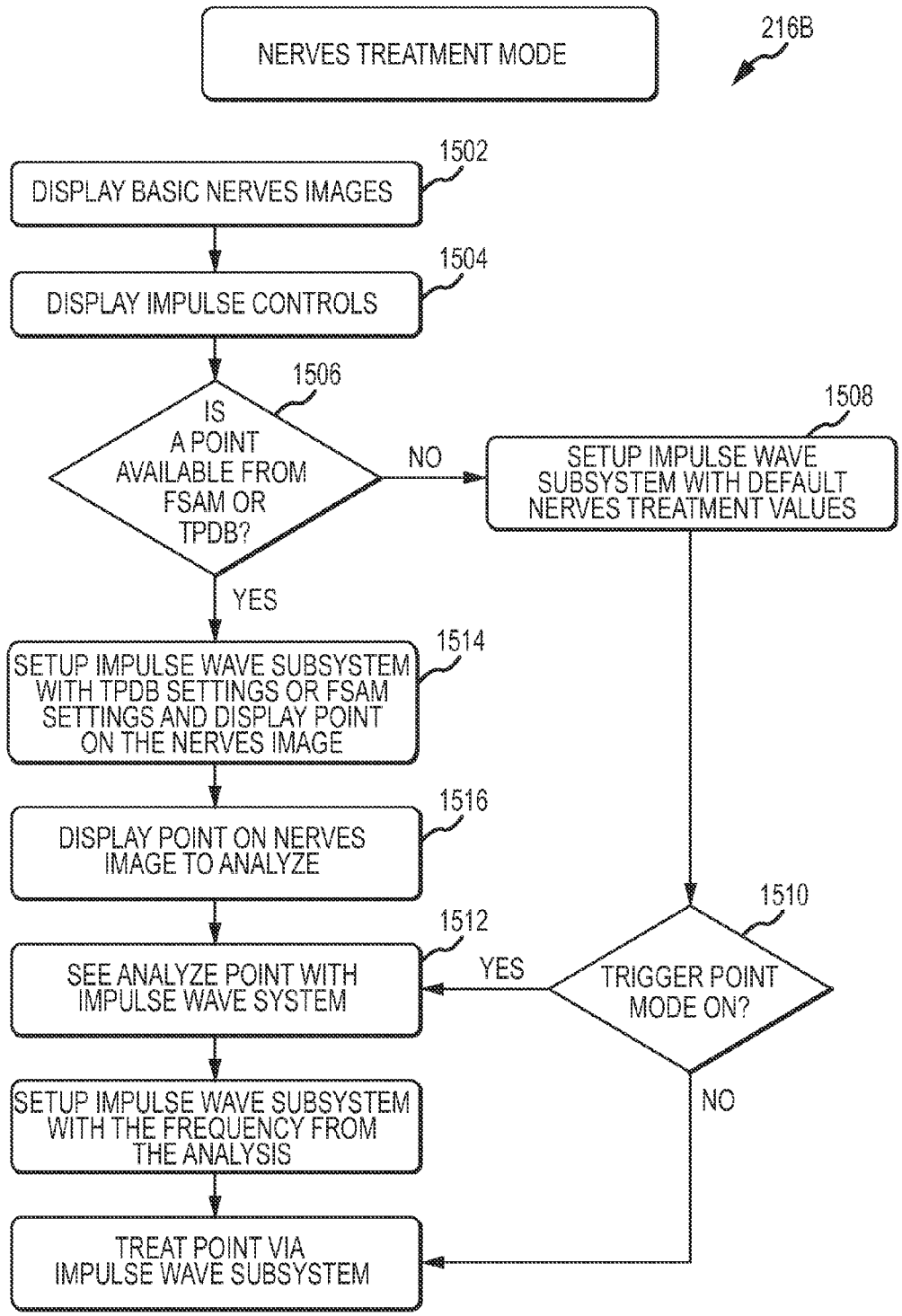
FIG. 10 is a flow chart illustrating an embodiment of a neural treatment module.

FIG. 10 is a flow chart illustrating an embodiment of the neural treatment module 216B. The nerve image 1402 and controls for the impulse stimulator instrument 106 may be displayed in the nerve display 1400 at steps 1502 and 1504. The neural treatment module 216B determines whether instrument control settings have been specified using the stored treatment protocol module 210 or tissue assessment module 212 at step 1506. If no instrument control setting has been specified, the instrument control settings are populated with default values at step 1508. Once the default values have been loaded, the neural treatment module 216B determines if a trigger point analysis is desired to refine the default settings at step 1510. If desired, a trigger point analysis is performed at the anatomical landmark at step 1512.

If instrument control settings were identified at step 1506, the settings are loaded into the nerve display 1400 at step 1514. An anatomical landmark to be treated is displayed on the nerve display 1400 at step 1516. If a trigger point analysis was conducted, the recommended instrument control settings are loaded in to the nerve display 1400 at step 1518, and the treatment is implemented at step 1520.

b. Muscular Treatment Module

Referring back to FIG. 2, the muscular treatment module 218 is configured to guide the operator through a treatment of one or more muscles associated with one or more anatomical landmarks in accordance with a selected treatment protocol. In this aspect, the muscular treatment module 218 may apply percussive impacts to muscles using the impulse stimulator instrument 106. Other treatment protocols including, but not limited to, acoustic oscillations applied to muscles may be implemented in other embodiments. The acoustic (Audio) oscillations may be in the form of pulse modulated RF and/or Amplitude modulated RF in various embodiments including square or sine waves.

The treatment protocols implemented by the muscular treatment module 218 may promote the health of muscles by reducing fluid stasis, thereby relieving muscle inflammation resulting from an altered chemical environment of the tissues and improving tissue metabolism in an aspect. In other aspects, the muscular treatment module 218 may implement a tendon vibration treatment that may stimulate mechanoreceptors, inducing the relaxation of muscles.

The relaxation of muscles induced by the treatment protocols implemented by the muscular treatment module 218 may relieve cramps, soreness and other discomfort associated with the prolonged contraction of one or more muscles.

Figure 11:
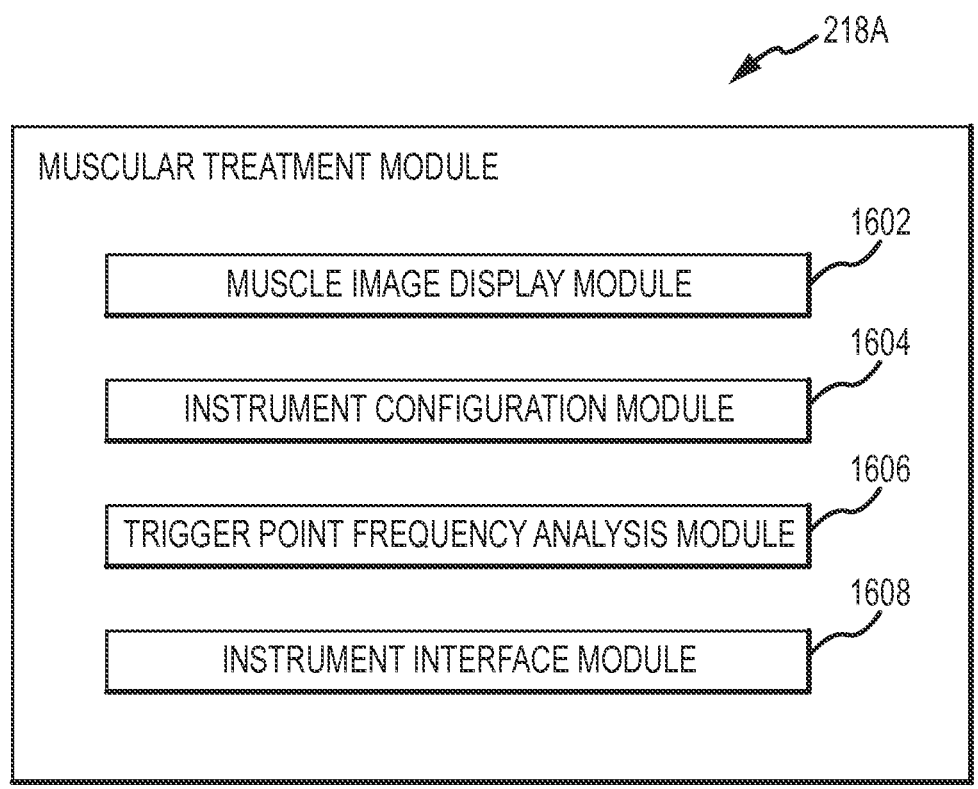
FIG. 11 is a block diagram of a muscular treatment module.

FIG. 11 is a block diagram illustrating an embodiment of a muscular treatment module 218A. The muscular treatment module 218A may include a muscle image display module 1602 to produce a GUI used to guide the operator through a treatment of a muscle tissue. An instrument configuration module 1604 may be used to specify the control settings of the impulse stimulator instrument 106 used to implement a treatment of the muscle tissue including, but not limited to the magnitude and frequency of the applied force impulse, and the duration of the treatment. A trigger point frequency analysis module 1606 may guide the operator through an analysis in which the stimulator instrument is used to measure the response of the tissue through a range of frequencies of the applied force impulse and to determine one or more instrument control settings based on an analysis of the measured tissue response. The instrument interface module 1608 provides a GUI or other interface used by the operator to operate the impulse stimulator instrument while implementing a selected treatment protocol.

Figure 12:
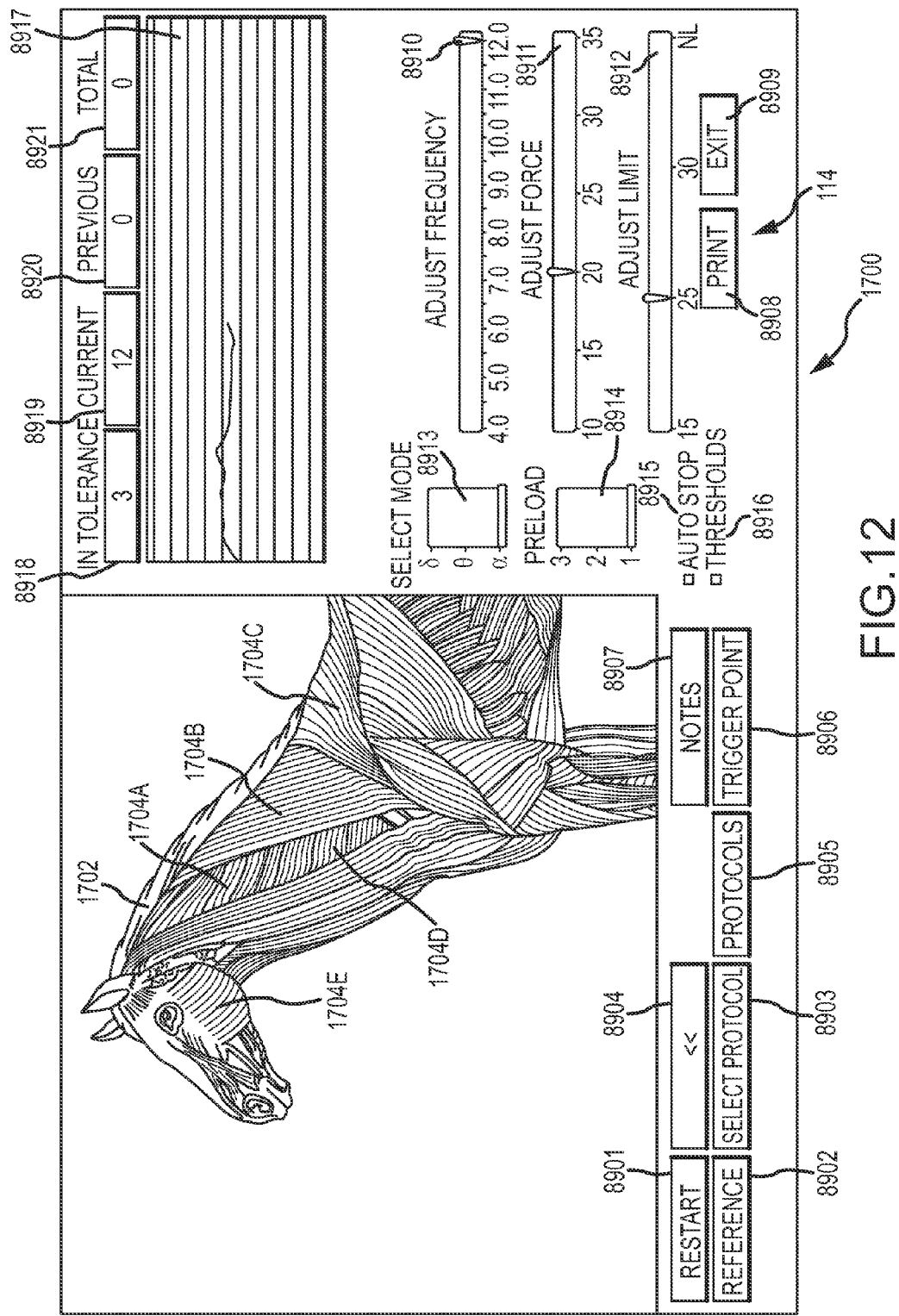
FIG. 12 is an embodiment of a muscular treatment guidance display.

An example of a muscle display 1700 is illustrated in FIG. 12. The muscle display 1700 may include a muscle image 1702 illustrating the location of muscle to aid the operator in locating the appropriate region for treatment. In an aspect, the location of anatomical landmarks 1704A-1704E identified by the treatment protocol selection module 208 may be superimposed on the muscle image 1702. The frequency at which the force impulses are applied to the muscle tissues may be displayed and/or specified using a GUI control element such as the slider control 1708 illustrated in FIG. 12. In this example, a portion of a horse is illustrated in the muscle image 1702, and the muscles and anatomical landmarks 1704A-1404E pertain to a horse. Of course, depending on what animal is being treated and how the treatment system 100 is configured, the muscle image 1702, muscles and anatomical landmarks can pertain to any animal being treated, such as, for example, a dog, cat, cattle, lion, elephant, whale, dolphin, etc.

The nerve display 1700 may further include controls (e.g., buttons, sliders, etc.) and readouts (e.g., gages, graphs, etc.) 8901-8921 used to control and understand various aspects of the treatment of the muscle tissue. In one embodiment, the GUI 1700 depicted in FIG. 12 is displayed on the display 112 of FIG. 1 (or FIG. 31) once the setup of the system 100 has been achieved as described below with respect to the GUI 8860 of FIG. 33 or as described above. As indicated in FIG. 12, the GUI 1700 includes the anterior horse image 1402 with its trigger points 1704A-1704E. The GUI 1700 also includes an input device 114 with touch sensitive screen buttons "Restart", "Reference", "Select Protocol", "<<", "Protocols", "Trigger Point", "Notes", "Print", and "Exit" 8901-8909. The input device 114 of the GUI 1700 also includes touch sensitive screen sliders "Adjust Frequency", "Adjust Force", "Adjust Limit", "Select Mode", and "Preload" 8910-8914. Finally, the GUI 1700 also includes "Auto Stop" and "Thresholds" indicates 8915 and 8916 and a graphical display 8917 to illustrate the treatment and "In Tolerance", "Current", "Previous" and "Total" indicators 8918-8921.

In one embodiment, the user interface contains various controls that aid the user by providing control and treatment feedback information. If the user makes an error they can easily restart the protocol by simply pressing the "restart" button 8901. Additionally the user may wish to just go back to the previous point and can do so by selecting the "<<" selection 8904. The "Reference Button" 8902 is used to store information regarding the anatomical area of treatment, treatment overview and rationale, treatment goals and or expected responses. The user may also go back to the list of protocols by choosing the "select protocol" button 8903.

Functionality can be quickly switched from a protocol to a trigger point by choosing either "protocol" 8905 or trigger point 8906 to select the type of therapy desired. The notes button 8907 brings up a window to allow the user to enter information in a text format via the keyboard. General treatment controls include frequency, force and limits 8910-8912. While the computer calculates the frequency, the user can override it by touching the screen and moving the digital slider. However, the force and limit have defaults that are parameters selected by the user to determine how much power will be used and the maximum number of impulses that can be delivered. The selection mode 8913 is used to choose what harmonic frequency is chosen within the range of frequencies of 0.1 to 12 Hz.

There are different input frequencies depending on whether one is attempting to stimulate a nerve, voluntary muscle fiber or involuntary muscle fiber. The ranges are Alpha 7-12, Theta 4-7, and Delta 0.1 to 4 Hz. The selection mode slider 8913 allows the user to dynamically choose the proper harmonic dynamically.

The preload function 8914 changes the amount of pressure that is used to compress the tissue before the treatment applicator begins to produce impulse. Because animals vary widely in their physiological characteristics and tolerances, varying amounts of pressure can be used. Preload 8914 provides a way to control this pressure without having to change treatment heads.

As treatment is progressing, information about the tissue response is shown on a strip chart 8917. Information includes real time output from the sensor showing changes in tissue tone, changes in tissue frequency response and changes in wave shape characteristics. If auto-stop is chosen 8915, these signals will be interpreted and the device will automatically stop treatment based upon a definable tolerance. For instance, if a tolerance of 3% is used for tissue stiffness, the device will stop treatment based upon receiving a predefined number of impulses that are all within 3% of each other.

Thresholds 8916 may be turned on or off to give the user a visual scale of how the treatment parameters are progressing in real time with regard to the auto-stop parameters. As the treatment progresses the real time measurements are tabulated in 8918 through 8921. "In tolerance" 8918 displays the impulses that fall within the pre-defined tolerance indications. "Current" 8919 displays the number of impulses that have been delivered during the activation of the treatment head during the active treatment while "previous" 8920 shows the previous number of impulses during the last treatment application and "Total" 8921 displays the total number of impacts delivered during the entire treatment. After the treatment is concluded the users may print the screen by selecting the "print" button 8908 or the user may simply exit the protocol screen by touching the "exit" button 8909.

Figure 13:
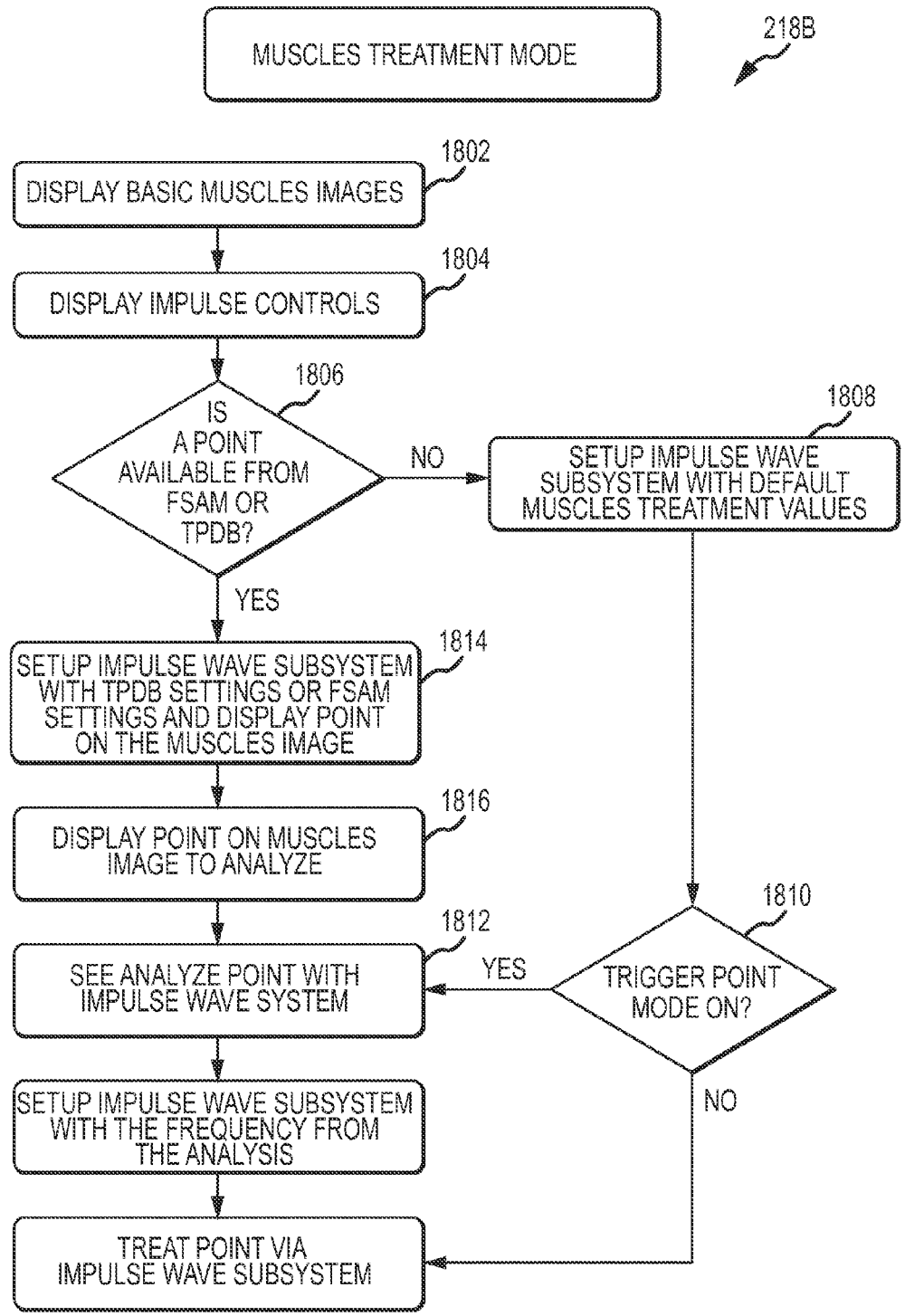
FIG. 13 is a flow chart illustrating an embodiment of a muscular treatment module.

FIG. 13 is a flow chart illustrating an embodiment of the muscular treatment module 218B. The muscle image 1702 and controls for the impulse stimulator instrument 106 may be displayed in the muscle display 1700 at steps 1802 and 1804. The muscular treatment module 216B determines whether instrument control settings have been specified using the stored treatment protocol module 210 or tissue assessment module 212 at step 1806. If no instrument control setting has been specified, the instrument control settings are populated with default values at step 1808. Once the default values have been loaded, the muscular treatment module 218B determines if a trigger point analysis is desired to refine the default settings at step 1810. If desired, a trigger point analysis is performed at the anatomical landmark at step 1812.

If instrument control settings were identified at step 1806, the settings are loaded into the muscle display 1700 at step 1814. An anatomical landmark to be treated is displayed on the muscle display 1700 at step 1816. If a trigger point analysis was conducted, the recommended instrument control settings are loaded into the muscle display 1700 at step 1818, and the treatment is implemented at step 1820.

c. Circulatory Treatment Module

Referring back to FIG. 2, the circulatory treatment module 220 is configured to guide the operator through a treatment of one or more circulatory vessels associated with one or more anatomical landmarks in accordance with a selected treatment protocol. In this aspect, the circulatory treatment module 220 may apply acoustic pulses to circulatory vessels using the acoustic oscillator 108. Other treatment protocols including, but not limited to, force impulses applied to circulatory vessels may be implemented in other embodiments.

The treatment protocols implemented by the circulatory treatment module 220 may stimulate enhanced blood flow to the tissues, thereby enhancing the health, function, recovery and appearance of the tissues.

Figure 14:
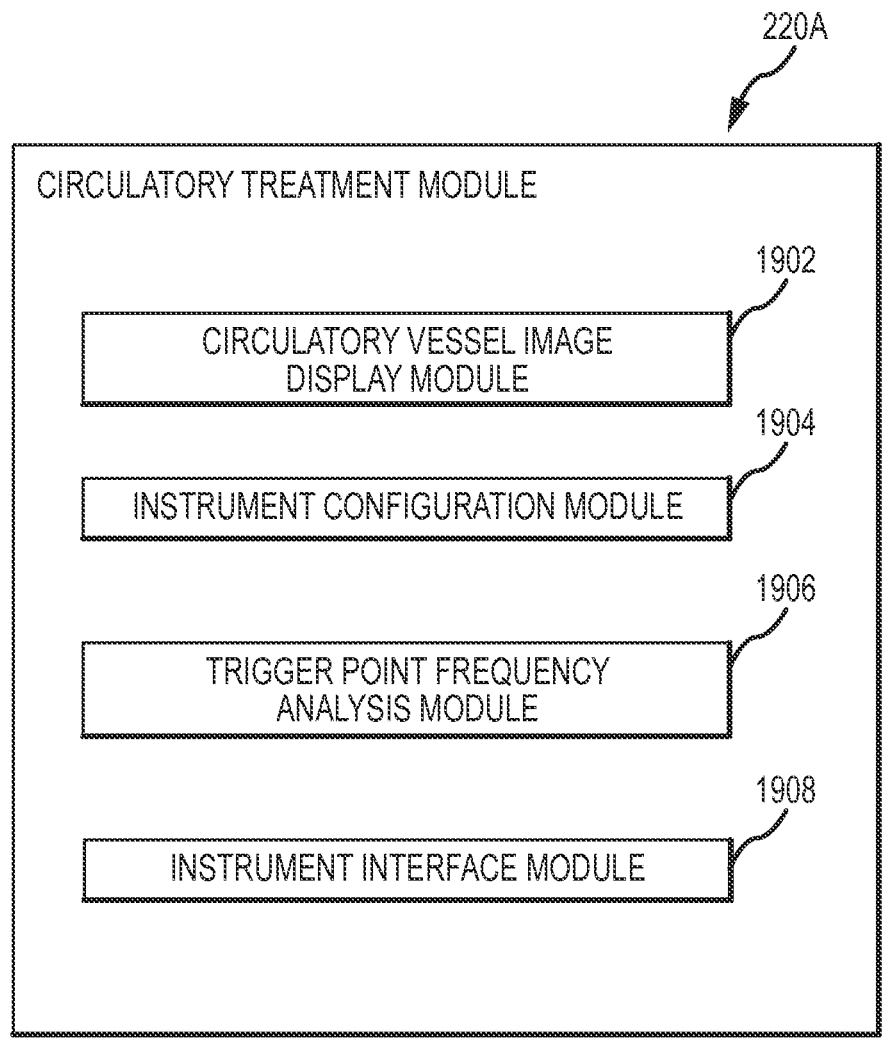
FIG. 14 is a block diagram of a circulatory treatment module.

FIG. 14 is a block diagram illustrating an embodiment of a circulatory treatment module 220A. The circulatory treatment module 220 may include a circulatory vessel image display module 1902 to produce a GUI used to guide the operator through a treatment of a circulatory vessel. An instrument configuration module 1904 may be used to specify the control settings of the acoustic oscillator used to implement a treatment of the circulatory vessel tissue including, but not limited to the magnitude and frequency of the applied acoustic pulses, and the duration of the treatment. The instrument interface module 1908 provides a GUI or other interface used by the operator to operate the acoustic oscillator while implementing a selected treatment protocol.

A trigger point frequency analysis module 1906 may guide the operator through an analysis in which the impulse stimulator instrument 106 is used to measure the response of the tissue through a range of frequencies of applied percussive force at the various anatomical landmarks selected for treatment and to determine one or more instrument control settings based on an analysis of the measured tissue response. For example, the trigger point frequency analysis module 1906 may determine a resonant frequency for each of the anatomical landmarks using the tissue response measured by the impulse stimulator instrument 106. These resonant frequencies may be used as a basis for a treatment frequency protocol at each of the anatomical landmarks that specifies the frequency of acoustic pulses to be applied at each anatomical landmark.

In an aspect, the treatment frequency protocol may be a sweep concentration frequency protocol, in which the acoustic pulses are provided in the form of a programmable duty cycle transmission wave. In this aspect, the acoustic pulses may have an oscillation frequency ranging between about 800 KHz and about 1 MHz delivered at a pulse rate ranging between about 3 Hz and about 300 Hz. In this aspect, the pulse rate may be concentrated within the harmonics and sub-harmonics of the resonant frequency determined by the trigger point frequency analysis module 1906. This pulse can be delivered as a burst or in an amplitude modulated form.

In another aspect, the treatment frequency protocol may be a harmonic sweep concentration protocol similar to the sweep concentration frequency protocol, except that the pulse rate may be initially set at the exact resonant frequency determined by the trigger point frequency analysis module 1906 and subsequently swept up and down the harmonic range.

In an additional aspect, the treatment frequency protocol may be a resonance concentration similar to the sweep concentration frequency protocol and harmonic sweep protocol, except that the pulse rate is initialized and maintained at the specific resonant frequency determined by the trigger point frequency analysis module 1906.

Figure 15:
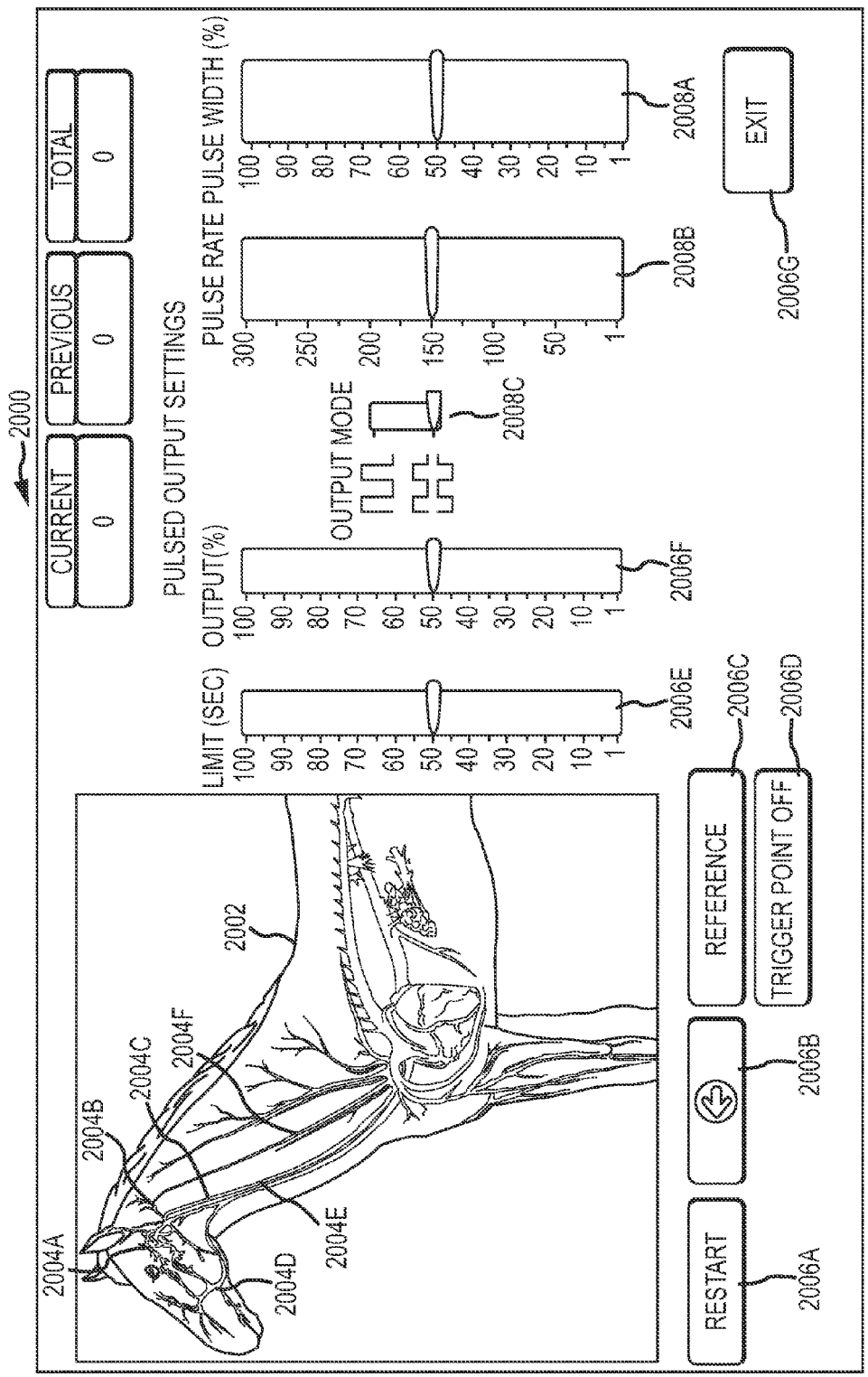
FIG. 15 is an embodiment of a circulatory treatment guidance display.

An example of a circulatory vessel display 2000 is illustrated in FIG. 15. The circulatory vessel display 2000 may include a circulatory vessel image 2002 illustrating the location of a circulatory vessel to aid the operator in locating the appropriate region for treatment. In an aspect, the location of anatomical landmarks 2004A-2004F identified by the treatment protocol selection module 208 may be superimposed on the circulatory vessel image 2002. The rate and mode that the acoustic pulses are applied to the circulatory tissues may be displayed and/or specified using GUI control element(s) such as controls 2008A-2008C Illustrated in FIG. 15. For example, sliders 2008A-2008C are, respectively, for setting pulse width, pulse rate and output mode where the output may be caused to be pulsed or modulated.

In this example, a portion of a horse is illustrated in the circulatory vessel image 2002, and the circulatory vessel routes and anatomical landmarks 2004A-2004E pertain to a horse. Of course, depending on what animal is being treated and how the treatment system 100 is configured, the circulatory vessel image 2002, circulatory vessel routes and anatomical landmarks can pertain to any animal being treated, such as, for example, a dog, cat, cattle, lion, elephant, whale, dolphin, etc.

The circulatory vessel display 2000 may further include sliders 2006E-2006F used to control various other aspects of the treatment of the circulatory tissue. The duration of the acoustic pulses applied at each anatomical landmark may be specified by selecting the value on slider 2006E. The magnitude of the acoustic pulses may be specified by selecting a value on slider 2006F. A trigger point analysis may be initiated by selecting button 2006D. Useful reference information may be accessed by the operator by selecting button 2006C. The operator may move between anatomical landmarks to be treated by selecting button 2006B, restart the treatment by selecting 2006A, or cease treatment of the circulatory vessels by selecting button 2006G.

Figure 16:
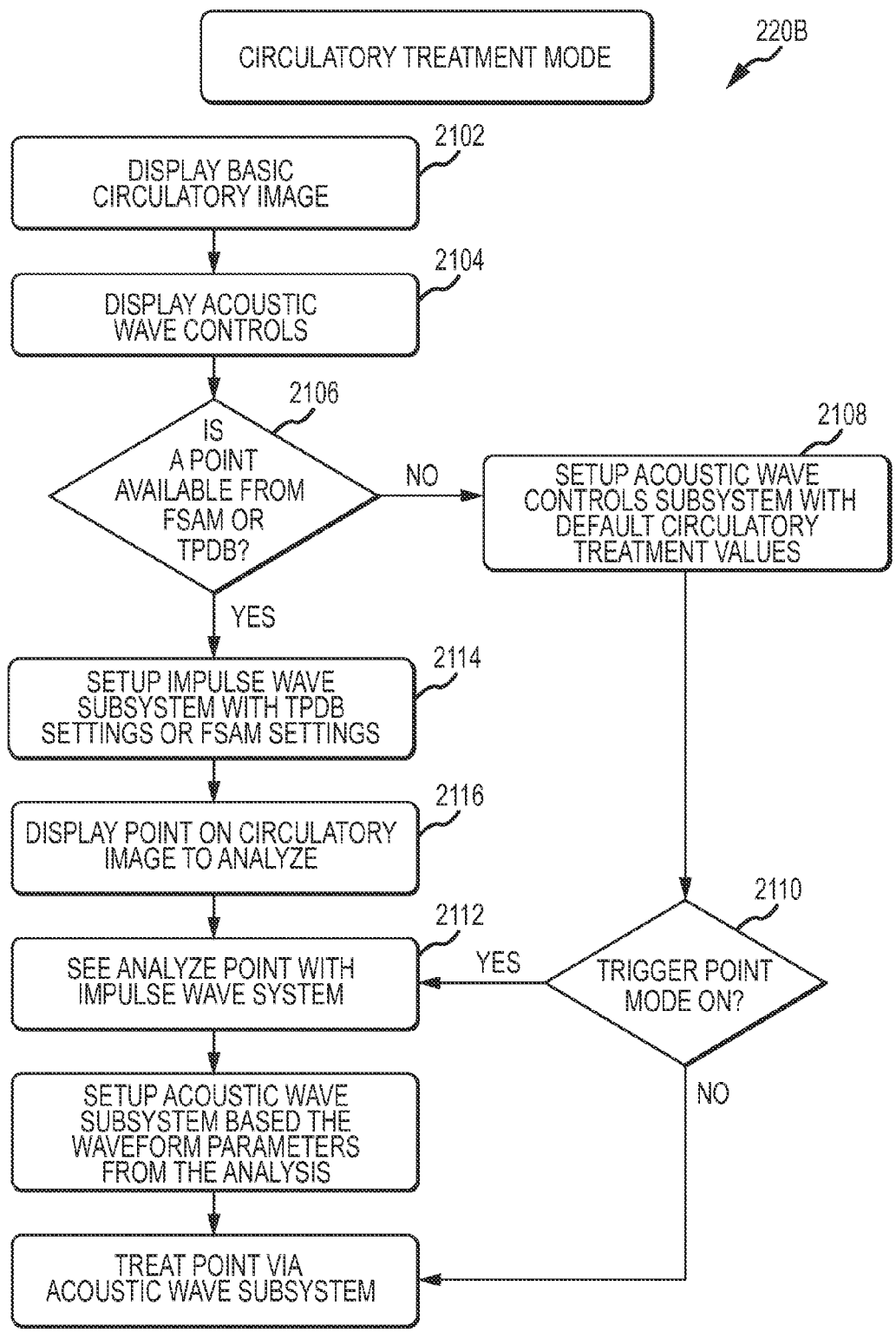
FIG. 16 is a flow chart illustrating an embodiment of a circulatory treatment module.

FIG. 16 is a flow chart illustrating an embodiment of the circulatory treatment module 220B. The circulatory vessel image 2002 and controls for the acoustic oscillator 108 may be displayed in the circulatory vessel display 2000 at steps 2102 and 2104. The circulatory treatment module 220B determines whether instrument control settings have been specified using the stored treatment protocol module 210 or tissue assessment module 212 at step 2106. If no instrument control settings have been specified, the instrument control settings are populated with default values at step 2108. Once the default instrument controls settings have been loaded, the circulatory treatment module 220B determines if a trigger point analysis is desired to refine the default settings at step 2110. If desired, a trigger point analysis is performed at the anatomical landmark at step 2112.

If any instrument control settings were identified at step 2106, the settings are loaded into the circulatory vessel display 2000 at step 2114. An anatomical landmark to be treated is displayed on the circulatory vessel display 2000 at step 2116. If a trigger point analysis was conducted, the recommended instrument control settings are loaded into the circulatory vessel display 2000 at step 2118, and the treatment is implemented at step 2120.

V. Database

Referring back to FIG. 1, a database 122 may store a variety of data for use by the treatment system 100 to provide a treatment to the tissues of a patient. In an aspect, the database 122 may include the entries associated with stored treatment protocols 124, stored patient data 126, and measurement-correlated instrument control settings 132. In an aspect, the stored patient data 126 may include stored anatomical images 128 and patient-specific treatment protocols 130. The entries stored in the database 122 may be accessed by the modules of the treatment application 120 to aid in the analysis of the condition of a patient's tissues, the selection of a treatment protocol, and the specification of one or more instrument control settings associated with a selected treatment protocol and/or a measured characteristic of a tissue, and the implementation of the tissue treatment by the system 100.

a. Stored Treatment Protocols

Figure 18:
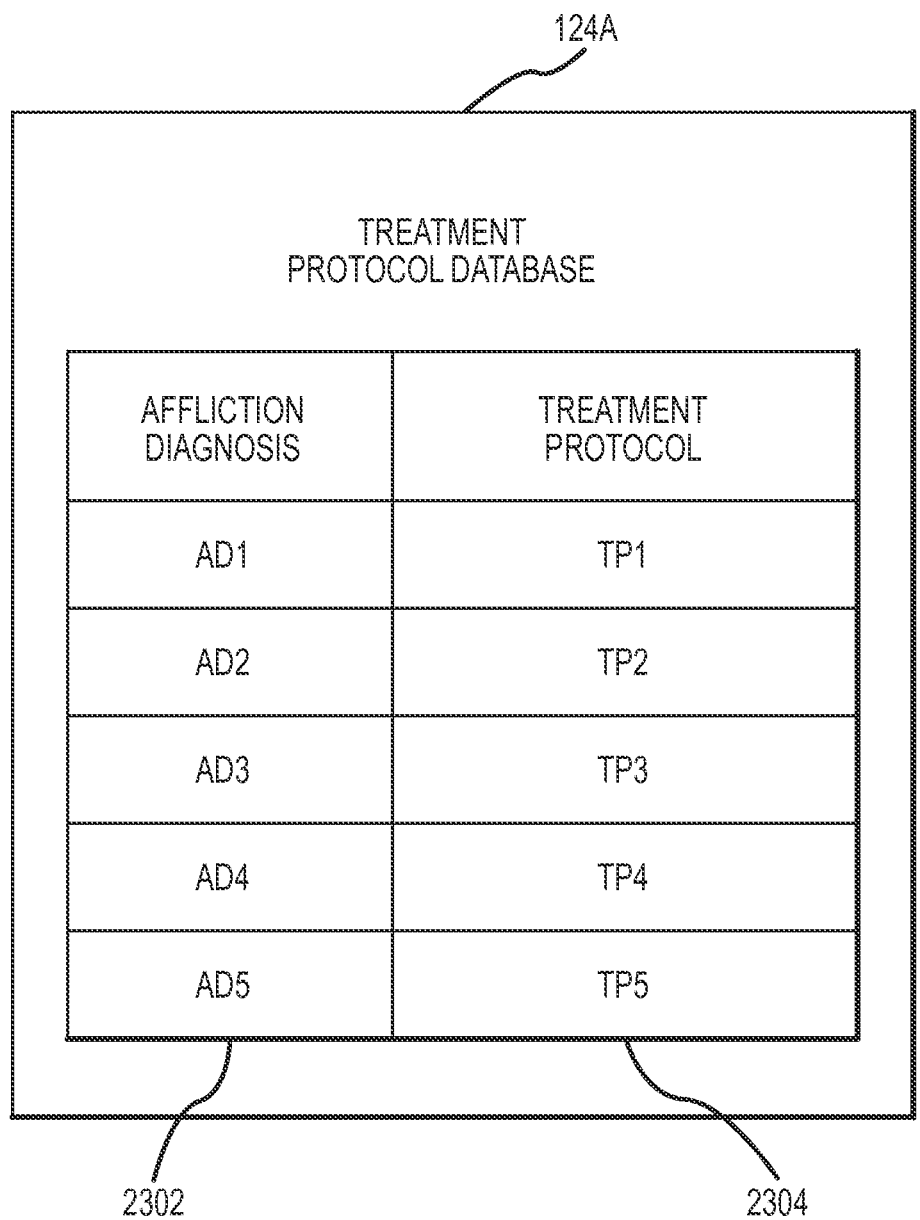
FIG. 18 is a diagrammatic depiction of a database for selecting a treatment protocol based on a diagnosis of a tissue disorder.

In an aspect, the stored treatment protocols 124 may provide the instrument control settings, anatomical landmarks, and/or any other information specifying a treatment protocol. FIG. 18 is a diagrammatic depiction of an embodiment of a stored treatment protocol 124A. In this aspect, the stored treatment protocol database 124A includes a list of affliction diagnosis entries 2302 and associated treatment protocols 2304. The affliction diagnosis entries 2302 may be any of the afflictions of the tissues described previously above. Non-limiting examples of affliction diagnosis entries 2302 include changes related to aging, injury, development, and disease.

b. Stored Patient Data

In another aspect, the database 122 may further include stored patient data 126 including, but not limited to, information about the patient such as age, height, weight, and medical history, results of analyses of the patient's tissues, treatments performed on the patient's tissues, notes and comments by the operator, and a schedule of future treatments to be performed. The information contained within the stored patient data 126 provides information for use by the operator of the system 100 to select a treatment, assess the efficacy of an administered treatment, and/or select a future treatment protocol. The history of patient analysis and treatment may be compiled and used for discussion of patient's condition and progress as well as justification for continuing treatment and rehabilitation.

i. Stored Anatomical Images

In an additional aspect, anatomical images of the patient obtained before, during, and/or after a treatment may be stored in the stored anatomical images 128. The images may be 2D anatomical images and/or 3D anatomical images described above. The anatomical images may be stored for one or more treatments and may be used to assess the efficacy of the treatments over an extended time period. In another aspect, additional information such as anatomical landmarks, analysis results, and previously suggested treatments may be associated with the anatomical images and stored in the stored anatomical images 128.

ii. Patient-Specific Treatment Protocols

In another additional aspect, a set of treatment protocols customized for a particular patient may be stored in the stored patient data 126 as patient-specific treatment protocols 130. The entries within the patient-specific treatment protocols may include information including, but not limited to anatomical landmarks to be treated, the type of treatment to be applied, the instrument control settings associated with the treatment protocol, and any other information useful to defining a particular treatment protocol and implementing the treatment. In an aspect, the patient-specific treatment protocols 130 may be accessed by the operator and used to implement the treatment of a patient's tissues without need for measurements of the condition of the patient's tissues. In another aspect, the patient-specific treatment protocols 130 may include the treatment protocols of treatments to be administered according to a schedule developed by the operator.

iii. Stored Instrument Control Settings

In another additional aspect, one or more tables containing entries used to determine one or more instrument control settings based on one or more measurements of the condition of a tissue may be stored in the measurement-correlated instrument control settings 132. These entries may be accessed by modules of the tissue treatment application related to trigger point analysis, dynamic adjustment of control settings, implementation of treatment protocols, and the like. Any instrument control setting of any instrument may be stored as a function of any measurement of the tissue in the measurement-correlated instrument control settings 132.

VI. Impulse Stimulator Instrument

Referring again to FIG. 1, the tissue treatments of an animal patient may be implemented using one or more instruments, including an impulse stimulator instrument 106. The impulse stimulator instrument 106 may be configured to deliver a mechanical force impulse to the tissues. In addition, the impulse stimulator instrument 106 may be configured for the measurement of tissue response arising from the application of a force impulse to the tissue of a patient.

Figure 17:
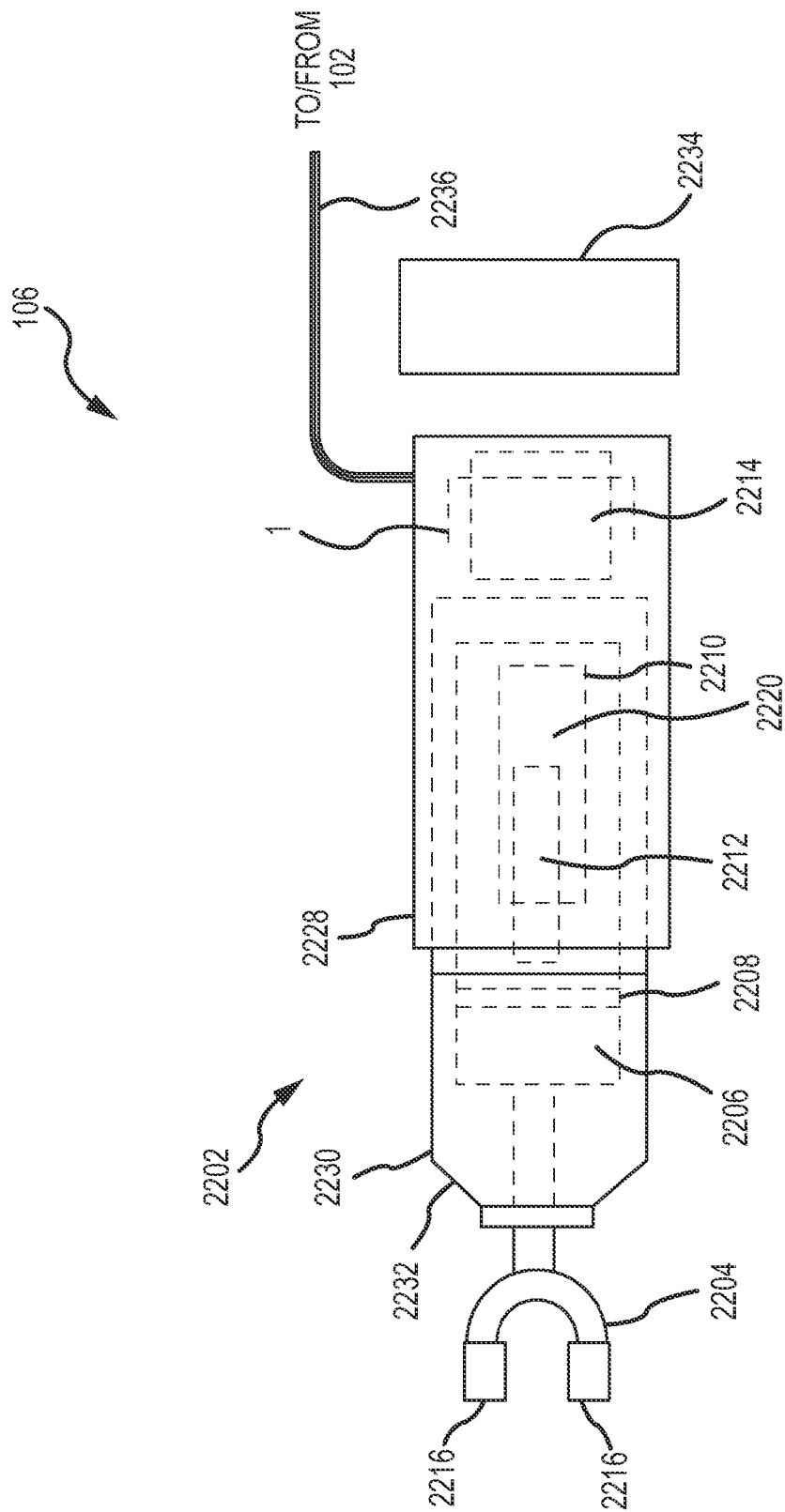
FIG. 17 is a cross-sectional side view of an impulse stimulator instrument.

FIG. 17 is a side view of the impulse stimulator instrument 106 in one aspect. The impulse stimulator instrument 106 includes an impulse and sensing head 2202 that contacts the tissues of the patient to deliver the mechanical force impulses. The impulse and sensing head 2202 includes a probe 2204 with one or more tips 2216 that contact the tissues of the patient. A piezoelectric sensor 2206 is firmly attached to the probe 2204, and an anvil 2208 is firmly attached to the piezoelectric sensor 2206. A solenoid assembly 2220 containing an armature 2212 inserted without attachment into an electromagnetic coil 2210 is also included in the impulse and sensing head 2202. A pressure sensor 2214 may be attached to the head 2202 and configured so that when the probe 2204 is pressed against the patient's tissue and reaches a predetermined pressure, the pressure sensor 2214 causes a release of a burst of current to energize the electromagnetic coil 2210. When the electromagnetic coil 2210 is energized, the armature 2212 is accelerated to impact the anvil 2208 and thereby produce a force impulse, which travels through the piezoelectric sensor 2206 and probe 2204, thereby transmitting the force impulse to the tissues of the patient in contact with the probe 2204.

Figure 19A:
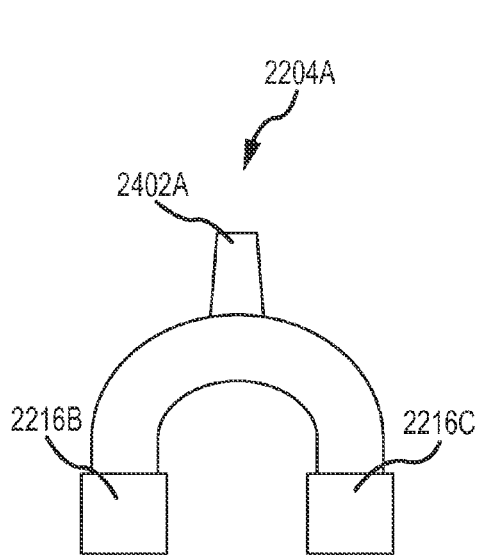
FIGS. 19A-19D are diagrams of embodiments of probes for an impulse stimulator instrument.
Figure 19B:
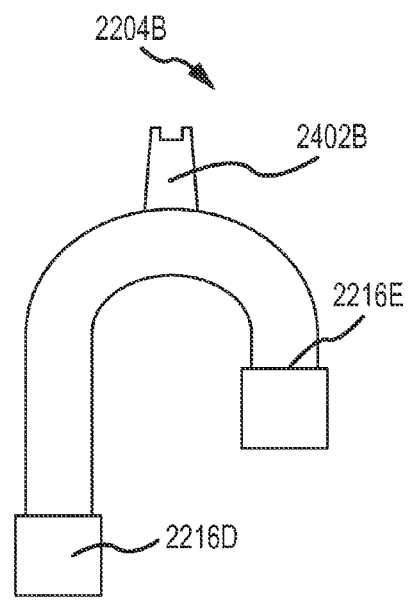

As illustrated in FIGS. 19A-19D, a variety of different configurations of probes 2204 may be employed with the impulse and sensing head 2202. For example, as illustrated in FIG. 19A, the dual-tipped probe 2204A may have a generally horseshoe shape ending in two laterally separated tips 2216B and 2216C; the tips 2216B and 2216C may be constructed of a soft material. The tips 2216B and 2216C may attach to a stem 2402A. The end of the stem 2402A opposite to the tips 2216B and 2216C may be coupled to the piezoelectric sensor 2206 (not shown) during use. The tips 2216B and 2216C of the dual-tipped probe 2204A may extend generally an even distance from the body 2402A. As shown in FIG. 19B, an alternative embodiment of a dual-tipped probe 2204B may have tips 2216D and 2216E that do not extend an even distance away from the body 2402B.

Figure 19C:
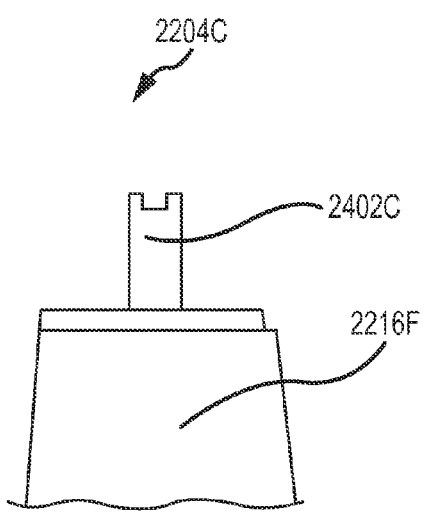

In another embodiment, illustrated in FIG. 19C, a single-tipped probe 2204C may include a single tip 2216F extending from the body 2402C. In an additional embodiment, shown in FIG. 19D, a single-tipped probe 2204D may include a single tip 2216G.

Figure 19D:
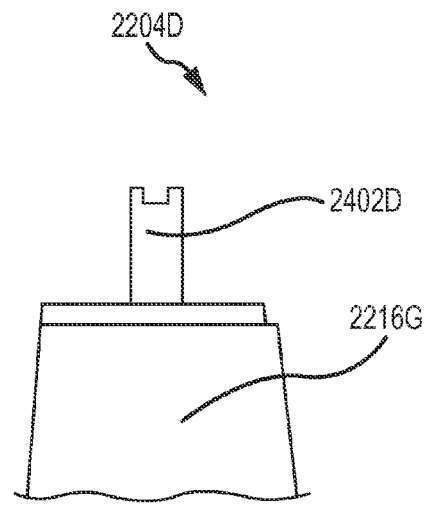

In general, the specific shapes and dimensions of the probe 2204 may vary amongst the embodiments. In an aspect, the tips 2216B and 2216C of the dual-tipped probe 2204A may extend away from the body 2402A to a greater or lesser extent than shown in FIG. 19A, or may be laterally separated a greater or lesser distance than that shown on FIG. 19A. In another aspect, the difference in tip lengths 2216D and 2216E may be greater or lesser than that shown in FIG. 19B. In an additional aspect, the length, width, and cross-sectional shape of the tip 2216F of the single-tipped probe 2204C may vary from the embodiment illustrated in FIG. 19C. In yet other aspects, the shape of the ends of the tips 2218 may generally vary amongst at least several shapes including a flat ended tip as illustrated in FIGS. 19C and 19D, a rounded or hemispherical tip as illustrated in FIGS. 19A and 19B, and any other known tip shape.

Referring back to FIG. 17, the impulse and sensing head 2202 may further include an elongated and generally cylindrical housing 2228 which has an insert 2230 that tapers to form a generally conical configuration at the forward end 2232. The other end of the housing 2228 is provided with a cylindrical closed end 2234. The housing 2228 and the closed end 2234 may be separately connected by a screw threaded connection to provide access into the interior of the housing 2228 and to separate the components of the impulse stimulator instrument 106 for repair, replacement and the like. After the housing 2228 is unscrewed from closed end 2234, it may slide back and insert 2230 may also be unscrewed from the housing 2228.

The design of the impulse stimulator instrument 106 also provides the ability to monitor the force impulses as they are applied to the tissues. The piezoelectric sensor 2206 may monitor the force impulses as they are applied to assess the response of the tissue of the patient to the application of the force impulses; the signals produced by the piezoelectric sensor 2206 may be output to the computing device 102 for processing by the tissue treatment application 120. The pressure sensor 2214 may output data characteristic of the pressure of the probe 2204 in contact with the tissue of the patient to the computing device 102 for processing by the tissue treatment application 120.

The impulse stimulator instrument 106 may obtain power from the computing device 102 via an electrical cable 2236. Alternatively, electrical power may be supplied through an additional electrical cord (not shown) that may be electrically connected to an external power supply, suitable electrical outlet, or the like, which extends into the housing 2228.

In an aspect, the impulse stimulator instrument 106 receives signals from the computing device 102 that control the production and delivery of force impulses in accordance with a treatment protocol selected and specified using the modules of the tissue treatment application 120 as described previously. A more detailed description of the design of the impulse stimulator instrument 106 in relation to the delivery of force impulses is provided below.

a. Force Impulse Production

In an aspect, the impulse stimulator instrument 106 is configured to develop and deliver a series of force impulses to the tissues of a patient, resulting in a percussive massage therapy. The probe 2204 of the impulse stimulator instrument 106 may oscillate by repetitively accelerating the armature 2212 to impact the anvil 2208 at a controlled frequency and a predetermined time period. Control signals received from the computing device 102 by the impulse stimulator instrument 106 via an electrical cable 2236 or other signal communication method control one or more characteristics of the force impulses. Non-limiting examples of characteristics of the force impulses include the frequency of production of the force impulses, the peak force of each force impulses, the duration of the series of force impulses.

In another aspect, the frequency of production of the force impulses may range between about 0.1 Hz and approximately 12 Hz. In an additional aspect, the frequency of production of the force impulses may be varied according to a predefined schedule received from the tissue treatment application 120. For example, the frequency of production of the force impulses may gradually increase from about 4 Hz to about 12 Hz in increments of about 0.1 Hz. In yet another aspect, the frequency of production of the force impulses may be continuously varied based on the analysis of measurements of tissue response to the force impulses performed by the tissue treatment application.

The force impulses are delivered to the tissues via the tips 2216 of the probe 2204 located at the forward end 2232 of the housing 2228. In an aspect, the tips 2216 may be cushioned for contacting the soft tissue to be treated. The probe 2204 may be constructed of a rigid material such as metal, plastic, or the like. The probe 2204 may screw into or frictionally insert into the piezoelectric sensor 2206. Different shaped probes 2204 may be used depending on the desired function of the impulse stimulator instrument 106. For example, if the impulse stimulator instrument 106 is measuring tissue response to force impulses, a different probe shape may be used compared to a probe 2204 used to implement a tissue treatment.

The housing 2228 contains a solenoid assembly 2220. The assembly 2220 includes an electromagnetic coil 2210 and an armature 2212 longitudinally reciprocally mounted without attachment within the coil 2210. The armature 2212 is configured so that the end of the armature 2212 will impact against the anvil 2208 when the electromagnetic coil 2210 is energized. The anvil 2212 is affixed to one side of a piezoelectric sensor 2206. The impact produces a force impulse which travels through the piezoelectric sensor 2206 and causes the piezoelectric sensor 2206 to generate a waveform.

When any one of the various probes 2204 is placed against the tissue of a patient, the end of the probe 2204 opposite to the patient resides firmly against the piezoelectric sensor 2206 which in turn resides firmly against the anvil 2208. In an aspect, a pressure sensor 2214 situated within the housing 2228 and interposed between the closed end 2234 of the housing 2228 and the solenoid assembly 2220 may control the initiation of a force impulse. The pressure sensor 2214 works in concert with each of the other components so that upon reaching exceeding a predetermined threshold pressure against the tissue of the patient, the pressure sensor 2214 signals the release of a burst of current that energizes the electromagnetic coil 2210, inducing the acceleration of the armature 2212 within the electromagnetic coil 2210 until the armature 2212 impacts the anvil 2208.

The impact of the armature 2212 against the anvil 2208 produces a force impulse which travels through the piezoelectric sensor 2206 in a direction essentially aligned with the movement of the armature 2212 just prior to impact. In an aspect, the direction of travel of the force impulse may be influenced by the resistive force of the probe 2204 applied to the piezoelectric sensor 2206 opposite to the anvil 2208. The resistive force results from the contact force of the probe 2204 and the patient's tissue.

The kinetic energy at the point of impact of the armature 2212 on the anvil 2208 causes the piezoelectric sensor 2206 to emit an electronic waveform which is characteristic of all of the force-producing Vectors of the electromechanical system situated on the anvil side of the piezoelectric sensor 2206 and opposed by the patient's tissues situated on the probe side of the piezoelectric sensor 2206. This electronic waveform may be received and processed by modules of the tissue treatment application 120 and may further be stored within the database 122.

The mass of the armature 2212 may be substantially equal to the mass of the anvil 2208 so that when the armature 2212 strikes the anvil 2208, the reactive force induced by impact of the armature 2212 is transferred to the tissue of the patient through the anvil 2208, piezoelectric sensor 2206, and attached probe 2204. The initial separation distance of the armature 2212 and anvil 2208 may be fixed by design, such that the kinetic energy and resulting impact force may be varied only by varying the velocity of the armature 2212 at the point of impact with the anvil 2208. The velocity of the armature 2212 may be varied by varying the inductive force of the electromagnetic coil 2210 on the armature 2212 by varying the magnetization time (excitations time) to the electromagnetic coil with constant voltage and current. 2210.

In one aspect, the solenoid assembly 2220 may be actuated by processing measurements from a pressure sensor 2214 and actuating the solenoid assembly 2220 when the measured pressure meets or exceeds a threshold pressure as described above. The pressure sensor 2214 may be any known pressure-sensing device including, but not limited to, a load cell.

In another aspect, the trigger point at which the solenoid assembly 2220 may be actuated by the movement of the housing 2228 relative to the solenoid assembly 2220 produced by pressing the probe tip 2216 against the tissue of the patient. This movement may be configured to complete an electrical circuit to the power supply of the solenoid assembly 2220 when a preset probe tip pressure is matched or exceeded. In an aspect, the preset pressure may be varied by varying the resistance of the relative movement of the housing 2228 to the probe tip pressure by incorporating a resilient element such as a spring between the structure of the housing 2228 and the support structure of the solenoid assembly 2220. In another aspect, the present pressure may be varied by varying the distance of relative movement needed to complete the electrical circuit to the power supply of the solenoid assembly 2220.

VII. Acoustic Oscillator (RF Generator Modulated by Acoustic (Audio) Modulator)

Referring again to FIG. 1, the tissue treatments of a patient 110 may be implemented using an acoustic oscillator 108. The acoustic oscillator 108 may be configured to deliver a series of acoustic pulses to the tissues of a patient. The operation of the acoustic oscillator is typically controlled by a GUI or other graphic display generated by the tissue treatment application 120.

Figure 21:
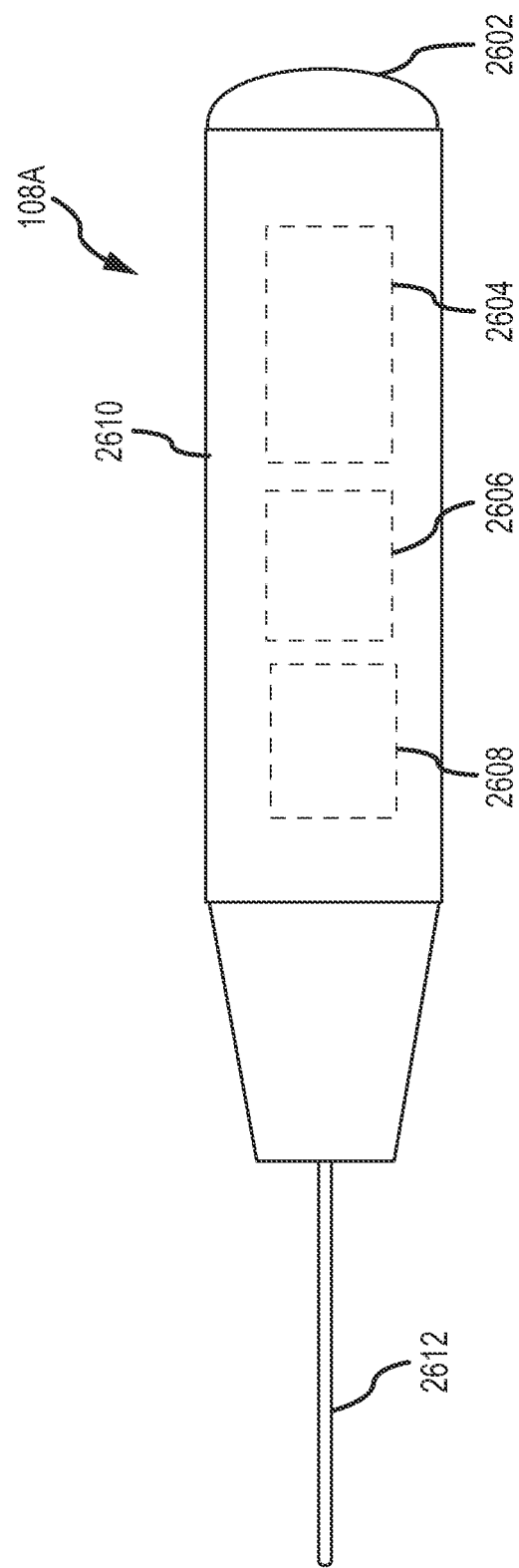
FIG. 21 is a cross-sectional side view of an acoustic oscillator.

An embodiment of an acoustic oscillator 108A is illustrated in FIG. 21. The acoustic coupler may include a transducer 2602 electrically connected to a band-pass filter and coupler 2604. An electrical oscillator 2608 and amplifier 2606 may supply the oscillating electrical signal used to drive the transducer 2602 at the desired frequency and amplitude. An electrical cable 2612 electrically connected to the computing device 102 supplies power to the acoustic oscillator. In addition, the electrical cable 2612 carries signals encoding data between the acoustic oscillator and the treatment application 120 resident on the computing device 102. A housing 2610 may contain the band-pass filter and coupler 2604, the electrical oscillator 2608 and the amplifier 2606. In addition, the transducer 2602 may be mounted to one end of the housing 2610, In an aspect, the acoustic oscillator 108 receives signals from the computing device 102 that control the production and delivery of acoustic pulses in accordance with a treatment protocol selected and specified using the modules of the tissue treatment application 120 as described previously. The acoustic oscillator 120 may receive instrument control settings generated by the tissue treatment application 120A including, but not limited to, the acoustic wave type, acoustic wave frequency, and acoustic wave amplitude within an acoustic pulse, the frequency of production of acoustic pulses, the duration of the series of acoustic pulses, and any other relevant instrument control settings.

In one aspect, the acoustic oscillator 108 may generate RF pulses having a frequency ranging between about 600 kHz and about 1.5 MHz. In another aspect, the acoustic oscillator 108 may generate acoustic pulses having a frequency of about 800 kHz. The form of the generated RF pulse may be any known RF waveform including, but not limited to, a sinusoidal waveform.

In another aspect, the pulse generation rate of the acoustic pulses may range between about 1 Hz and about 300 Hz. The amplitude or intensity of the acoustic pulses generated by the acoustic oscillator may correspond to sonic or ultrasonic oscillations in an additional aspect.

In another additional aspect, an acoustically conductive gel such as a water-based gel compound may be applied to the patient's hide to enhance the transmission efficiency of the acoustic pulses to the tissues of the animal patient.

XI. Administering RF Energy to Tissue at Optimal RF Frequency and Optimal Pulse Frequency In one embodiment of the system 100 of FIG. 1, the system 100 includes any of the above-described features and further includes a pressure wave system or module that is part of the system 100 of FIG. 1 and is used with the acoustic oscillator 108. Specifically, the pressure wave module may be in addition to or in place of the impulse stimulator instrument 106 and its supporting apparatus and algorithms. Such a pressure wave system or module 5010 is depicted diagrammatically in FIG. 22. In one embodiment, the pressure wave module 5010 and associated methods include the delivery of pressure waves (e.g., sound waves) 20 to a patient's tissue 25 in pulses that range in frequency of 1 Hz to 300 Hz for neurological stimulation. In other words, in one embodiment, a burst of pressure wave energy 20 is delivered to the patient's target tissue 25.

Figure 22:
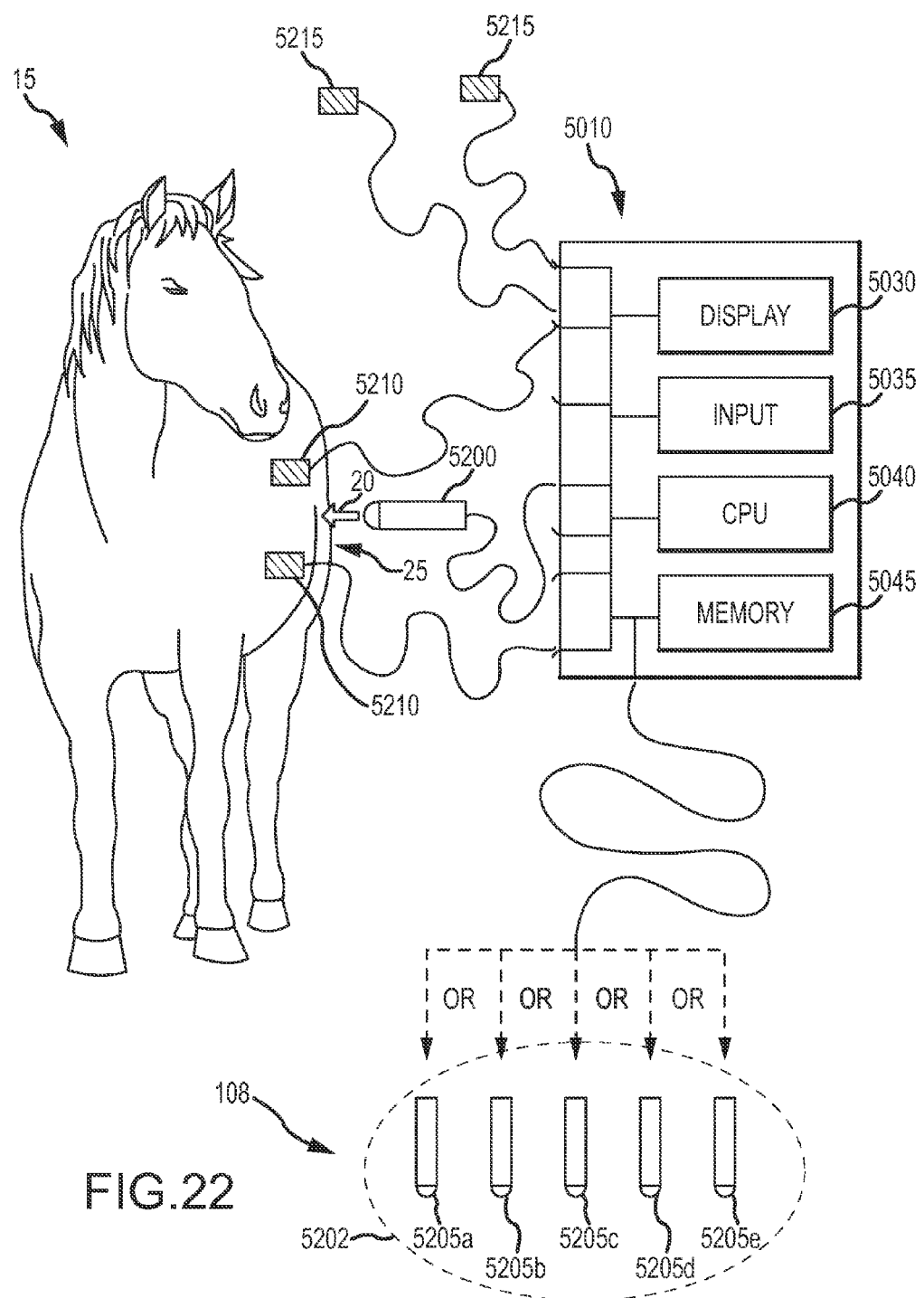
FIG. 22 is a schematic diagram of an alternative embodiment of the system being used on the patient.

As can be understood from FIG. 22, which is a schematic diagram of the system 5010 being used on the patient 15, the system includes a display 5030, an input 5035, a central processing unit (CPU) 5040, a memory 5045, and at least one pressure wave (RF energy) generator (e.g., sound wave generator) 108. The display may include a LCD or other type of screen for displaying information associated with the use of the system 5010 in treating a patient 15. For example, the display 5030 may display the patient's age, image, name, medical history, treatment durations, timing sequences, and protocols, and pressure wave shapes, frequencies, etc.

The input 5035 is in electrical communication with the display 5030 and may include a keyboard, touch screen, mouse, stylus, and/or other type of input mechanism. The input is configured to receive information associated with the treatment of the patient, such as patient age, tissue condition and location, desired treatment durations, timing sequences, and protocols, etc.

The CPU 5040 is in electrical communication with the display 5030, the input 5035, and memory 5045. The memory 5045 may include treatment parameters and protocols associated with the treatment of the patient such as, for example, pressure wave types, frequencies, magnitude, etc. for different types of patients, patient tissue, and tissue conditions.

The pressure wave generating device 108 is in electrical communication with the CPU 5040 and is configured to deliver a pressure wave (e.g., sound wave) to a tissue 25 of the patient 15, such as, for example, the head, neck, shoulders, hips, legs, or other anatomical regions of the animal patient. The pressure wave generating device 108 may be in the form of a handheld wand, as shown, or may be equipped with a strap or other arrangement to allow the pressure wave generating device 108 to be strapped to the patient 15. The pressure wave generating device 108 may be capable of generating a wide range of pressure energy (e.g., sound energy) 20, including ultrapressure (e.g., ultrasound), and short waves through long waves. In one embodiment, the pressure energy 20 generated by the pressure wave generating device 108 is a long wave pressure wave.

Typically, a conductive gel is applied to the patient's skin/hide tissue 25 to aid in the transmission of the pressure wave to the patient's underlying tissues and muscle. The pressure wave generating device 108 is configured to deliver a pressure wave having a frequency between 500 kHz and 1.5 MHz. In a preferred embodiment, the pressure wave generating device 108 delivers an 800 kHz pressure wave to the patient 15. Preferably, the pressure wave has sinusoidal waveform, although other waveforms and wave profiles may also be generated.

In various embodiments, the pressure wave generated by the pressure wave generating device 108 may be modulated to transmit the pressure wave throughout the patient's underlying tissues and muscle. For example, the pressure wave may be pulsed at a lower frequency. In one example, the pressure wave having a frequency between 500 kHz and 1.5 MHz may be pulsed at lower frequency between 1 Hz and to 300 Hz to transmit the energy of a pressure wave in frequencies known to evoke neurological potentials. The pulsing of the wave also reduces heat build up in the tissues and is intended to maximize the mechanical influence of the lower frequencies on the tissues and/or nerves.

Figure 28:
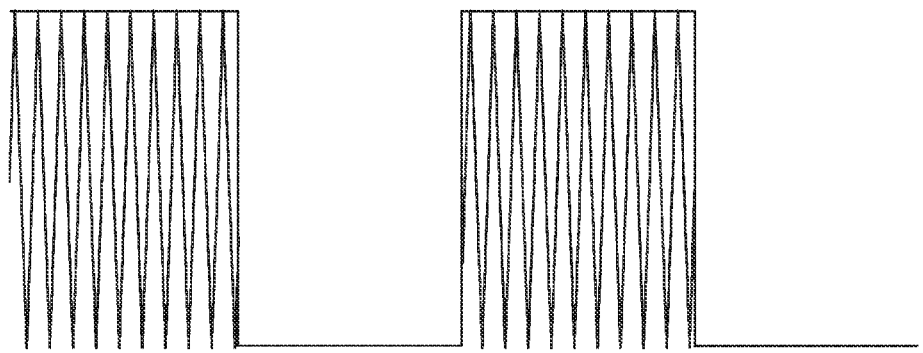
FIG. 28 is an example of a pulsed output signal similar to that depicted in FIG. 29.

The CPU 5040 causes the pressure wave-generating device 108 to generate a pressure wave of a desired frequency, magnitude, and duration to achieve neurological stimulation. For example, the pressure wave is achieved by introducing a pulsed pressure wave by pulsing an 800 MHz transmission wave in the frequency range of 1 Hz to 300 Hz in a sweep pattern so as to introduce all frequencies within the range within a programmable time period. The pressure wave may be generated continuously and modulated. FIG. 28 illustrates two types of patterns including amplitude modulation. Square waves or sinusoidal waves may be provided by the device.

Various embodiments of the system 5010 may contain more or less features according to the intended use and/or user of the system. For example, one embodiment of the system 5010 may be configured for home use by a patient. This embodiment of the system 5010 may not have extensive monitoring equipment. Conversely, another embodiment of the system 10 may be provided for clinical use. A clinical embodiment of the system 5010 may include all of the disclosed monitoring devices, as well as other monitoring equipment or medical devices as desired by a medical professional. The disclosed system and method is advantageous in that it stimulates the nervous system and circulatory system, thereby improving the function, appearance and health of patient tissue.

In one embodiment, the system and method may include administering RF energy to patient tissue at a RF frequency determined to have the highest transmissibility in the tissue and at a pulse frequency determined to result in the highest electromyogram reading. As a result, the administration of the RF energy occurs at a RF frequency that will cause the RF energy to travel the greatest distance through the patient tissue, and the administration of the RF energy will be tailored to provide the most beneficial nerve stimulation.

As can be understood from FIG. 22, the system may also include an evaluation RF head 5200, a pressure wave generating device 108, a RF antenna(s) 5210, and an EMG sensor(s) 5215. The pressure wave generating device 108 may be in the form of a plurality 5202 of treatment RF heads 5205a-g. The evaluation RF head 5200 and RF antenna and/or and acoustic measuring device 5210 are capable of being placed in electrical communication with the CPU 5040.

Figure 23:
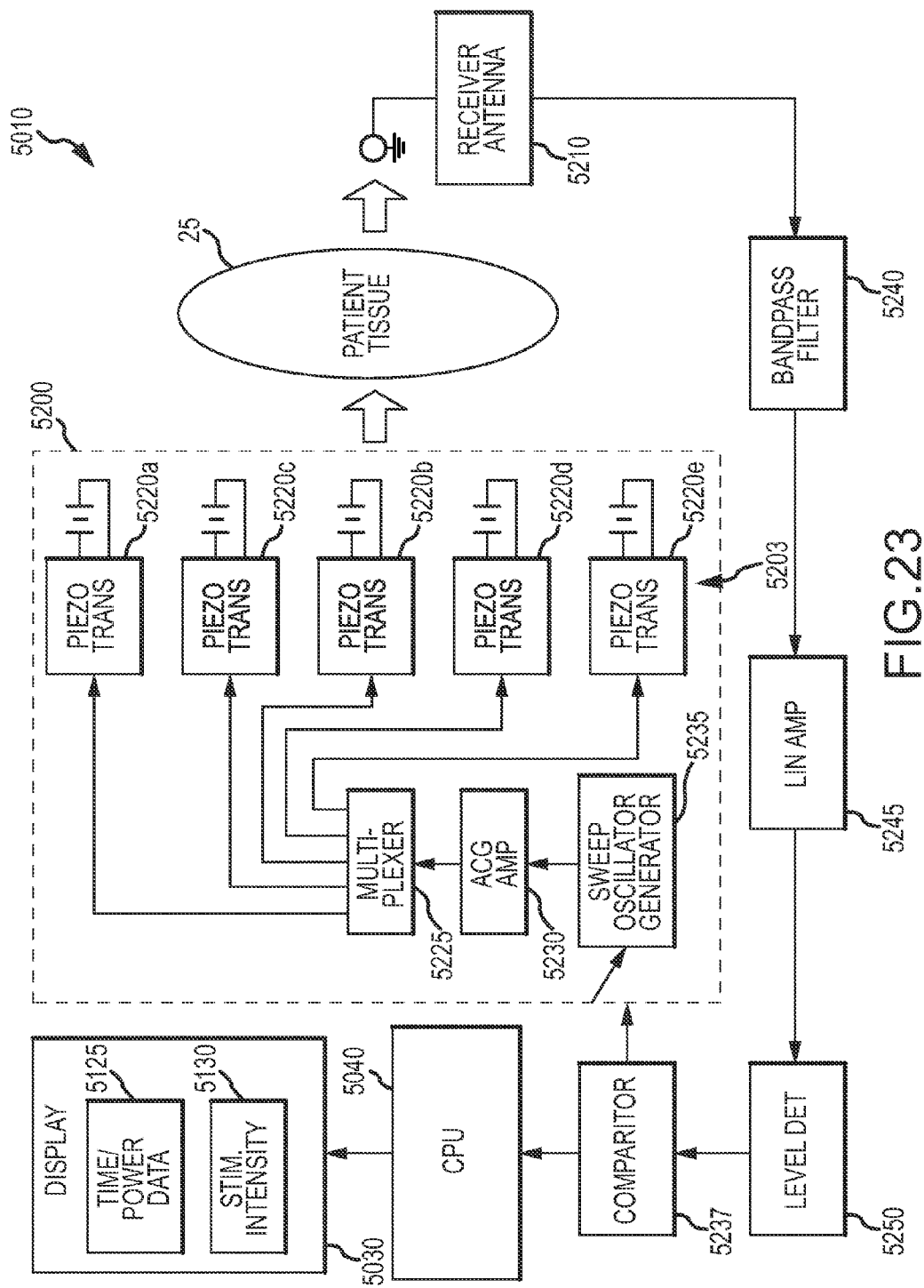
FIG. 23 is a schematic diagram of the system employing the evaluation RF head and the RF antenna for the embodiment of the system depicted in FIG. 22.

As illustrated in FIG. 23, which is a schematic diagram of the system 5010 employing the evaluation RF head 5200 and the RF antenna(s) 5210, the evaluation RF head 5200 includes an array 5203 of piezoelectric transducers 5220a-e electrically coupled to a multi-plexer or pulse control 5225 that is electrically coupled to an automatic gain control amplifier 5230 electrically coupled to a sweep oscillator generator 5235. The evaluation RF head 5200 is electrically coupled to a comparator 5237 that is electrically coupled to the CPU 5040 and display 5030.

Each piezoelectric transducer 5220a-e of the array 5203 is individually tuned to generate RF energy at a distinct frequency as compared to the other piezoelectric transducers of the array. The piezoelectric transducers 5220a-e forming the array 5203 of the evaluation RF head 5200 provide a range of distinct RF energy frequencies over a range of between approximately 500 KHz and approximately 1.5 MHz at steps of between approximately 50 KHz and approximately 200 KHz. For example, a first piezoelectric transducer 5220a may be tuned to 500 KHz, the second piezoelectric transducer 5220b may be tuned to 600 KHz, and so forth through the rest of the piezoelectric transducers such that the array 5203 is capable of providing RF energy at a frequency range of between approximately 500 KHz and 1.5 MHz with steps of 100 KHz, resulting in an array 5203 having 11 individually tuned piezoelectric transducers. Thus, the array 5203 is configured to generate RF energy over a range of frequencies not possible via a single piezoelectric transducer.

As can be understood from FIG. 23, the RF receiver antenna(s) 5210 is electrically coupled to a bandpass filter 5240 that is electrically coupled to a linear amplifier 5245 electrically coupled to a level detector 5250 electrically coupled to the comparator 5237. As indicated in FIGS. 22 and 23, the evaluation RF head 5200 is applied to animal patient tissue, and the RF receiver antenna(s) and or acoustic measuring device(s) 5210 is applied to another region of animal patient tissue at a different location spaced apart from the location where the head 5200 is being applied to the patient tissue. The RF receiver antenna(s) is configured to detect RF energy transmitted through the patient tissue from the evaluation RF head 5200. For example, as indicated in FIG. 22, where the tissue target location for the administration of the treatment is an rib or side region of the animal patient, which in this example is a horse, but can be any other type of animal, RF receiver antennas 5210 could be attached to the patient's hide on the on the side chest region above and below a target treatment area 25.

When the evaluation RF head 5200 and RF receiver antenna(s) 5210 are applied to the patient tissue, the system 5010 is configured to cause the evaluation RF head 5200 to administer RF energy to the patient tissue over a range of RF frequencies by the sweep oscillator generator 5235 generating a series of frequencies in a step fashion across the range of frequencies of the array 5203 and the multi-plexer 5225 sending the appropriate stepped frequency to the appropriate piezoelectric transducer 5220a-5220e when the appropriate stepped frequency is generated by the oscillator generator 5235. As the array 5203 of the head 5200 sweeps through the various frequencies, the RF receiver antenna(s) 5210 senses the administered RF energy transmitted through the patient. The comparator 5237, in conjunction with the CPU 5040, identifies which RF frequency of the range of RF frequencies administered to the patient via the array 5203 of the head 5200 has the most transmissitivity through the patient. The system 5010, via, for example, the display 5030, recommends a treatment RF head from the plurality 5202 of treatment RF heads 5205a-5205e that is capable of providing the identified RF frequency.

Each treatment RF head 5205a-5205e of the plurality 5202 treatment RF heads shown in FIG. 22 has a piezoelectric transducer tuned to a unique frequency different from those of the other heads 5205a-5205e. Thus, the plurality 5202 of treatment heads 5205a-5205e may be made up of a sufficient variety of treatment RF heads so as to cover a range of RF frequencies in a stepped fashion. For example, treatment RF head 5205a-5205e of the plurality 5202 is individually tuned to generate RF energy at a distinct frequency as compared to the other heads 5205a-5205e of the plurality 5202. The heads 5205a-5205e of the plurality 5202 provide a range of distinct RF energy frequencies over a range of between approximately 500 KHz and approximately 1.5 MHz at steps of between approximately 50 KHz and approximately 200 KHz. For example, the first treatment RF head 5205a may have a piezoelectric transducer tuned to 500 KHz, the second treatment RF head 5205b may have a piezoelectric transducer 5300 may be tuned to 600 KHz, and so forth through the rest of the treatment RF heads such that the plurality 5202 of treatment heads 5205a-5205e is capable of providing RF energy at a frequency range of between approximately 500 KHz and 1.5 MHz with steps of 100 KHz, resulting in plurality 5202 having 11 individually tuned treatment RF heads. Thus, a treatment RF head 5205a-5205e can be selected from the plurality 5202 to match the RF frequency identified via the array 5203 and comparator 5237 as discussed above with respect to FIG. 22.

Figure 24:
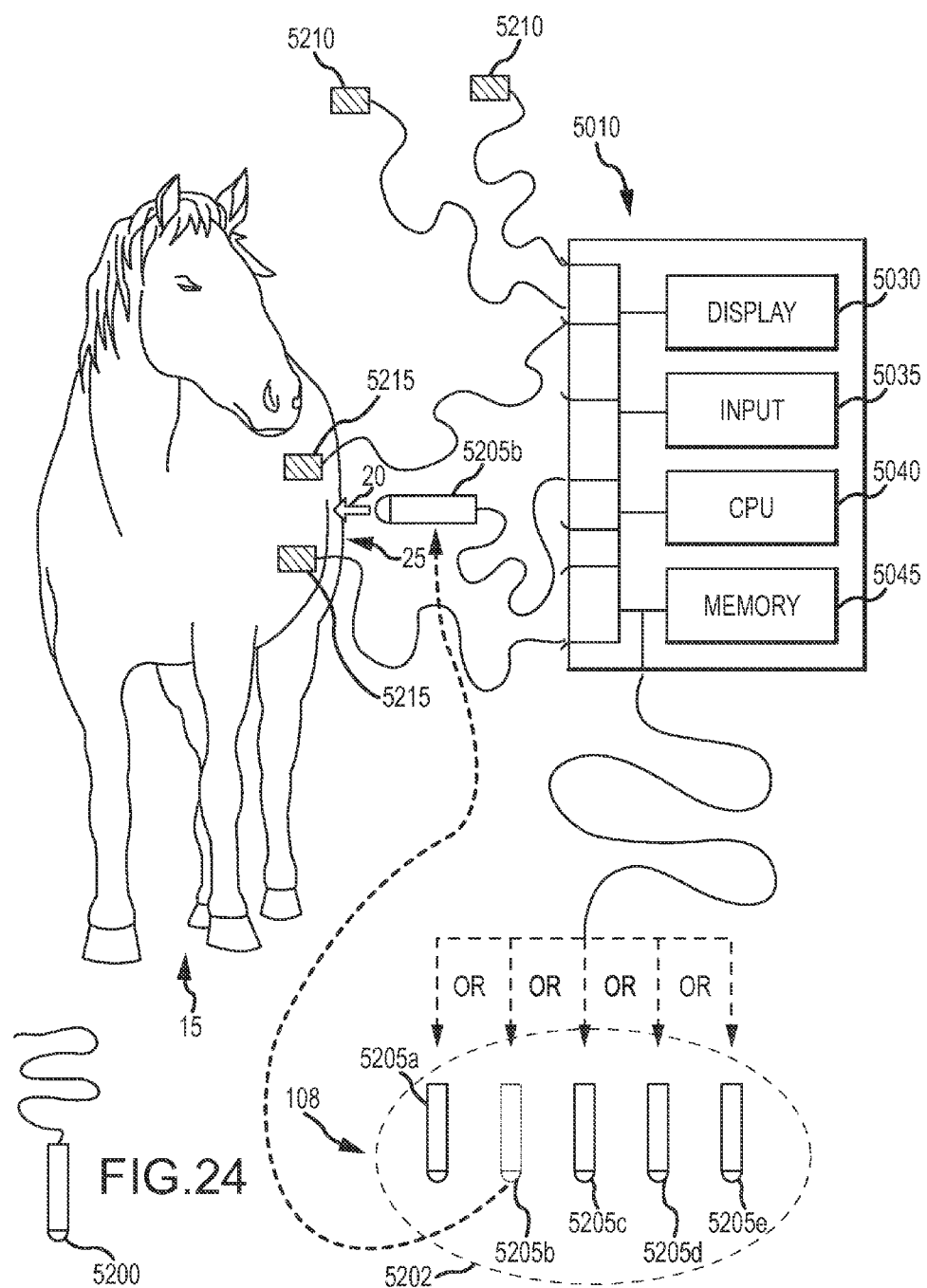
FIG. 24 is a schematic diagram of the system embodiment of FIG. 22, where the selected treatment RF head and EMG sensor are coupled to the system and being applied to the patient.

Once a treatment RF head 5205a-5205e is selected from the plurality 5202 that matches the identified RF frequency, the selected RF treatment head is electrically coupled to the system 5010, as illustrated in FIG. 24. For example, by using the array 5203 and comparator 5237 as described above with respect to FIG. 22, it is determined that a frequency of 600 KHz has the greatest transmissibility through the patient tissue 25 and, as a result, the system 5010 recommends from the plurality 5202 of heads the treatment RF head 5205b, which is tuned to operate at 600 KHz. As shown in FIG. 24, the treatment RF head 5205b is electrically coupled to the system 5010, and the EMG sensor(s) 5215 is electrically coupled to the system 5010. The treatment RF head 5205b and EMG sensor(s) 5215 are both applied to the patient tissue 25.

Figure 25:
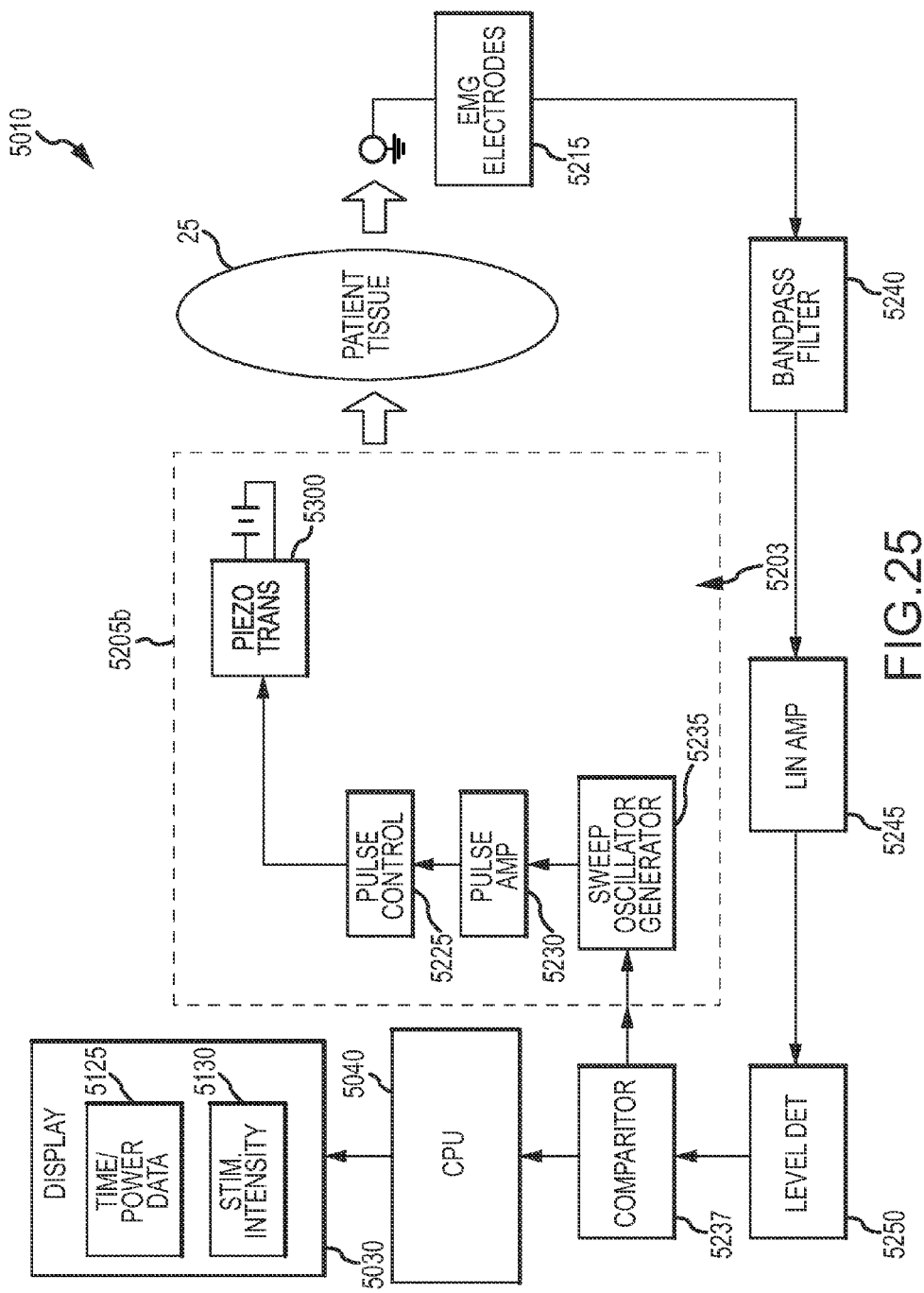
FIG. 25 is a schematic diagram of the system employing the selected treatment RF head and the EMG sensor for the embodiment of the system depicted in FIG. 24.

The system 5010 now appears as schematically depicted in FIG. 25. Specifically, the selected treatment RF head 5205*b* includes piezoelectric transducer 5300 electrically coupled to a pulse control 5225 that is electrically coupled to a pulse amplifier 5230 electrically coupled to a sweep oscillator generator 5235. The treatment RF head 205*b* is electrically coupled to a comparator 5237 that is electrically coupled to the CPU 5040 and display 5030 described above with respect to FIG. 22.

As can be understood from FIG. 25, the EMG sensor 5215, which has electrodes, is electrically coupled to a bandpass filter 5240 that is electrically coupled to a linear amplifier 5245 electrically coupled to a level detector 5250 electrically coupled to a comparator 5237. As indicated in FIGS. 24 and 25, the treatment RF head 5205*b* is applied to patient tissue 25, and the EMG sensor(s) 5215 is applied to patient tissue 25 at a different location spaced apart from the location where the head 5205*b* is being applied to the patient tissue. The EMG sensor(s) is configured to detect electromyogram in the patient tissue 25 from resulting from RF energy administered to the patient tissue via the treatment RF head 5205*b*. For example, as indicated in FIG. 24, where the tissue target location for the administration of the treatment is an rib or side region of the animal patient, which in this example is a horse, but can be any other type of animal, EMG sensors 5215 could be attached to the patient's hide on the on the side chest region above and below a target treatment area 25.

When the treatment RF head 5205*b* and EMG sensor(s) 5215 are applied to the patient tissue, the system 5010 is configured to cause the treatment RF head 5205*b* to administer RF energy to the patient tissue at the identified RF frequency (which is 600 KHz in this example) over a range of pulse frequencies by the sweep oscillator generator 5235 and pulse control 5225 causing the administered 600 KHz RF energy to pulse at a series of frequencies in a step fashion across a range of pulse frequencies generated by the oscillator generator 5235. In one embodiment, the generator 5235 is configured to cause the treatment RF head 5205*b* to administer RF energy at the identified RF frequency (which is 600 KHz in this example) to the patient over a range of pulse frequencies between approximately 1 Hz and approximately 300 Hz at steps that are defined in the software via an algorithm that allows the user to determine the scan time, in one embodiment, between approximately 1 Hz and approximately 30 Hz. Optimum scan times are established for each tissue type, animal type, treatment location, and tissue condition in a database from empirical data. For example, a database contained in the memory of the system can be used to pre-select scan times based on the tissue or area of concern entered into the interface of the system, each tissue type or area of concern being correlated in the data base to specific scan times.

Figure 27:
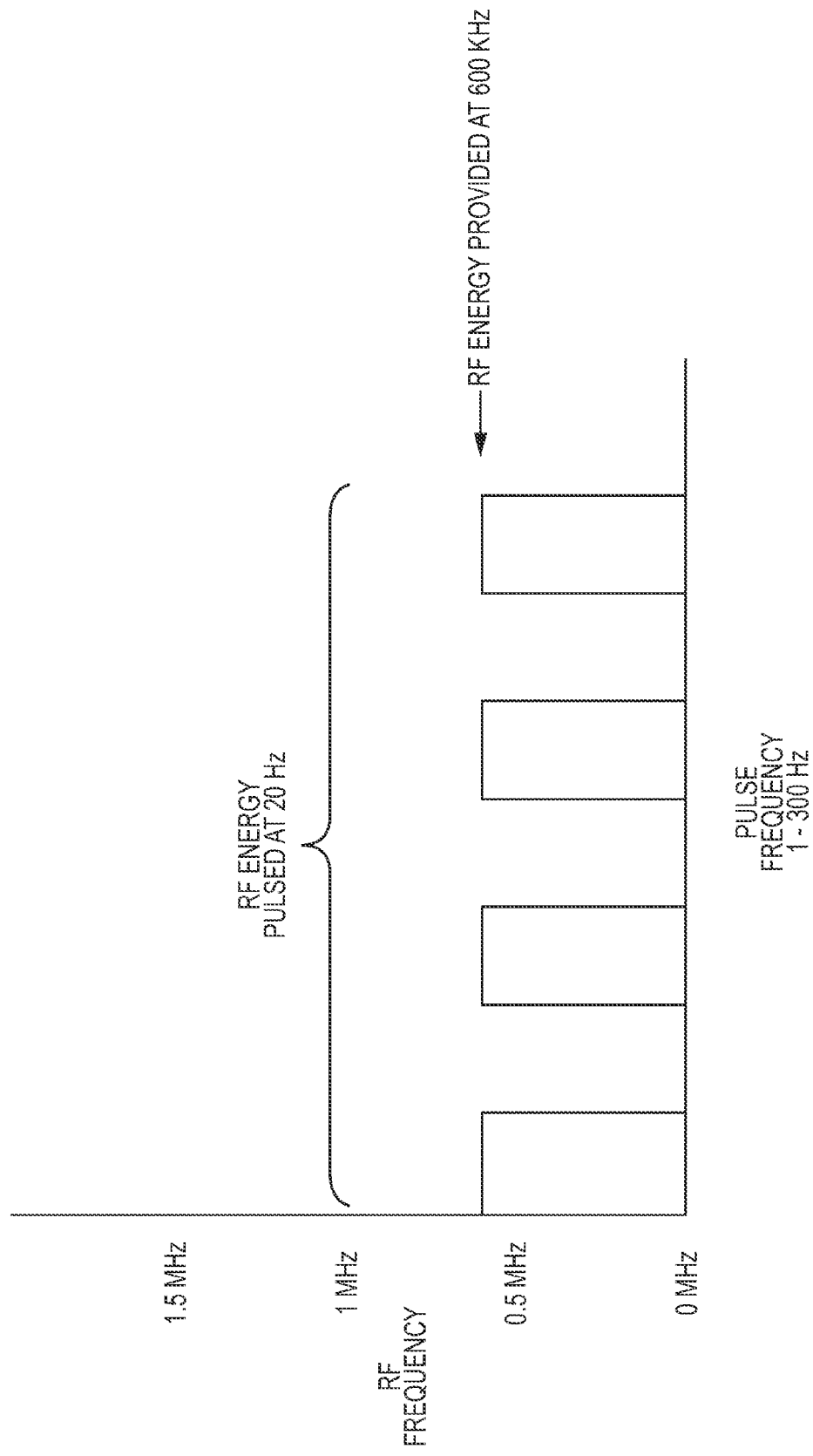
FIG. 27 is a graph of RF energy being administered at an example identified (optimum) RF frequency and pulsed at an example identified (optimum) pulse frequency.
Figure 29:
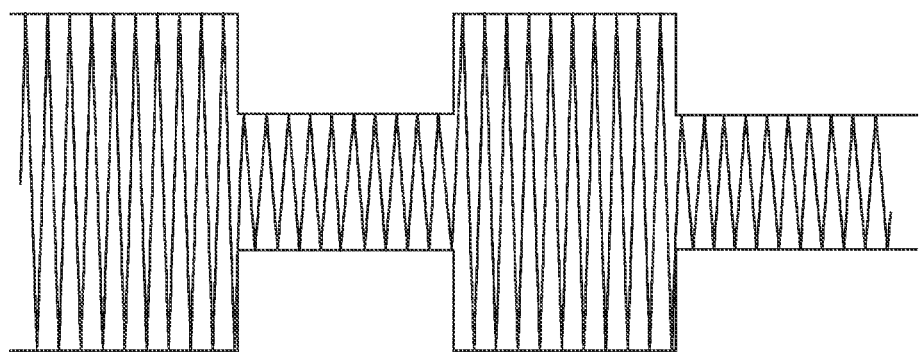
FIG. 29 is an example of a modulated output signal.

As the generator 5235 causes the head 5205*b* to sweep through the various frequencies, the EMG sensor(s) 5215 senses the resulting electromyogram in the patient. The comparator 5237, in conjunction with the CPU 5040, identifies which pulse frequency of the range of pulse frequencies administered to the patient via the generator 5235 and head 5205*b* has the highest electromyogram reading in the patient. The system 5010, via, for example, the display 5030, recommends a treatment pulse frequency setting from the plurality of treatment pulse frequencies available to the treatment head 5205*b* via the generator 5235. For example, the EMG sensor and comparator work together to determine a pulse frequency of 20 Hz resulted in the highest electromyogram readings in the patient. Accordingly, the system 5010 recommends using the treatment RF head 5205*b* to administer 600 KHz RF energy at a 20 Hz pulse frequency (i.e., the 600 KHz RF energy is pulsed at 20 Hz when being administered to the patient tissue). FIG. 27 illustrates a graph of RF energy being administered at the identified (optimum) RF frequency of 600 KHz and pulsed at the identified (optimum) pulse frequency of 20 Hz, as used in this example. FIG. 28 is an example of a pulsed output signal similar to that depicted in FIG. 27. FIG. 29 is an example of a modulated output signal. In some embodiments of the system, the RF energy can be administered at an identified (optimum) RF frequency (e.g., 600 Hz) and pulsed at the identified (optimum) pulse frequency (e.g., 20 Hz) such that the RF energy is pulsed similar to that depicted in FIG. 28. In some embodiments, the RF energy at the identified RF frequency may be modulated at the identified pulse frequency similar to that depicted in FIG. 29.

Figure 26:
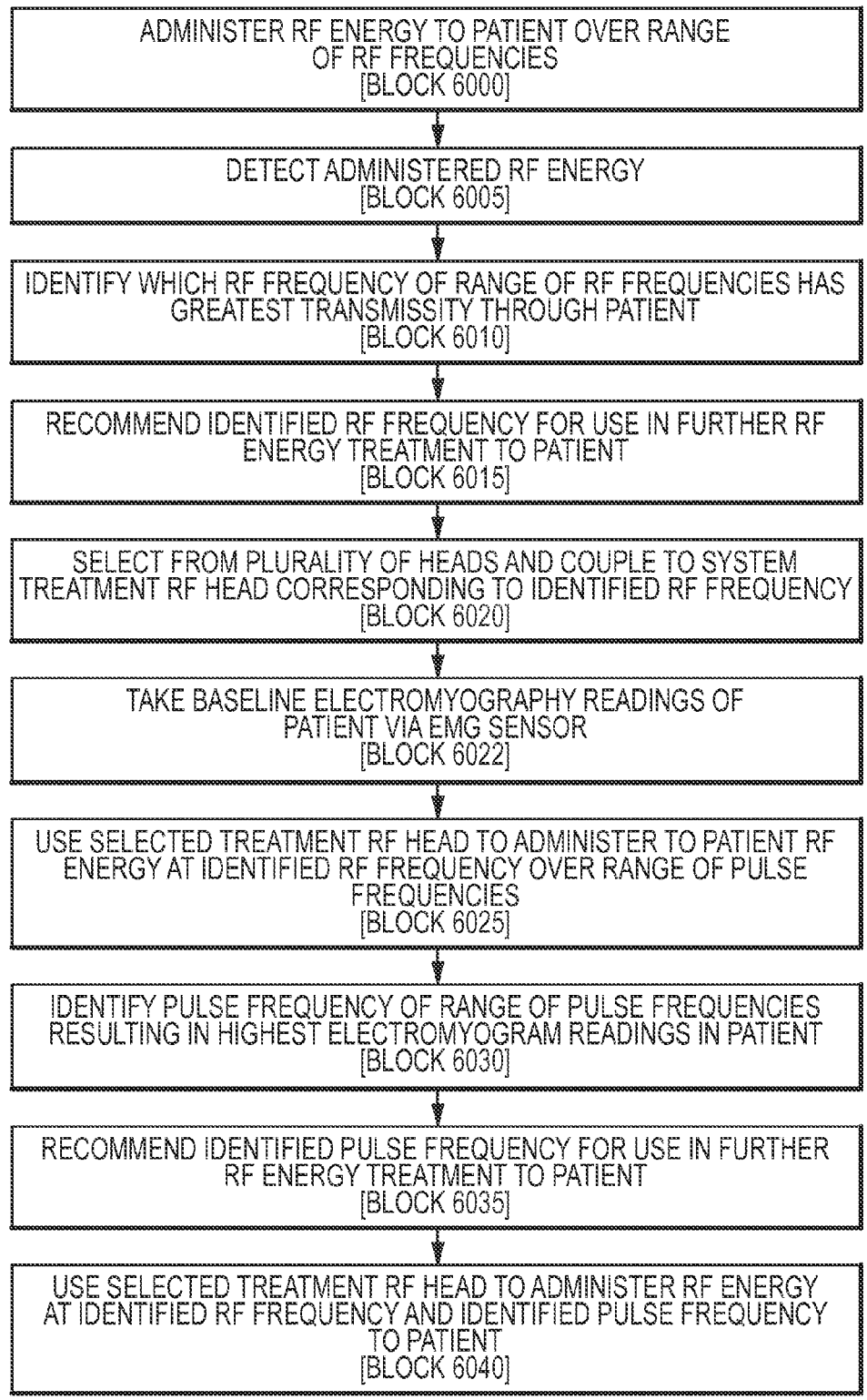
FIG. 26 is a flow chart illustrating an operational method associated with the system embodiment of FIGS. 22-25.

As can be understood from the preceding discussion regarding FIGS. 22-25, a method is disclosed where RF energy is applied to the patient tissue at a more transmissible RF frequency and at a pulse frequency that results in the highest electromyogram readings. For example, as can be understood from FIG. 26, via the transducer array 5203 of the evaluation RF head 5200, RF energy is administered to the patient over a range of RF frequencies [block 6000]. Via the RF receiver antenna and/or acoustic measuring device(s) 5210, the administered RF energy is detected [block 6005]. The CPU 5040 and comparator 5237 identifying which RF frequency of the range of RF frequencies has the greatest transmissibility through the patient [block 6010]. The display 5030 recommends the identified RF frequency for use in further RF energy treatment to the patient [block 6015]. The applicable treatment RF head 5205*b* corresponding to the identified RF frequency is selected from the plurality 5202 of heads and coupled to the system 5010 [block 6020]. Baseline electromyography readings are taken of the patient via the EMG sensor(s) 5215 [block 6022] followed by using the selected treatment RF head 5205*b* to administer to the patient the RF energy at the identified RF frequency over a range of pulse frequencies [block 6025]. The EMG sensor(s) 5215, the comparator 5237 and CPU 5040 are used to identify the pulse frequency of the range of pulse frequencies resulting in the highest electromyogram readings in the patient [block 6030], and the display 5030 recommends the identified pulse frequency for use in further RF energy treatment to the patient [block 6035]. The selected treatment RF head 5205*b* is then used to administer the RF energy at the identified RF frequency and identified pulse frequency to the patient [block 6040].

While the system embodiment discussed above with respect to FIGS. 22-26 applies to patient tissue RF energy at an identified RF frequency and identified pulse frequency, in some embodiments, the system 5010 will apply an identified RF frequency over a range of stepped amplitudes instead of over a range of stepped pulse frequencies. Accordingly, once a specific stepped amplitude is identified as resulting in the highest EMG reading, the RF energy can be applied to the patient tissue at the identified RF frequency and identified amplitude.

By administering the RF energy to the patient tissue at an identified RF frequency and identified pulse frequency, the RF energy can be tailored to travel the greatest distance possible through the patient tissue at a pulse frequency that provides the greatest therapeutic result, as indicated by the EMG sensor readings, which give an instantaneous feedback of the therapeutic impact of the RF energy, such instantaneous feedback being less likely to be obtained via tissue temperature readings, tissue oxygenation readings, or other measurements. Over time and the course of treatment via the system 10, the patient tissue characteristics may change with respect to the RF frequency and/or the pulse frequency believed to be optimal for the therapeutic affect. Accordingly, the methodology outlined in FIG. 26 can be reapplied to identify a new optimal RF frequency, which will require the selection of a new treatment RF head from the plurality of such heads. Also, the new treatment RF head and above described methodology can be used to identify a new optimal pulse frequency. The system can then be used to administer the RF energy to the patient tissue at the new optimal RF and pulse frequencies.

Applying the pulsed RF energy to the patient tissue is advantageous in that it creates corresponding waves that travel through the patient tissue to release their energy at boundary layers such as, for example, facia, muscle, tendons or bone, etc. that are highly innervated. This release of mechanical energy at the boundary layers stimulates the nervous and vascular system, thereby providing a therapeutic benefit for tissues typically the focus of traditional veterinarian medicine and animal patient physical therapy. Pulsing the RF energy at the optimal RF frequency also reduces tissue heating as compared to continuously applied RF energy at the optimal RF frequency.

Figure 30:
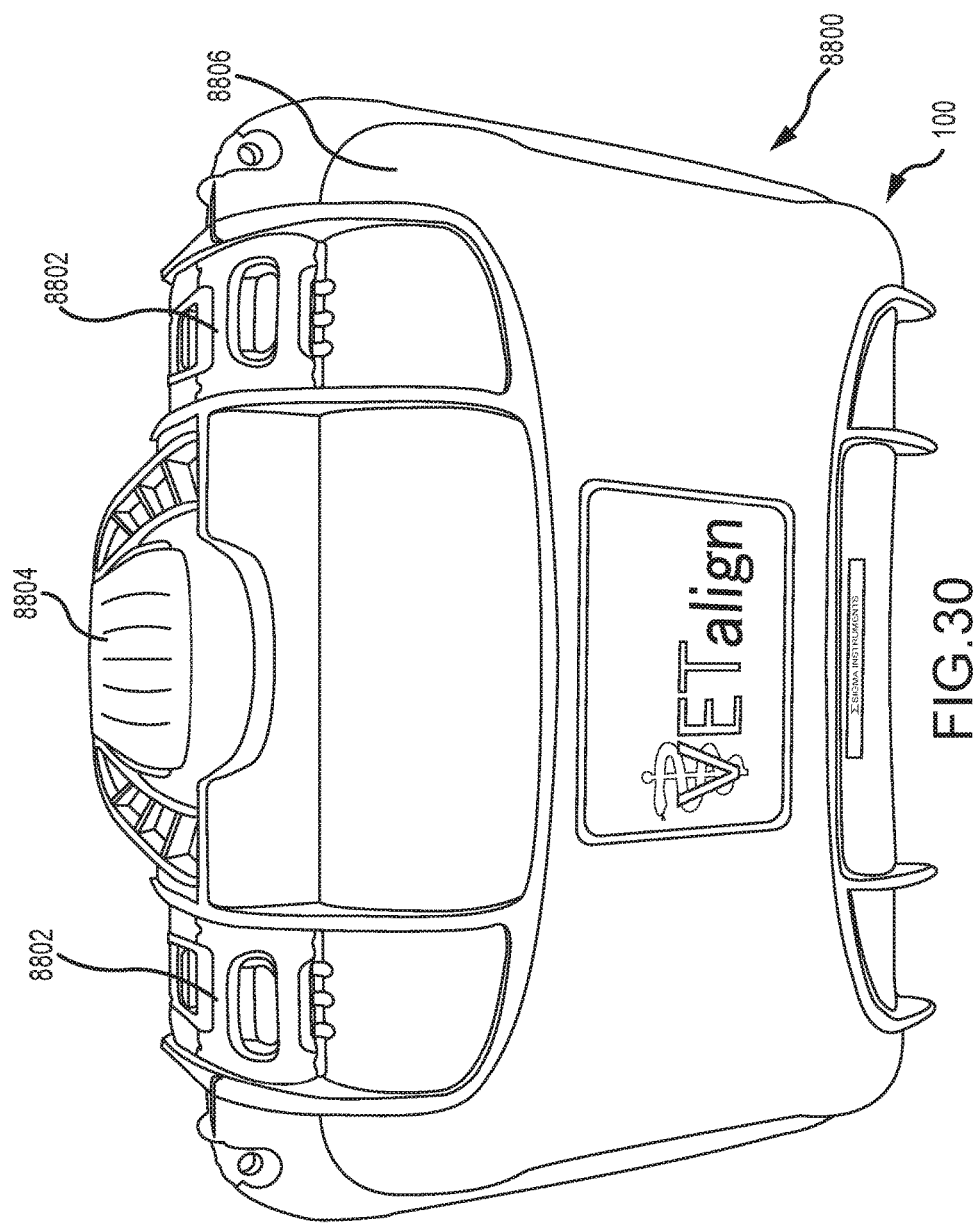
FIG. 30 is an isometric view of an embodiment of the veterinarian treatment system for treating the tissue of an animal patient, where a case or housing that encloses and protects the system is closed.

As illustrated in FIG. 30, which is an isometric view of an embodiment of the veterinarian treatment system 100 for treating the tissue of an animal patient, the system 100 may include a case or housing 8800 that encloses and protects the system. The case 8800 may be secured in a closed state via latches 8802 as illustrated in FIG. 30. The case 8800 may also include a handle 8804 that extends from the sidewalls or shell 8806 of the case.

Figure 31:
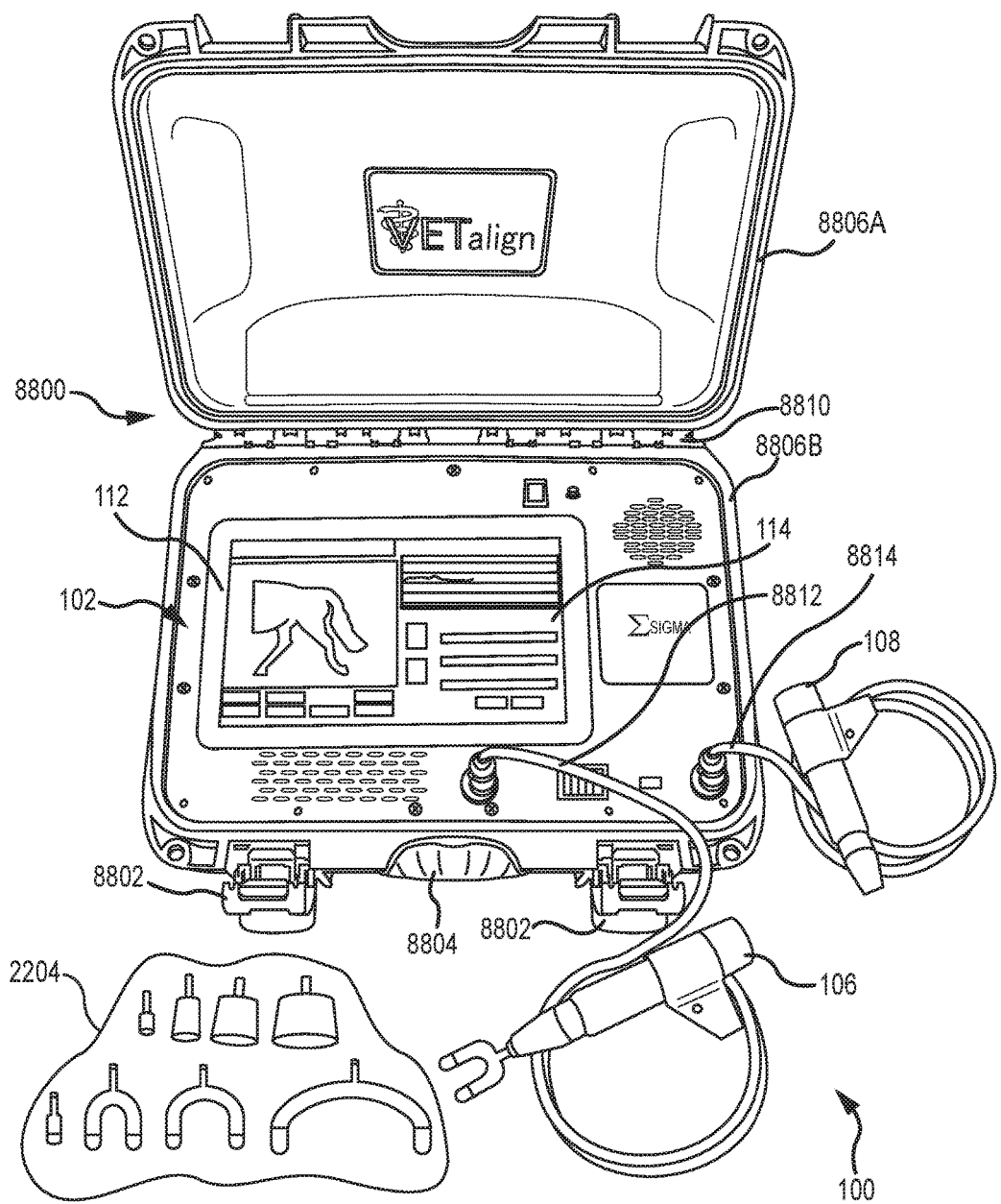
FIG. 31 is an isometric view of the veterinarian treatment system of FIG. 30, where the case or housing is opened up to reveal the display, input device, impulse stimulator instrument and acoustic oscillator.

As shown in FIG. 31, which is an isometric view of the veterinarian treatment system of FIG. 30 with the case 8800 opened up to reveal the display 112 and input device 114, the case 8800 has a clamshell arrangement with a top sidewall 8806A and a bottom sidewall 8806B pivotally secured to each other via a hinge 8810. The computing device 102 of the system 100, along with the display 116 and input device 114 are contained in the bottom sidewall 8806B. The computing device 102 may be as described above with respect to configuration, components and operation.

The system 100 may include the impulse stimulator instrument 106 and/or the acoustic oscillator 108. The impulse stimulator instrument 106 may be as described above with respect to configuration, components and operation. The impulse stimulator instrument 106 is capable of being electrically coupled to the computing device 102 via an electrical cable 8812. Multiple types of probes 2204 similar to those described above are provided for coupling to the impulse stimulator instrument 106.

The acoustic oscillator 108 may be as described above with respect to configuration, components and operation. The acoustic oscillator 108 is capable of being electrically coupled to the computing device 102 via an electrical cable 8814.

Figure 32:
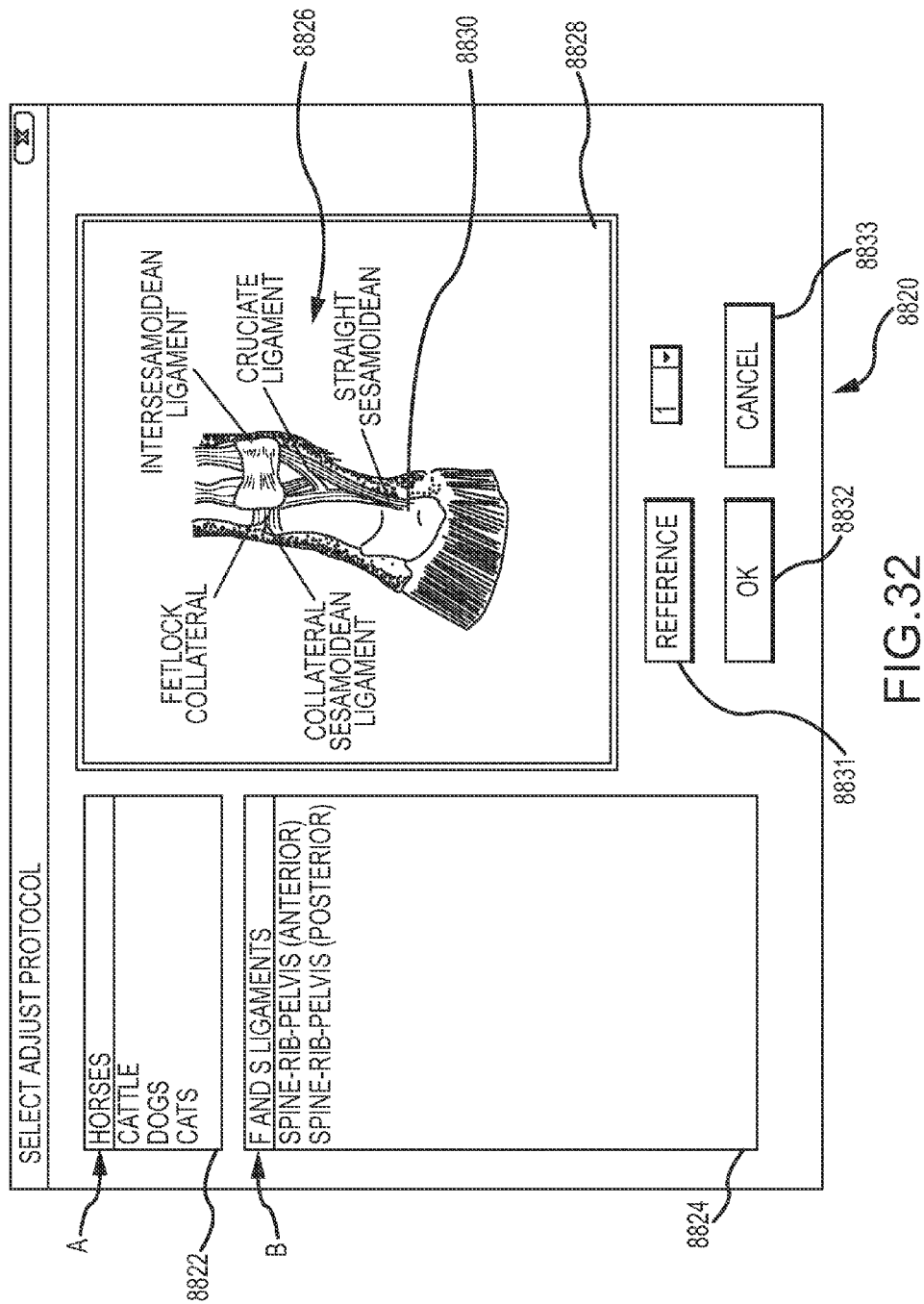
FIG. 32 depicts a GUI for display on the display depicted in FIG. 31, where the GUI is associated with the setup of the system for the treatment of a horse.

FIG. 32 depicts a GUI 8820 for display on the display 112 depicted in FIG. 31, where the GUI 8820 is associated with the setup of the system 100 for the treatment of a horse. As shown in FIG. 32, the GUI 8820 includes an animal selection window 8822, where "Horses" has already been selected from other listed animals, as indicated at Arrow A. The GUI 8820 also includes a treatment region selection window 8824, where "F and S Ligaments" has already been selected from other listed treatment regions applicable to horses, as indicated by Arrow B. As a result of the selection of the "F and S Ligaments" at Arrow B in window 8824, an image 8826 of a horse hoof and ankle region is depicted in an image window 8828. A trigger point 8830 for an associated treatment is shown in the image 8826. Touch sensitive screen buttons "Reference", "OK" and "Cancel" 8831-8833 are also included in the GUI 8820. In one embodiment, the "OK" button 8832 is selected to begin treatment. The "Reference Button" 8831 is used to store information regarding the anatomical area of treatment, treatment overview and rationale, treatment goals and or expected responses. In one embodiment, useful reference information may be accessed by the operator by selecting button 8831. Pressing button 8832 will return to the treatment screen and setup the system using the settings found in the selected treatment protocol. Pressing button 8833 will cause the selection screen to return to the treatment screen in its last mode.

Figure 33:
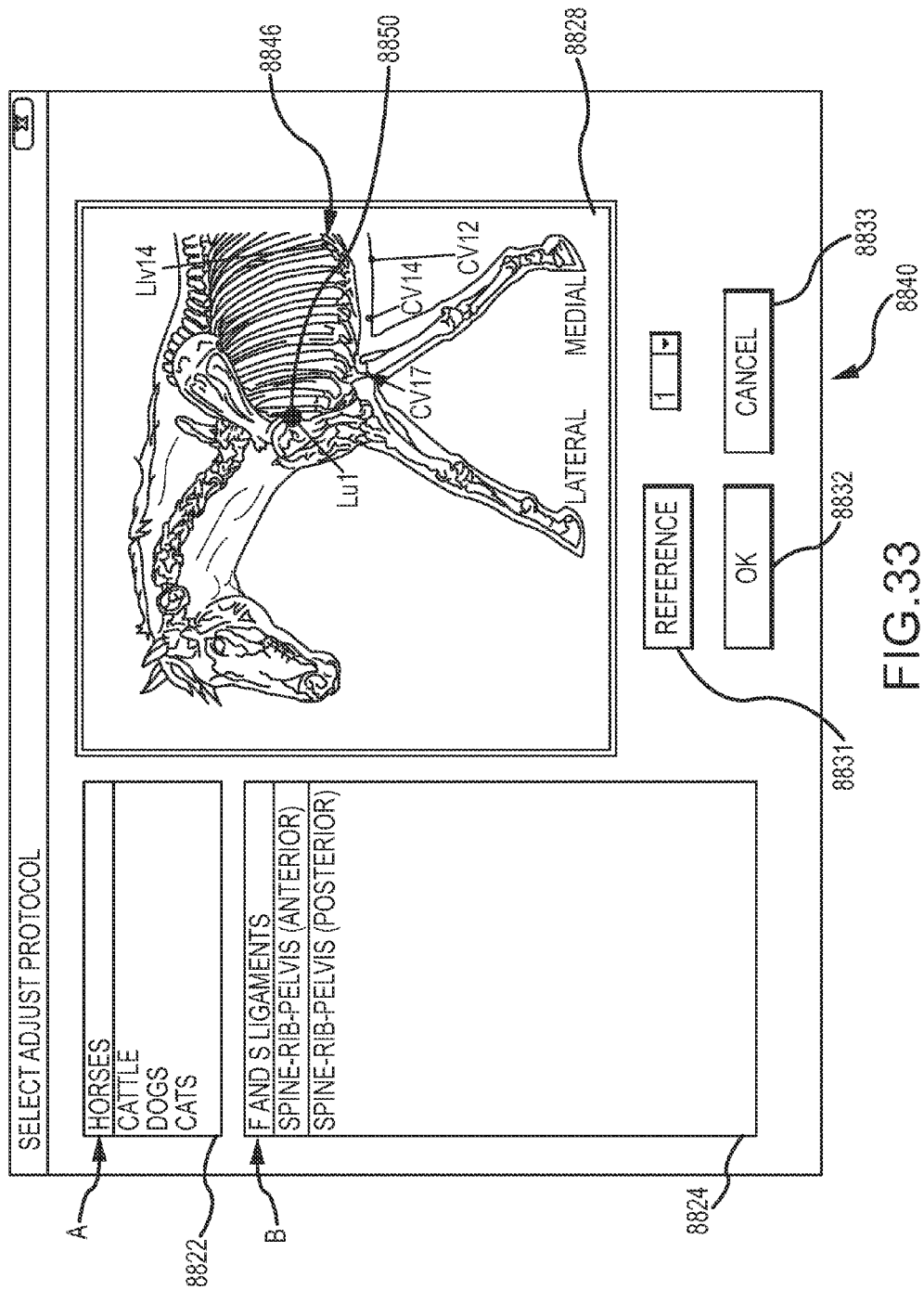
FIG. 33 depicts another GUI for display on the display depicted in FIG. 31, where the GUI is associated with the setup of the system for the treatment of a horse.

FIG. 33 depicts another GUI 8840 for display on the display 112 depicted in FIG. 31, where the GUI 8840 is associated with the setup of the system 100 for the treatment of a horse. As shown in FIG. 33, the GUI 8840 also includes an animal selection window 8822, where "Horses" has already been selected from other listed animals, as indicated at Arrow A. The GUI 8840 also includes a treatment region selection window 8824, where "Spine-Rib-Pelvis (Anterior)" has already been selected from other listed treatment regions applicable to horses, as indicated by Arrow B. As a result of the selection of the "Spine-Rib-Pelvis (Anterior)" at Arrow B in window 8824, an image 8846 of an anterior region of a horse is depicted in an image window 8828. A trigger point 8850 for an associated treatment is shown in the image 8846. Touch sensitive screen buttons "Reference", "OK" and "Cancel" 8831-8833 are also included in the GUI 8840. In one embodiment, useful reference information may be accessed by the operator by selecting button 8831. Pressing button 8832 will return to the treatment screen and setup the system using the settings found in the selected treatment protocol. Pressing button 8833 will cause the selection screen to return to the treatment screen in its' last mode.

Figure 34:
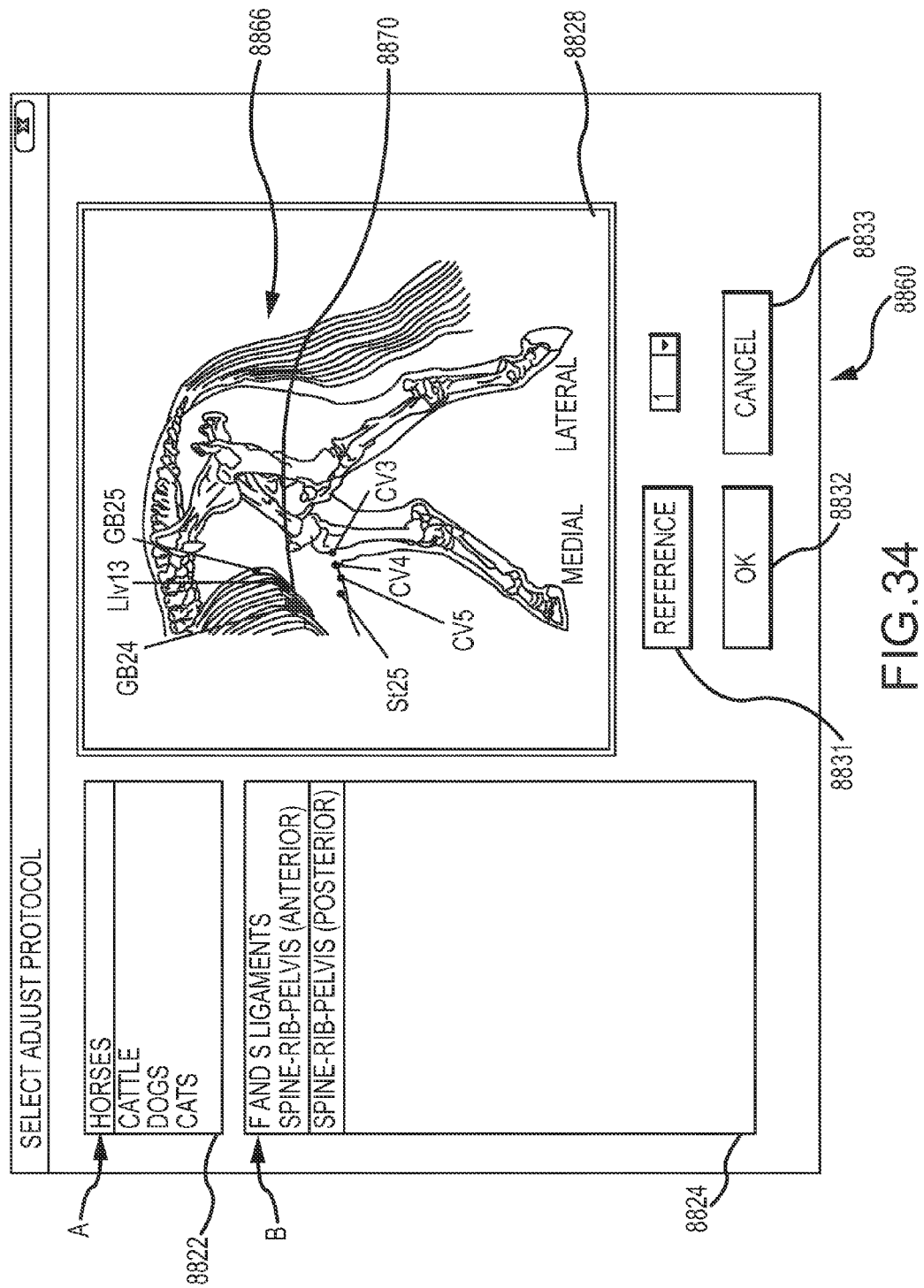
FIG. 34 depicts yet another GUI for display on the display depicted in FIG. 31, where the GUI is associated with the setup of the system for the treatment of a horse.

FIG. 34 depicts yet another GUI 8860 for display on the display 112 depicted in FIG. 31, where the GUI 8860 is associated with the setup of the system 100 for the treatment of a horse. As shown in FIG. 33, the GUI 8860 also includes an animal selection window 8822, where "Horses" has already been selected from other listed animals, as indicated at Arrow A. The GUI 8840 also includes a treatment region selection window 8824, where "Spine-Rib-Pelvis (Posterior)" has already been selected from other listed treatment regions applicable to horses, as indicated by Arrow B. As a result of the selection of the "Spine-Rib-Pelvis (Posterior)" at Arrow B in window 8824, an image 8866 of a posterior region of a horse is depicted in an image window 8828. A trigger point 8870 for an associated treatment is shown in the image 8866. Touch sensitive screen buttons "Reference", "OK" and "Cancel" 8831-8833 are also included in the GUI 8840. In one embodiment, useful reference information may be accessed by the operator by selecting button 8831. Pressing button 8832 will return to the treatment screen and setup the system using the settings found in the selected treatment protocol. Pressing button 8833 will cause the selection screen to return to the treatment screen in its' last mode.

Figure 35:
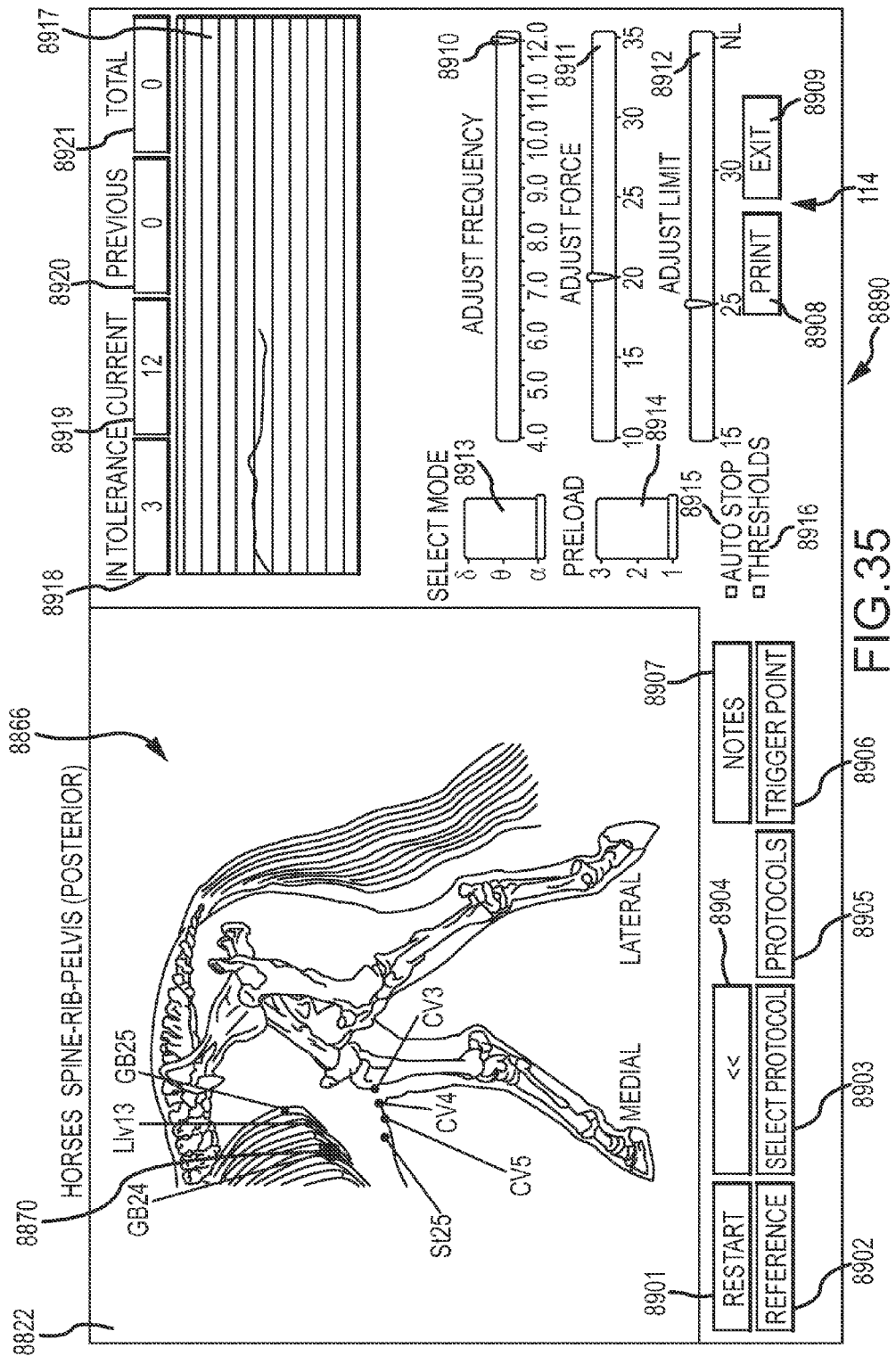
FIG. 35 illustrates a GUI for display on the display depicted in FIG. 31 once the setup of the system has been achieved via the GUI of FIG. 33.

FIG. 35 illustrates a GUI 8900 for display on the display 112 depicted in FIG. 31 once the setup of the system 100 has been achieved via the GUI 8860 of FIG. 33. As indicated in FIG. 35, the GUI 8900 includes the posterior horse image 8866 with its trigger point 8870. The GUI 8900 also includes an input device 114 with touch sensitive screen buttons "Restart", "Reference", "Select Protocol", "<<", "Protocols", "Trigger Point", "Notes", "Print", and "Exit" 8901-8909. The input device 114 of the GUI 8900 also includes an touch sensitive screen sliders "Adjust Frequency", "Adjust Force", "Adjust Limit", "Select Mode", and "Preload" 8910-8914. Finally, the GUI 8900 also includes "Auto Stop" and "Thresholds" indicates 8915 and 8916 and a graphical display 8917 to illustrate the treatment and "In Tolerance", "Current", "Previous" and "Total" indicators 8918-8921.

In one embodiment, the user interface contains various controls that aid the user by providing control and treatment feedback information. If the user makes an error they can easily restart the protocol by simply pressing the "restart" button 8901. Additionally the user may wish to just go back to the previous point and can do so by selecting the "<<" selection 8904. The "Reference Button" 89011 is used to store information regarding the anatomical area of treatment, treatment overview and rationale, treatment goals and or expected responses. The user may also go back to the list of protocols by choosing the "select protocol" button 8903.

Functionality can be quickly switched from a protocol to a trigger point by choosing either "protocol" 8905 or trigger point 8906 to select the type of therapy desired. The notes button 8907 brings up a window to allow the user to enter information in a text format via the keyboard. General treatment controls include frequency, force and limits 891. While the computer calculates the frequency, the user can override it by touching the screen and moving the digital slider. However, the force and limit have defaults that are parameters selected by the user to determine how much power will be used and the maximum number of impulses that can be delivered. The selection mode 8913 is used to chose what harmonic frequency is chosen within the range of frequencies of 0.1 to 12 Hz.

There are different input frequencies depending on whether one is attempting to stimulate a nerve, voluntary muscle fiber or involuntary muscle fiber. The ranges are Alpha 7-12, Theta 4-7, and Delta 0.1 to 4 Hz. The selection mode slider 8913 allows the user to dynamically choose the proper harmonic dynamically.

The preload function 8914 changes the amount of pressure that is used to compress the tissue before the treatment applicator begins to produce impulse. Because animals vary widely in their physiological characteristics and tolerances, varying amounts of pressure can be used. Preload 8914 provides a way to control this pressure without having to change treatment heads.

As treatment is progressing, information about the tissue response is shown on a strip chart 8917. Information includes real time output from the sensor showing changes in tissue tone, changes in tissue frequency response and changes in wave shape characteristics. If auto-stop is chosen 8915, these signals will be interpreted and the device will automatically stop treatment based upon a definable tolerance. For instance, if a tolerance of 3% is used for tissue stiffness, the device will stop treatment based upon receiving a predefined number of impulses that are all within 3% of each other.

Thresholds 8916 may be turned on or off to give the user a visual scale of how the treatment parameters are progressing in real time with regard to the auto-stop parameters. As the treatment progresses the real time measurements are tabulated in 8918 through 8921. "In tolerance" 8918 displays the impulses that fall within the pre-defined tolerance indications. "Current" 8918 displays the number of impulses that have been delivered during the activation of the treatment head during the active treatment while "previous" 8920 shows the previous number of impulses during the last treatment application and "total" displays the total number of impacts delivered during the entire treatment. After the treatment is concluded the users may print the screen by selecting the "print" button 8908 or the user may simply exit the protocol screen by touching the "exit" button 8909.

In one embodiment, the use and operation of the system 100 depicted in FIGS. 30-35 is as described above.

As can be understood from the preceding discussion of the veterinarian system 100, the system 100 is highly useful for veterinarians. Unlike medical doctors who practice only on humans and, as a result, only have to learn a single type of anatomy and associated treatments, veterinarians must learn many different types of anatomies and associated specific medical treatments, both of which can vary greatly among species and, in some instances, even among breeds.

In one embodiment as can understood from preceding discussion, the system 100 includes a database 122 contained in a memory. The database contains data categorized by species. The data includes species images, species body parts, treatment reference points associated with the species body parts, and treatment protocols associated with specific reference points. The system is configured such that a selection of a specific species from the database provides the ability to input information into the system regarding at least one of age, size, weight, breed, condition, or health. For example, if the species selected from a group of possible species (e.g., horse, cattle, dogs, cats, whales, etc.) contained in the database is a horse, then the user might be prompted by the system to input the horse's age, size, weight, breed, condition, health, what the horse is used for (e.g., racing, draft/work, cow horse, rodeo, etc.) or other information regarding the specific horse. The system is also configured such that a selection of a specific species from the database provides the ability to select a specific region of the species for treatment. For example, once the horse species is selected, the user may be prompted to select a certain region of the horse (e.g., anterior leg or shoulder region) from a number of regions stored in the database. The selection of a specific region of the species causes an image of the specific region of the species to be displayed on a display of the system. For example, selection of the anterior leg region causes a corresponding image of a horse anterior leg region to be displayed on the display 112.

When the image of the region is displayed, at least one reference point associated with a treatment trigger point of the specific region of the species is caused to be displayed on the image of the specific region (For example, see FIGS. 9, 12, 15 and 35). The treatment trigger point may be stored in the database and referenced to the image to automatically appear. A treatment protocol specific to the treatment trigger point is also stored in the database referenced to the treatment trigger point. The treatment protocols may be associated with at least one of a neurological treatment, a muscular treatment or a circulatory treatment.

Because of the utility of the system 100, although a veterinarian may not have treated a specific species for in the specific area for a long time, if ever, the veterinarian may simply elect the proper species and treatment on the system that fits the clinical circumstances and animal presently before the veterinarian and the system will guide the veterinarian both with respect to proper treatment trigger points and treatment protocols tailored for the species, treatment area and trigger points.

Figure 36:
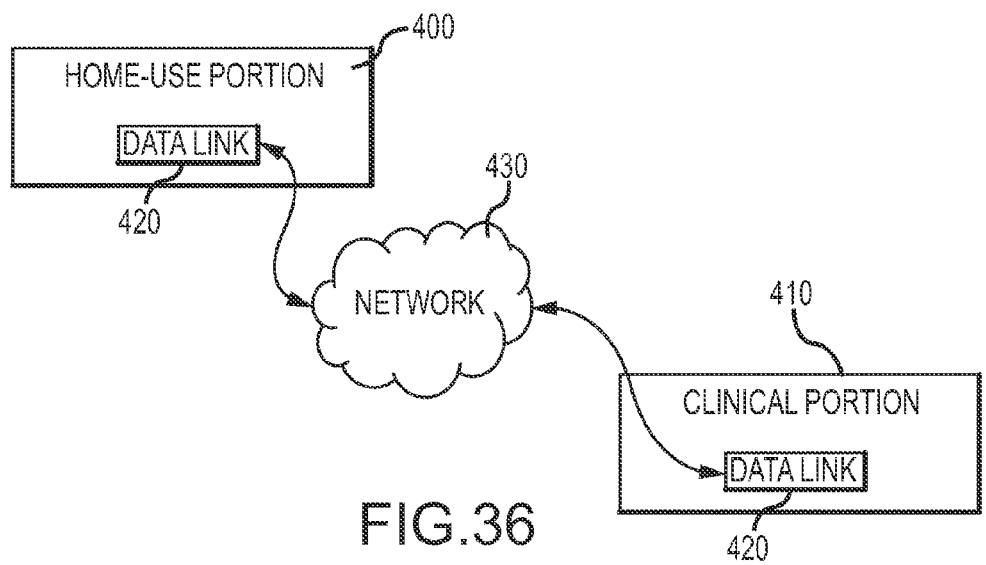
FIG. 36 is a schematic diagram of the system employing both the clinical and home-use portions connected by a network.
Figure 37:
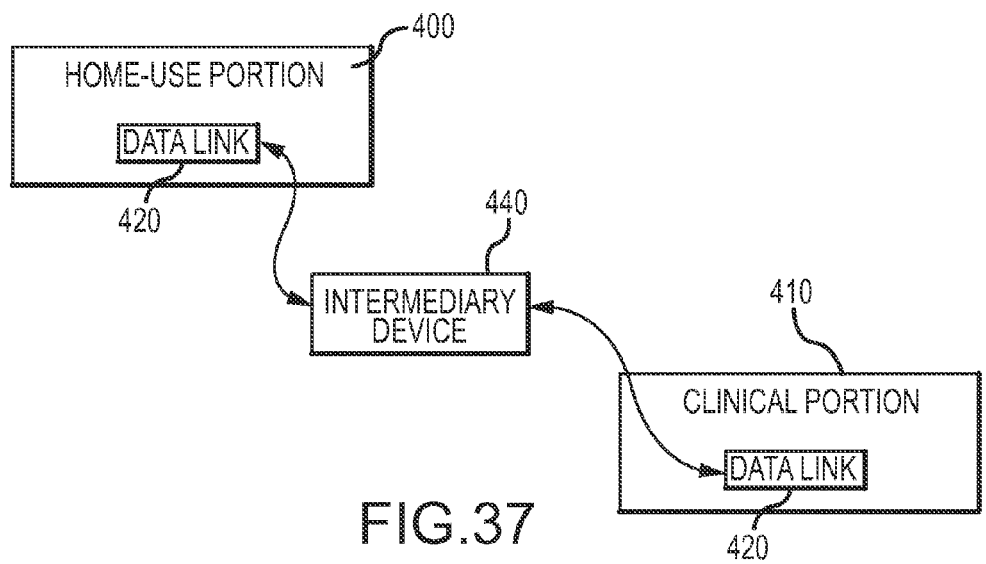
FIG. 37 is a schematic diagram of the system employing both the clinical and home-use portions connected by an intermediary device.

The embodiments of the system discussed above with respect to FIGS. 1-35 can also be employed as depicted in the diagrams of FIGS. 36 and 37, where the system may employ a portion for use by the veterinarian at the veterinarian clinic (i.e., a clinical portion) and a portion for use back at the farm or ranch (i.e., a stable-use portion). Specifically, the clinic portion is used by the veterinarian at the veterinarian clinic to diagnose the animal, formulate a treatment for the animal, treat the animal, and store treatment data associated with the actual treatment of the animal. The stable portion is provided with the formulated treatment and, possibly, the stored treatment data and sent back to the ranch or farm with the animal so treatment can be continued at the farm or ranch without having to return to the veterinarian clinic. For example, data and treatment information may be downloaded from the clinical portion into the stable-use portion. In one embodiment, the clinical portion may be configured like any of the embodiments of the system discussed above, and the stable-use portion may similarly configured but be in a more portable configuration, perhaps have fewer features as a result, and be capable of establishing a data link with the clinical portion.

As can be understood from FIGS. 36-37, in one embodiment, the stable-use portion 400 and the clinical portion 410 may connect via the data link 420. The data 420 link may comprise a connection between the stable-use portion 400 and the clinical portion 410 capable of uploading data relating to the operation and/or results of the treatment carried out on the stable-use portion 400. The data link 420 may comprise any means for connecting the stable-use portion 400 to the clinical portion 410 or a server, file storage system, or database that is readable by the clinical portion 410. For example, as indicated in FIG. 36, the data link may comprise a network connection 430 such as an Ethernet or Wi-Fi connection, a cellular connection, or any other network connection, and may connect to the clinical portion 410 either directly or through an intermediary such as over the Internet or any other network. The data link 420 may then upload operation and/or results data to the clinical portion for analysis.

In various embodiments, the data link 420 may comprise an I/O port capable of communicating with an intermediary device 440 that is in communication with the clinical portion 410. For example, as illustrated in FIG. 37 the intermediary device 440 may comprise a portable data storage device capable of being physically transported to the clinical portion 410 or connected to a device in electrical communication with the clinical portion 410. This may include a universal serial bus (USB) port connected to a USB drive, such as a conventional USB flash drive, external hard drive, or other USB enable storage device. The USB drive may be connected to the stable-use portion 400 and may receive data related to the operation and/or results of treatments carried out on the stable-use portion 400 from the data link 420. The USB drive may then be physically taken to the location of clinical portion 410 and the data uploaded via the data link 420 onto the clinical portion 410. In various other embodiments, the USB drive may be connected to a home computer or any other Internet-enabled device and the data may be uploaded to the clinical portion 410.

In various embodiments, the data link 420 may be configured to automatically send the operation and/or results data to the clinical portion. This may be done every time the stable-use portion has completed treatment, at set time intervals, upon the request of the clinical portion, or according to the treatment results. For example, the data link may automatically upload the operations and/or results data at the end of every week. In another example, the data link may automatically upload the operations and/or results data when a result exceeds a threshold in some way. This may include one of many relevant comparisons. For example, besides tracking the user's treatment results, the stable-use portion also may keep track of average results and standard deviation. If a user's results are unsatisfactory on average for a period of time, then modifications may be needed and the user's treatment and the data link may automatically send the operation and/or results data to the clinical portion regarding the poor results average. Similarly, if the user experiences outlier results that are outside of a set number of standard deviations from average, then the results may be uploaded. In the case of a non-network connected communications link, the user may be prompted by the stable-use system to connect the intermediary device and either upload the data to the clinical portion or to take the intermediary device to their veterinarian.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A veterinarian system for treating an animal, the system comprising:
   a display configured to display information associated with a treatment of the animal, the display configured to provide for a selection of a type of animal to be treated and a region of the animal to be treated, the region of the animal being shown as an image of the region on the display, a trigger point associated with the treatment of the animal being identified on the image;
   an input device comprising at least one of a key board or a touch screen in electrical communication with the display, the input device configured to receive information associated with the treatment of the animal to be delivered at the trigger point;
   a central processing unit (CPU) in electrical communication with the input device;
   a memory in electrical communication with the CPU and including treatment parameters associated with the treatment of the animal to be delivered at the trigger point;
   a first radio frequency (RF) head capable of being placed in electrical communication with the CPU and configured to generate RF energy over a range of frequencies; and
   a RF receiver antenna capable of being placed in electrical communication with the CPU and configured to detect the RF energy transmitted through a tissue from the first RF head;
   a plurality of second RF heads in electrical communication with the CPU, each second RF head having a piezoelectric transducer tuned to a unique frequency; and an electromyogram (EMG) sensor capable of being placed in electrical communication with the CPU and configured to detect electromyogram in the tissue at the trigger point;

wherein, when the first RF head and RF receiver antenna are applied to the tissue at the trigger point, the system is configured to: a) cause the first RF head to administer RF energy to the tissue over the range of RF frequencies; b) cause the RF receiver antenna to sense the administered RF energy transmitted through the tissue; c) identify a RF frequency having a most transmissibility through the tissue; and d) recommend a second RF head of the plurality of second RF heads that is capable of providing the identified RF frequency, wherein, when the recommended second RF head and EMG sensor are applied to the tissue, the system is configured to: a) cause the recommended second RF head to administer RF energy at the identified RF frequency to the tissue over a range of pulse frequencies; b) cause the EMG sensor to detect electromyogram in the tissue arising due to the RF energy administered to the tissue over the range of pulse frequencies; c) identify a pulse frequency having a highest electromyogram readings in the tissue; and d) treat the tissue with the recommended second RF head at the identified RF frequency and the identified pulse frequency.

2. The system of claim 1, wherein the first RF head comprises an array of piezoelectric transducers.

3. The system of claim 2, wherein the array is configured to generate RF over a range of between 500 KHz and 1.5 MHz.

4. The system of claim 2, wherein the array is configured to generate RF over a range of between 500 KHz and 1.5 MHz at steps of between 50 KHz and 200 KHz.

5. The system of claim 2, where the piezoelectric transducers of the array includes a first piezoelectric transducer, a second piezoelectric transducer, and a third piezoelectric transducer, wherein each of the first, second and third piezoelectric transducers generate RF at distinct frequencies from each other.

6. The system of claim 1, wherein the plurality of second RF heads includes individual second RF heads each tuned to a unique frequency from each other and each unique frequency is between 500 KHz and 1.5 MHz.

7. The system of claim 1, wherein, when the recommended second RF head is caused to administer RF energy at the identified RF frequency to the tissue over the range of pulse frequencies of between 1 Hz and 300 Hz.

8. The system of claim 1, wherein the recommended second RF head is caused to administer RF energy at the identified RF frequency to the tissue over the range of pulse frequencies of between 500 KHz and 1.5 MHz at steps programmatically controlled and optimized for tissue type via stored protocols.

9. The system of claim 1, further comprising an impulse head capable of being placed in electrical communication with the CPU and including a solenoid driven anvil configured to deliver mechanical impulse energy to the tissue, the impulse head further including a transducer sensor for detecting a wave generated in the tissue via an administration of the mechanical impulse energy to the tissue.

10. The system of claim 1, wherein the display comprises a liquid crystal display (LCD).

* * * * *